US011819019B2

(12) United States Patent
Eudes et al.

(10) Patent No.: US 11,819,019 B2
(45) Date of Patent: Nov. 21, 2023

(54) PROTEIN-FREE SEMEN CRYOPRESERVATION

(71) Applicant: University of Saskatchewan, Saskatoon (CA)

(72) Inventors: Francois Eudes, South Lethbridge (CA); Jaswant Singh, Saskatoon (CA); Kosala Rajapaksha, Saskatoon (CA); Muhammad Anzar, Saskatoon (CA); Gregg P. Adams, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 439 days.

(21) Appl. No.: 16/768,807

(22) PCT Filed: Dec. 3, 2018

(86) PCT No.: PCT/CA2018/051545
§ 371 (c)(1),
(2) Date: Jun. 1, 2020

(87) PCT Pub. No.: WO2019/104446
PCT Pub. Date: Jun. 6, 2019

(65) Prior Publication Data
US 2021/0059241 A1 Mar. 4, 2021

Related U.S. Application Data

(60) Provisional application No. 62/593,652, filed on Dec. 1, 2017.

(51) Int. Cl.
*A01N 1/02* (2006.01)
*C12N 5/076* (2010.01)

(52) U.S. Cl.
CPC ......... *A01N 1/0221* (2013.01); *A01N 1/0278* (2013.01); *A01N 1/0284* (2013.01); *C12N 5/061* (2013.01)

(58) Field of Classification Search
None
See application file for complete search history.

(56) References Cited

U.S. PATENT DOCUMENTS 6,368,786 B1 4/2002 Saint-Ramon et al.
7,208,265 B1 4/2007 Schenk

FOREIGN PATENT DOCUMENTS

WO WO02054864 A1 7/2002
WO WO-2011108946 A1 * 9/2011 ........... A01N 1/0226

OTHER PUBLICATIONS

E. Mocé et al., Treating ram sperm with cholesterol-loaded cyclodextrins improves cryosurvival. Animal Reproduction Science (2010) 118: 236-247. (Year: 2010).*
H. Sieme et al, Mode of action of cryoprotectants for sperm preservation. Animal Reproduction Science (2016): 2-5. (Year: 2016).*
AndroMed "Egg yolk free medium for bull semen" (Flyer) Aug. 2012. (Year: 2012).*
Blommaert, Didier et al. "Substitution of egg yolk by a cyclodextrin-cholesterol complex allows a reduction of the glycerol concentration into the freezing medium of equine sperm", Cryobiology 72 (2016) 27-32.
Cho, Sunghee et al. "A novel cell-permeable antioxidant peptide, SS31, attenuates ischemic brain injury by down-regulating CD36", JBC, Feb. 16, 2007 (Feb. 16, 2007), vol. 282, No. &, pp. 4634-4642.
Jones, Sarah et al. "Intracellular translocation and differential accumulation of cell-penetrating peptides in bovine spermatozoa: evaluation of efficient delivery vectors that do not compromise human sperm motility", Hum Reprod, Jul. 2013, vol. 28, No. 7, pp. 1874-1889.
Vatyavanich, Teraporn et al. "Rapid freezing versus slow programmable freezing of human spermatozoa", Fertil Steril, Apr. 2010, vol. 93, No. 6, pp. 1921-1928.
AndroMed "Egg yolk free medium for bull semen" (Flyer) Oct. 2018.
Akhter, S. et al. "In Vitro Evaluation of Liquid-stored Buffalo Semen at 5° C. Diluted in Soya Lecithin Based Extender (Bioxcell®), Tris-Citric Egg Yolk, Skim Milk and Egg Yolk-Citrate Extenders", Reprod Dom Anim 46, 45-49 (2011).
Anzar, M. et al. "Cryopreservation of bull semen shipped overnight and its effect on post-thaw sperm motility, plasma membrane integrity, mitochondrial membrane potential and normal acrosomes", Animal Reproduction Science 126 (2011) 23-31.
Combes, G.B. et al. "Effect of cholesterol on the motility and plasma membrane integrity of frozen equine spermatozoa after thawing", Journal of Reproduction and Fertility. Supplement 56, 127-132 (1999).
Boughter, Christopher T. et al. "Influence of Cholesterol on Phospholipid Bilayer Structure and Dynamics", J. Phys. Chem. B 2016, 120, 11761-11772.
Crespilho, A.M. et al. "Comparison of in vitro and in vivo fertilizing potential of bovine semen frozen in egg yolk or new lecithin based extenders", Livestock Science 149 (2012) 1-6.

(Continued)

*Primary Examiner* — Allison M Fox
*Assistant Examiner* — Alyssa G Weston
(74) *Attorney, Agent, or Firm* — Bereskin & Parr LLP; Carmela De Luca; Herman Cheung

(57) ABSTRACT

This disclosure provides a preserving composition comprising a cholesterol: carrier complex, optionally a cholesterol:cyclodextrin complex (CC complex) and/or a cell permeable antioxidant peptide and a biological buffer and optionally a cryprotectant, wherein the preserving composition is optionally substantially free of animal phospholipid, animal protein and/or animal lipoprotein. The disclosure also provides methods for the use of the preserving composition in cryopreservation of semen or sperm cells. Also provided is a kit comprising the preserving composition having a CC complex, a biological buffer, a cryoprotectant, a carbohydrate, a pH stabilizer, an antibiotic or antibiotic cocktail and/or a cell permeable anti-oxidant peptide.

20 Claims, 20 Drawing Sheets

Specification includes a Sequence Listing.

(56) References Cited

OTHER PUBLICATIONS

Hussain, S.A. et al. "A strategy for improvement of postthaw quality of bison sperm", Theriogenology 79 (2013) 108-115.
Moussa, M. et al. "Low density lipoproteins extracted from hen egg yolk by an easy method: cryoprotective effect on frozen-thawed bull semen", Theriogenology 57 (2002) 1695-1706.
Muiño, R. et al. "Post-thaw Survival and Longevity of Bull Spermatozoa Frozen with an Egg Yolk-based or Two Egg Yolk-free Extenders after an Equilibration Period of 18 h", Reprod Dom Anim 42, 305-311 (2007).
Nolan, John P. et al. "Regulation of membrane stability and the acrosome reaction in mammaliam sperm", FASEB J 11(8), 670-682 (1997).
OPTIXcell "Protein-free egg yolk-like media for frozen and fresh bovine semen" Breakthrough Technology Liposome inside (Flyer) Jul. 2012.
Pace, M. M. et al. "Components in egg yolk which protect bovine spermatozoa during freezing", Journal of Animal Science, vil. 39, No. 6, 1974.
Polge, C. "Fertilizing Capacity of Bull Spermatozoa after Freezing at -79° C.", Nature 169 (4302), 626-627 (1952).
Prentice-Biensch, Jennifer R. et al. "Vitrification of immature bovine cumulus-oocyte complexes: effects of cryoprotectants, the vitrification procedure and warming time on cleavage and embryo development" Reproductive Biology and Endocrinology 2012, 10:73.
Purdy, P.H. et al. "Effect of cholesterol-loaded cyclodextrin on the cryosurvival of bull sperm", Cryobiology 48 (2004) 36-45.
Sieme, H. et al. "Sperm Membrane Behaviour during Cooling and Cryopreservation", Reprod Dom Anim 50 (Suppl. 3), 20-26 (2015).
Tomás, C. et al. "Treating boar sperm with cholesterol-loaded cyclodextrins widens the sperm osmotic tolerance limits and enhances the in vitro sperm fertilising ability", Animal Reproduction Science 129 (2011) 209-220.
Van Wagtendonk-de Leeuw, A. M. et al. "Fertility results using bovine semen cryopreserved with extenders based on egg yolk and soy bean extract", Theriogenology, 54(1), 57-67 (1999).
Wündrich, Katja et al. "Activation of caspases in human spermatozoa during cryopreservation—an immunoblot study", Cell and Tissue Banking (2006) 7:81-90.
Bergeron, A. et al. "New Insights Towards Understanding the Mechanisms of Sperm Protection by Egg Yolk and Milk", Molecular Reproduction and Development 73:1338-1344 (2006).
Vidament, M. et al. "Glycerol in semen extender is a limiting factor in the fertility in asine and equine species", Animal Reproduction Science, 89, 302-305 (2005).
Yang, S.X. et al. "Animal Protein-Free Semen Extender for Fixed-Time Insemination of Beef Cows", Reproduction, Fertility and Development 30(1) 141-141, Dec. 4, 2017. 44th IETS Annual Conference (Abstract).
Yang, S.X. et al. "Animal Protein-Free Semen Extender for Fixed-Time Insemination of Beef Cows", 44th IETS Annual Conference (Presentation).
Lessard, C., et al., "Banking North American buffalo semen." Theriogenology, 2009, 71, pp. 1112-1119.
Singh, A.K., et al., "Comparison of in vitro and in vivo fertilizing potential of buffalo bull semen frozen in egg yolk-, soya bean lecithin- and liposome-based extenders." Reprod Dom Anim, 2018, 53, pp. 195-202.

\* cited by examiner

A

B

A

B

A

B

A

B

| Bull | Motility % | Progressive Motility % |
|---|---|---|
| 1 | 66.69 | 61.67 |
| 2 | 72.38 | 67.48 |
| 3 | 49.25 | 42.83 |

FIG. 17

PROTEIN-FREE SEMEN CRYOPRESERVATION

CROSS-REFERENCE TO RELATED APPLICATIONS

This application is a National Phase Entry of PCT/CA2018/051545, filed Dec. 3, 2018, which claims the benefit of United States Provisional Patent Applications U.S. Ser. No. 62/593,652 filed Dec. 1, 2017 each of these applications being incorporated herein in their entirety by reference.

INCORPORATION OF SEQUENCE LISTING

A computer readable form of the Sequence Listing "P54866PC00_SequenceListing" (1,060 bytes) created on Dec. 3, 2018, is herein incorporated by reference.

FIELD

This disclosure generally relates to the field of semen cryopreservation for artificial insemination aimed to maintain and extend the vitality of productive sperm cells. More particularly, it concerns compositions and methods relating to a preserving composition containing a cholesterol carrier complex such as a cholesterol:cyclodextrin complex and/or a cell permeable antioxidant peptide, optionally wherein the preserving composition is substantially free of egg yolk, milk protein or other animal source phospholipid, or proteinprotein, for cryopreservation of semen containing sperm cells.

BACKGROUND

Current semen cryopreservation protocols include the use of phospholipids, lipoproteins and cholesterol, of which egg yolk contains all three, in semen extenders. The stages of semen cryopreservation typically include the steps of 1) dilution involving egg yolk or milk extenders; 2) cooling from, for example, 22° C. to 4° C. over a time period of at least 90 min; 3) equilibration with cryoprotectants; 4) freezing; and 5) thawing when insemination is to be carried out. During the cooling stage, membrane phase transition occurs. Sperm plasma membranes are lipid bilayers that contain heterogeneous phospholipids and proteins. During the initial cooling stage, phospholipids, which prefer non-bilayers, form separate gel phase domains. Retaining of phospholipid and protein distribution and orientation is desirable during cooling process. Upon thawing, membrane asymmetry is retained, but there is reduced enzyme activity, increased cations and water permeability which affect sperm quality.

When semen cryopreservation is carried out in the absence of egg yolk, sperm quality is drastically reduced after freezing and thawing, resulting in decreased sperm parameters such as sperm total, progressive motility and pregnancy rates.

Cholesterol is an integral component of plasma membrane of mammalian cells which stabilizes plasma membrane (Nolan and Hammerstedt 1997). During initial cooling from room temperature to 0° C. (suprazero phase), plasma membrane undergo thermotropic phase transition which ultimately destabilizes the plasm membrane organization. Cholesterol protects sperm during suprazero membrane phase and modulates thermotropic membrane phase behavior (Sieme et al. 2015). Higher cholesterol:phospholipid has been shown to reduce membrane disorganization caused by phase transition (Boughter et al. 2016).

Improvement of sperm cryopreservation parameters has been seen after semen treatment with the combination of egg yolk and cholesterol-cyclodextrin complex in stallion (Combes et al. 2000), bull (Purdy & Graham 2004), boar (Tomás et al. 2011) and bison (Hussain et al. 2013).

Commercial semen extenders include AndroMed (Minitube) which contains phospholipids, TRIS, citric acid, sugars, anti-oxidants, buffers, and glycerol; OptixCell (IMV Technologies) which is a protein-free egg yolk-like media that contains artificially prepared liposomes; and BioxCell (IMV Technologies) which is a soya lecithin-based extender (Akhter et al. 2011). For example, liposome is an expensive preparation. Quality and fertility of semen have been reported to be less when treated with plant-based extender compared with egg yolk-based extenders (Muiño et al. 2007; Van Wagtendonk-de Leeuw et al. 2000; Crespilho et al. 2012).

Glycerol is a conventionally used cryoprotectant. At a concentration of greater than 3.5% in a preservation medium, it has been reported to be toxic to equine sperm (Vidament et al, 2005). In the presence of preservation medium INRA 96 and supplemented with hydroxypropyl-beta-cyclodextrin cholesterol (HPβCD-C) complex, glycerol concentration greater than 2% in the freezing medium resulted in decreased sperm viability, as compared to 1% glycerol (Blommaert et al. 2016).

The use of animal products, such as egg yolk in semen extenders, however, raises important biosecurity concerns related to the transmission of infectious agents. The inclusion of egg yolk, milk protein or other animal source phospholipid, protein or lipoprotein in semen extenders requires time to prepare and can also incur an economic cost to the user.

Alternate or improved semen or sperm cells preserving compositions that may avoid biosecurity concerns, save time and/or reduce cost are desirable.

SUMMARY

Preserving compositions for preserving semen and/or isolated sperm cells that may for example avoid biosecurity concerns, save time and/or reduce cost are provided. The preserving compositions described hereinare substantially free of egg yolk, milk protein and/or other animal source phospholipid, protein or lipoprotein and provide an effective alternative for preserving optionally cryopreserving semen and/or isolated sperm cells. The preserving composition can be substantially free of animal origin ingredients. As shown in the Examples, the preserving compositions described herein provide for similar or improved sperm quality parameters when compared to standard sperm cells preserving compositions. The preserving compositions can comprise a cholesterol carrier complex. The preserving composition comprising the cholesterol:carrier complex can be incubated with ejaculate in the absence of or presence of cryoprotectants such as glycerol. Accordingly the method can include where the preservation comprises two steps—incubation with cholesterol carrier complex followed by addition of a preserving solution comprising a cryoprotectant, or a step wherein the cholesterol carrier complex and cryoprotectant are provided in a composition (see for Example FIG. 20).

One aspect includes a method of preserving semen or sperm cells comprising:

a. i) combining an ejaculate containing sperm cells and/or isolated sperm cells with a cholesterol: carrier complex preserving composition, optionally a cholesterol:cyclodextrin complex (CC complex) and/or polyethyleneglycol conjugated cholesterol (PEG-C conjugate) preserving composition to provide a cholesterol: carrier sperm cells composition and combining the cholesterol: carrier sperm cells composition with a sperm cells preserving composition comprising a cryoprotectant, optionally glycerol and a biological buffer to provide a preserved sperm cells composition; wherein the cholesterol: carrier complex preserving composition and/or the sperm cells preserving composition is substantially free of animal phospholipid, animal protein, and/or animal lipoprotein, for example free of animal source ingredients; or ii) combining an ejaculate containing sperm cells and/or isolated sperm cells with a sperm cells preserving composition to provide a preserved sperm cells composition, the sperm cells preserving composition comprising a cholesterol: carrier complex, optionally cholesterol:cyclodextrin complex (CC complex) and/or polyethyleneglycol conjugated cholesterol (PEG-C conjugate), a cryoprotectant, optionally glycerol, and a biological buffer, wherein the sperm cells preserving composition is substantially free of animal phospholipid, animal protein, and/or animal lipoprotein, for example free of animal source ingredients;

and optionally b. freezing the preserved sperm cells composition.

Alternatively, the preserved sperm cells composition in another embodiment, is cooled and stored above 0° C., for example at 4° C. In such methods cryoprotectant may or may not be included in the preserving composition.

In one embodiment, the preserving composition, optionally the cholesterol: carrier complex preserving composition and/or the sperm cells preserving composition is substantially free of protein.

The ejaculate and/or isolated sperm cells may be combined with the preserving composition, optionally the cholesterol: carrier complex preserving composition or the sperm cells preserving composition for example within 5 or 10 minutes of retrieval, or after about 30 minutes, or about 45 minutes from retrieval and within about 60 minutes or 90 minutes from retrieval.

In an embodiment, the preserving composition further comprises a cell permeable anti-oxidant peptide.

Another aspect of the disclosure provides a preserving composition such as a sperm cells preserving composition that is substantially free of egg yolk, milk protein and/or other animal source phospholipid, protein, and/or lipoprotein or for example any ingredients of animal origin. In one embodiment, the composition optionally the sperm cells preserving composition comprises a cholesterol:cyclodextrin complex (CC complex) and/or PEG conjugated cholesterol (PEG-C conjugate) along with one or more other components described herein.

In an embodiment, the composition such as the cholesterol: carrier complex preserving composition and/or the sperm cells preserving composition comprises about or at least 0.125 mg/ml of a cholesterol:cyclodextrin complex (CC complex) and a biological buffer, and substantially free of animal phospholipid, animal protein, and/or animal lipoprotein, and can for example be provided in a reconstituted solution or in a powder form for reconstitution. In an embodiment, the preserving composition such as the sperm cells preserving composition and/or one or more components thereof such as the CC complex and/or the PEG-C conjugate is in a powder form for reconstitution, optionally with a biological buffer optionally comprising a cryoprotectant for example a Tris buffer glycerol solution.

Also provided is a kit comprising one or more compositions described herein.

Other features and advantages of the present disclosure will become apparent from the following detailed description. It should be understood, however, that the detailed description and the specific Examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments are described below in relation to the drawings in which:

FIGS. 5A to 5D are a plurality of graphs depicting sperm properties post thaw. FIG. 5A is a graph of post-thaw sperm total motility, FIG. 5B is a graph of progressive motility, FIG. 5C is a graph of average path velocity, FIG. 5D is a graph of curvilinear velocity and FIG. 5E is a graph of straight-line velocity in TEYG (20%, v/v, egg yolk), TG (0% egg yolk), and cholesterol-cyclodextrin complex (CC0 or 2 mg mL$^{-1}$). Each bar represents mean±SEM from six independent replicates. Within a motion characteristic, bars with different letters (a-c) differ from each other (P<0.05).

FIG. 6A shows a video still of post-thaw sperms with egg yolk.

FIG. 7A is a graph of post-thaw sperm total motility, FIG. 7B is a graph of progressive motility, FIG. 7C is a graph of average path velocity, FIG. 7D is a graph of curvilinear velocity, and FIG. 7E is a graph of a straight-line velocity in conventional egg yolk extender (control) or without egg yolk. In egg yolk-free group, bull sperm were pre-exposed to cholesterol-cyclodextrin (CC) complex (2, 3 or 4 mg ml$^{-1}$) at 22° C. for 15 min and then diluted (1:1) in tris-glycerol (TG) extender (final glycerol concentration 7, 5, 3, 1 or 0%, v/v) at 22° C. Bars with different letters (a-d) within a sperm characteristic differ from each other (P<0.05).

FIG. 8A is a graph of total motility, FIG. 8B is a graph of progressive motility, FIG. 8C is a graph of average path velocity, FIG. 8D is a graph of curvilinear velocity, and FIG. 8E is a graph of straight-line velocity, in bull semen frozen with egg yolk (control) and without egg yolk. In egg yolk-free group, bull sperm were pre-exposed to cholesterol-cyclodextrin complex (CC; 2 mg ml$^{-1}$) at 22° C. for 15 min and then diluted (1:1) in tris-glycerol (TG) extender (final glycerol concentration 7, 9 or 11%, v/v) at 22° C. Bars with different letters (a,b) differ from each other (P<0.05).

FIG. 10A is a phase contrast image after SS31 exposure. FIG. 10B shows CPP (i.e. SS31) binding. Arrows point to uptake of SS31 by sperm cells. FIG. 10C shows live sperm cells after SS31 exposure. Arrows point to live sperm with intact membrane. FIG. 10D is a phase contrast image after mTP4 exposure. FIG. 10E shows CPP (i.e. mTP4) binding. Arrows point to uptake of mTP4 by sperm cells. FIG. 10F shows live sperm cells after mTP4 exposure. Arrows point to live sperm with intact membrane.

FIG. 11A is a flow cytometry graph for bull sperm with no exposure to CPP. FIG. 11A is a flow cytometry graph for bull sperm having exposed to mTP4. FIG. 11A is a flow cytometry graph for bull sperm having exposed to SS31. For analysis, the population of sperm in quadrant Q2 representing live sperm with cell penetrating peptide was used.

FIG. 13A is a graph of total motility.

FIG. 14A is a graph showing the effect of mTP4 and SS31 on post-thaw sperm total motility at 0, 2, and 4 hrs.

FIG. 15A is a graph showing percent decline in sperm total motility after exposure to mTP4 and SS31 for 2 and 4 hrs.

FIG. 17 is a chart showing the results of post-thaw sperm total motility and progressive motility according to processing in FIG. 16. Motility % refers to total motility %. Abbreviations: CASA: Computer Assisted Semen Analysis.

FIG. 19A is a graph of total motility, FIG. 19B is a graph of progressive motility, and FIG. 19C is a graph of live and intact acrosome, of bull semen frozen with tris-citric buffer with glycerol containing egg yolk (EY) or cholesterol:cyclodextrin (CC) complex, and frozen by either programmable freezing (PF) or vapor freezing (VF). FIG. 19D is a graph of blastocyst rate of bull semen frozen with tris-citric buffer with glycerol containing (CC) complex, and frozen by either programmed freezing (PF) or vapor freezing (VF). Each bar represents mean±SEM. *Asterisk represent significant difference (P<0.05) between semen frozen in CC using programmable freezing and the remaining treatments.

DETAILED DESCRIPTION OF THE DISCLOSURE

I. Definitions

Figure 1:
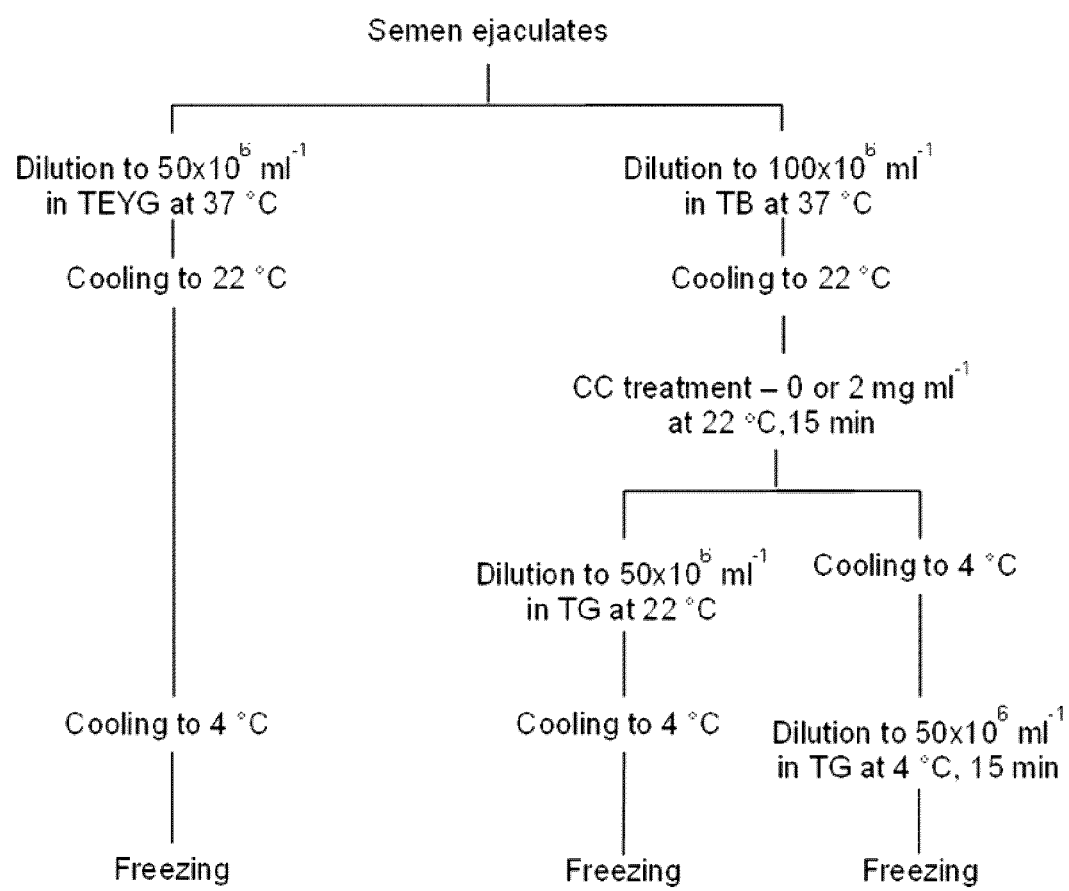
FIG. 1 is a flow chart of semen collection and processing.

The term "preserve" or a derivative thereof as used herein refers to protectingthe viability and/or vigor of cells, such as sperm cells, such that the sperm cells retain motility, velocity, and/or structural characteristics, which is useful for insemination, optionally under storage, cooled around 4° C. (e.g. 0-7° C.) or frozen, e.g below 0° C. (e.g. below or at about −20° C., below or at about −40° C. or below or at about −80° C. or below or about −190° C.).

The phrase "preserving composition" also referred to alternatively as "semen extender" or "semen extender composition" as used herein refers to a composition, optionally a solution, suspension, or powder for resuspension, compatible with and for protecting the viability and/or vigor of cells, for example wherein the cells are comprised in a biological fluid, such as for the protecting the viability and/or vigor of semen, which is a biological fluid that contains sperm cells. The preserving composition can also be used with isolated sperm cells. The preserving solution can be iso-osmotic to semen and include sufficient buffering capacity to neutralize pH for example change due to cell metabolism. The preserving composition can be used to dilute semen and for example "extend" the volume of semen for making a larger number of semen doses. A preserving composition may comprise a cholesterol: carrier complex such as cholesterol:cyclodextrin complex (CC complex) and/or polyethyleneglycol conjugated cholesterol (PEG-C conjugate), optionally a cell permeable anti-oxidant peptide described herein, and a biological buffer such as those described herein, including a buffer containing tris and citric acid monohydrate, and optionally one or more of a cryoprotectant such as glycerol, a carbohydrate such as fructose, a pH stabilizer, and an antibiotic or antibiotic cocktail The preserving composition is for example substantially free of animal phospholipid, animal protein, and/or animal lipoprotein and optionally free of any animal origin ingredients. The cholesterol can be any plant cholesterol or phytosterol for example as described herein.

The term "cholesterol" as used herein refers to a compound of the sterol type, and includes animal cholesterol and related phytosterols, which are plant sterols and stanols from plant tissues, as well as combinations thereof (e.g. combination of animal cholesterol and plant cholesterol or combination of different plant cholesterols) as well as synthetic sources of any of the foregoing. Animal cholesterol can be from any animal, for example sheep. Phytosterols may be referred to as "plant cholesterol". Cholesterols are an essential structural component of all animal cell membranes and are essential to maintain both membrane structural integrity and fluidity. Animal cholesterol is the principal sterol synthesized by all animals. Phytosterols include beta-sitosterol, campesterol, and stigmasterol. Phytosterols may be sourced from, for example, yam, peanuts, flaxseeds, nuts, avocados, and hemp seeds.

The term "cyclodextrin" as used herein refers to a family of compounds made up of sugar molecules bound together in a ring, typically 6-8 glucopyranose units. Cyclodextrins are also known as cycloamyloses. Cyclodextrins that can be used include but are not limited to α-cyclodextrin, β-cyclodextrin, γ-cyclodextrin, methyl-α-cyclodextrin, methyl-β-cyclodextrin, and methyl-γ-cyclodextrin. The cyclodextrin can also be hydroxypropyl-β-cyclodextrin.

The phrase "cholesterol: carrier complex" refers to a carrier complexed or bound by electrostatic or other forces with cholesterol. The carrier can for example be a cyclodextrin which binds or complexes with cholesterol or a PEG compound which is conjugated to cholesterol (PEG-C conjugate). A carrier such as cyclodextrin has an inner hydrophobic core which binds cholesterol through hydrophobic interaction and a hydrophilic core which can bind plasma membrane.

The term "cholesterol:cyclodextrin", "cholesterol-cyclodextrin", "cholesterol:cyclodextrin complex", "cholesterol-cyclodextrin complex", "cholesterol-loaded cyclodextrin", "cholesterol-loaded cyclodextrin complex", "CC", or "CC complex" are used interchangeably and as used herein refers to a complex containing cholesterol and cyclodextrin. The ratio of cholesterol to cyclodextrin in a cholesterol:cyclodextrin complex by weight can be from about 1:100 to about 30:100 or be about or at least 1:100, 2:100, 3:100, 4:100, 5:100, 6:100, 7:100, 8:100, 9:100, 10:100, 11:100, 12:100, 13:100, 14:100, 15:100, 16:100, 17:100, 18:100, 19:100, 20:100, 21:100, 22:100, 23:100, 24:100, 25:100, 26:100, 27:100, 28:100, 29:100, or 30:100, optionally about or at least 9:100 or 20:100, preferably about or at least 9:100. The molar ratio of cholesterol to cyclodextrin in a cholesterol:cyclodextrin complex can be between 0.05 to 1, such as at least 0.05, 0.10, 0.15, 0.2, 0.25, 0.3, 0.35, 0.4, 0.45 and at most 0.3, 0.35, 0.4, 0.45, 0.5, 0.55, 0.6, 0.65, 0.7, 0.75, 0.8, 0.85, 0.9, 0.95, or 1.

The term "polyethylene glycol-cholesterol conjugates" or "PEG-C conjugate" as used herein refers pegylated conjugates of any cholesterol. For example, PEG-C conjugate can be purchased from Sigma-Aldrich (Cholesterol-PEG 600, Catalog number 69068-97-9)

The term "cryoprotectant" as used herein refers to a substance that protects cells or tissue from sub-zero freezing damage. Cryoprotectants include but are not limited to glycerol, sucrose, trehalose, dimethyl sulfoxide, polyethylene glycol, and propylene glycol.

The term "cell permeable anti-oxidant peptide" as used herein refers to a short peptide for example of about 4-20 amino acids, that typically has at least one lysine, arginine and/or relative abundance of positively charged residues, for example at least 30% and which can enter a cell and/or mitochondria (e.g. for example into a sperm cell), and which is potent at reducing intracellular reactive oxygen species (ROS), for example by at least 20%, at least 30%, at least 40%, at least 50% or more compared to a control cell not receiving the peptide, attributable typically to a tyrosine or dimethyltyrosine residue. By reducing intracellular ROS, the cell permeable-oxidant peptide" can prevent cell death caused by ROS (i.e. the oxidant).

The term "DMT-SS31" or "SS31" as used herein refers to a cell permeable anti-oxidant peptide that has the following amino acid sequence: D-Arg-DMT-Lys-Phe (SEQ ID NO:1), where D denotes a D-isomer, and where DMT denotes 2',6' dimethyltyrosine.

The term "DMT-mTP4" or "mTP4" as used herein refers to a cell permeable anti-oxidant peptide that has the following amino acid sequence: DMT-D-MWWRRSRTNSLRYT (SEQ ID NO:2), where D denotes a D-isomer, and where DMT denotes 2',6' dimethyltyrosine.

The term "variant" as used herein includes modifications or chemical equivalents of the amino acid sequences of the present disclosure that perform substantially the same function as the peptides of the disclosure in substantially the same way. For example, variants of peptides of the disclosure include, without limitation, conservative amino acid substitutions, additions and deletions to the peptides of the disclosure, and analogs and derivatives thereof.

A "conservative amino acid substitution", as used herein, is one in which one amino acid residue is replaced with another amino acid residue without abolishing the peptide's desired properties.

Table 1 provides an exemplary list of conservative substitutions.

TABLE 1

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "beta-sitosterol" as used herein refers to a phytosterol with the following chemical structure:

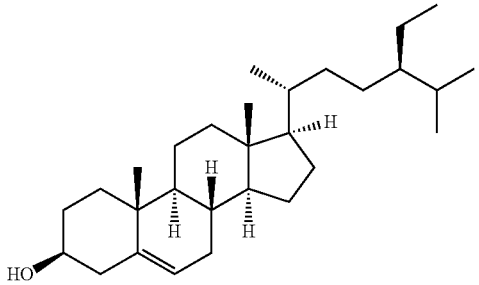

For example, a preparation that is at least or about 70% β-sitosterol available for example from Sigma Aldrich can be used.

The term "campesterol" as used herein refers to a phytosterol with the following chemical structure:

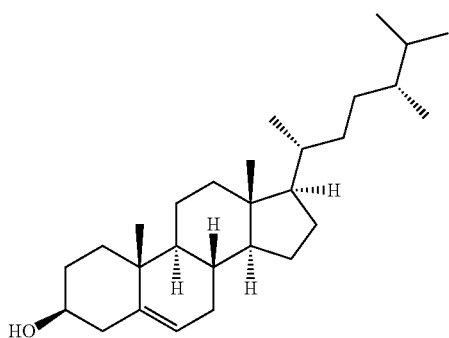

For example, a preparation that is at least or about 65% campesterol available for example from Sigma Aldrich can be used.

The term "stigmasterol" as used herein refers to a phytosterol with the following chemical structure:

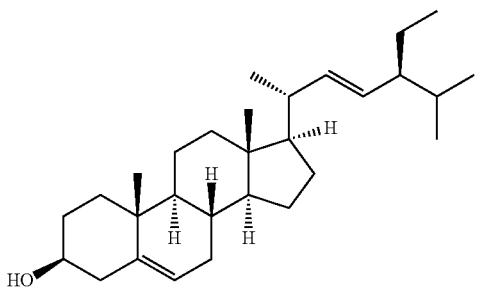

For example, a preparation that is at least or about 70%, at least or about 80%, at least or about 95% stigmasterol available for example from Sigma Aldrich can be used.

The term "PhytoChol" as used herein refers to an animal-origin free, vegetal-derived cholesterol also known as Cholesterol Puriss, having the following chemical structure:

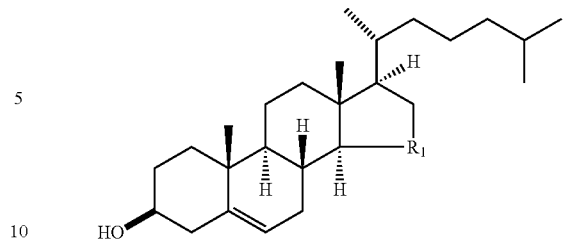

The term "freezing" as used herein refers to a stage in which a liquid turns into a solid when its temperature is lowered below its freezing point, or when the temperature of a composition drops below zero degree Centigrade. Freezing methods can comprise one or more cooling steps in addition to the step which converts a liquid into a solid. For example, freezing methods can comprise two phases: 1) supra-zero phase in which samples are frozen from body or room temperature to 4° C., and 2) sub-zero phase in which samples are frozen for example from 4° C. to −196° C.

The phrase "biological buffer" as used herein means a composition such as a powder (that can be introduced into a solution) or a solution that comprises any substance that can minimize changes in pH as acids or bases are added to the composition and which is compatible with cells such as sperm cells. Commonly used biological buffers include PBS, imidazole TRIS, HEPES, and TES buffer. Such biological buffers can be purchased as powders or solutions, or made from compounds purchased from Sigma Chemical Company. The molar concentration of the biological buffer in solution will depend on the particular buffer. For example, TRIS buffer can be between about 0.05 M and about 0.25 M. As another example, a Tris buffer that is 3.03% (w/v) in Milli-Q distilled water can be used. In another example, a Tris-citric acid buffer (TB, also referred to as TCA buffer) contains 3.03% (w/v) Tris and 1.74% (w/v) citric acid monohydrate in Milli-Q distilled water. The citric acid is used to provide a desired pH. In another example, the biological buffer contains 2.12% (w/v) sodium citrate dehydrate and 1.83% (w/v) citric acid monohydrate. In another example, the biological buffer is a zwitterion buffer comprising TES, HEPES, BES, and/or BICINE. The biological buffer may also contain one or more additional pH stabilizers.

The phrase "pH stabilizer" as used herein refers to a chemical additive that can be added to a biological buffer to provide additional pH stabilization, and includes for example citric acid.

The phrase "dilution solution" refers to any solution that is compatible with cells such as sperm cells and includes for example biological buffer solutions, commercially available semen extenders as well as preserving compositions described herein.

The term "carbohydrate" refers to any saccharide, including sugars, starch, cellulose, monosaccharides, disaccharides, oligosaccharides, and polysaccharides. In a preserving composition the carbohydrate can be fructose, sucrose, lactose, trehalose, galactose or glucose. Since trehalose can be both a cryoprotectant and a carbohydrate source, its inclusion in a composition described herein provides both cryoprotective quality and as a source of carbohydrate.

The phrase "substantially free" as used herein is used to refer to the complete or near complete lack of an action, characteristic, property, state, structure, item, or result. For example, a composition that is "substantially free of" animal phospholipid would either completely lack animal phospholipid, or so nearly completely lack animal phospholipid that the effect would be the same as if it completely lacked animal phospholipid. In other words, a composition that is "substantially free of" an ingredient or element may still actually contain such item as long as there is no measurable effect thereof. For example, a composition that is substantially free of an ingredient or element comprises less than about 1% by wt or less than about 1% vol/vol of the ingredient or element in the composition.

The term (w/v) as used herein refers to a measure of the concentration of a solution obtained by dividing the mass or weight of the solute by the volume of the solution.

The term "warm" as used herein with respect to a solution, such as dilution solution, means at least 22° C. and less than 40° C., for example 37° C., 32° C., or 22° C. or any temperature between about 20° C. and 40° C.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. Thus, for example, a composition containing "a cholesterol" includes a mixture of two or more cholesterols. It should also be noted that the term "or" is generally employed in its sense including "and/or" unless the content clearly dictates otherwise.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about."

The definitions and embodiments described in particular sections are intended to be applicable to other embodiments herein described for which they are suitable as would be understood by a person skilled in the art

II. Methods, Uses, and Compositions

In one aspect, the disclosure relates to preserving compositions and methods using a cholesterol: carrier complex such as a cholesterol:cyclodextrin complex, but no egg yolk, milk protein or animal phospholipid, protein or lipoproteins, for preservation such as cryopreservation of semen containing sperm cells and/or isolated sperm cells.

Accordingly, in one aspect the present disclosure provides a method of preserving semen or sperm cells comprising:
  i) combining an ejaculate containing sperm cells and/or isolated sperm cells with a cholesterol: carrier complex preserving composition, optionally a cholesterol:cyclodextrin complex (CC complex) and/or polyethyleneglycol conjugated cholesterol (PEG-C conjugate) preserving composition to provide a cholesterol: carrier sperm cells composition and combining the cholesterol: carrier sperm cells composition with a sperm cells preserving composition comprising a cryoprotectant, optionally glycerol, and a biological buffer to provide a preserved sperm cells composition wherein the cholesterol: carrier complex preserving composition and the sperm cells preserving composition is substantially free of animal phospholipid, animal protein, and/or animal lipoprotein, for example free of animal source ingredients; or
  ii) combining an ejaculate containing sperm cells and/or isolated sperm cells with a sperm cells preserving composition to provide a preserved sperm cells composition, the preserving composition comprising a cholesterol: carrier complex, optionally cholesterol:cyclodextrin complex (CC complex) and/or polyethyleneglycol conjugated cholesterol (PEG-C conjugate),
wherein the preserving composition is substantially free of animal phospholipid, animal protein, and/or animal lipoprotein.

In another aspect, the present disclosure provides a method of preserving semen or sperm cells comprising:
  a. i) combining an ejaculate containing sperm cells and/or isolated sperm cells with a cholesterol: carrier complex preserving composition, optionally cholesterol:cyclodextrin complex (CC complex) and/or polyethyleneglycol conjugated cholesterol (PEG-C conjugate) preserving composition to provide a cholesterol: carrier sperm cells composition and combining the cholesterol: carrier sperm cells composition with a sperm cells preserving composition comprising a cryoprotectant, optionally glycerol and a biological buffer to provide a preserved sperm cells composition wherein the cholesterol: carrier preserving composition and/or the sperm cells preserving composition is/are substantially free of animal phospholipid, animal protein, and/or animal lipoprotein, for example free of animal source ingredients; or
  ii) combining an ejaculate containing sperm cells and/or isolated sperm cells with a sperm cells preserving composition to provide a preserved sperm cells composition, the preserving composition comprising a cholesterol: carrier complex, optionally cholesterol:cyclodextrin complex (CC complex) and/or polyethyleneglycol conjugated cholesterol (PEG-C conjugate), a cryoprotectant, optionally glycerol, and a biological buffer, wherein the preserving composition is substantially free of animal phospholipid, animal protein, and/or animal lipoprotein, for example free of animal source ingredients; and
  b. freezing the preserved sperm cells composition. In an embodiment, the ejaculate and/or isolated sperm cells is in a biological buffer. For example the ejaculate and/or isolated sperm may be diluted in a biological buffer or other dilution solution, for example to dilute the sperm cell number to a desired concentration. The dilution can be prior to contact with the cholesterol: carrier and/or the sperm cells preserving composition. The cholesterol: carrier optionally CC complex can be added directly to the ejaculate and/or isolated sperm cells (e.g. as in i and either pre or post dilution) or may be added in a preserving composition comprising a cryoprotectant (e.g. as in ii and either pre or post dilution).

The cholesterol: carrier complex preserving composition is optionally prepared as described in Example 1 and comprises for example the cholesterol: carrier complex and a biological buffer, optionally wherein the biological buffer is a Tris buffer. Said composition can comprise one or more additional components described herein.

Another aspect of the disclosure provides a preserving composition that is substantially free of egg yolk, milk protein and/or other animal source phospholipid, protein, and/or lipoprotein or for example any ingredients of animal origin. The preserving composition optionally the sperm cells preserving composition comprises a cholesterol:cyclodextrin complex (CC complex) and/or PEG conjugated cholesterol (PEG-C conjugate) along with one or more other components.

In an embodiment, the preserving composition such as the cholesterol: carrier complex preserving composition or the sperm cells preserving composition comprises about or at least 0.125 mg/ml of a cholesterol:cyclodextrin complex (CC complex) and a biological buffer, and substantially free of animal phospholipid, animal protein, and/or animal lipoprotein, and can for example be provided in a reconstituted solution or in a powder form for reconstitution. In an embodiment, the preserving composition such as the sperm cells preserving composition and/or one or more components thereof such as the CC complex and/or the PEG-C conjugate is in a powder form for reconstitution, optionally with a biological buffer optionally comprising a cryoprotectant for example a Tris buffer glycerol solution.

The preserving compositions can be used in methods described herein.

In an embodiment, where the preserving composition does not comprise glycerol, glycerol can be added or another preserving composition comprising glycerol can be added subsequently. For example a biological buffer comprising glycerol can be added after the sperm cells preserving composition.

In an embodiment, the preserving composition, optionally the cholesterol: carrier complex or the sperm cells preserving composition is in powder or solution form. In an embodiment, the sperm cells preserving composition is in powder form.

In an embodiment, the preserving composition, such as the sperm cells preserving composition further comprises one or more of a cell permeable anti-oxidant peptide, a carbohydrate, a pH stabilizer, and/or an antibiotic optionally an antibiotic cocktail. In an embodiment, the cell permeable anti-oxidant peptide is added to any composition described herein.

In an embodiment, the preserving composition comprising cholesterol: carrier complex is formulated and/or added in an amount to provide a particular sperm cell/cholesterol: carrier complex ratio. Alternatively or in combination therewith the ejaculate and/or isolated sperm cells are diluted to provide the desired ratio. For example, the sperm cells to cholesterol: carrier ratio is in one embodiment, from about 25 million sperm cells per mg CC complex or PEG-C conjugate to about 100 million sperm cells per mg CC complex or PEG-C conjugate, optionally about 50 million sperm cells per mg CC complex. In an embodiment, the cholesterol: carrier sperm cells composition and/or the preserved sperm cells composition comprises sperm cells to CC complex ratio or a PEG-C conjugate ratio of from about 25 million sperm cells per mg CC complex or PEG-C conjugate to about 100 million sperm cells per mg CC complex or PEG-C conjugate, optionally about 50 million sperm cells per mg CC complex or PEG-C conjugate.

In an embodiment, sperm cells to CC complex ratio is from about 25 million sperm cells per mg CC complex to about 400 million sperm cells per mg CC complex, optionally about 50 million sperm cells per mg CC complex to about 200 million sperm cells per mg CC complex, optionally about 200 million sperm cells per mg CC complex. In an embodiment, the preserved sperm cells composition comprises sperm cells to CC complex ratio of from about 25 million sperm cells per mg CC complex to about 400 million sperm cells per mg CC complex, optionally about 50 million sperm cells per mg CC complex to about 200 million sperm cells per mg CC complex, optionally about 200 million sperm cells per mg CC complex.

The preserved sperm cells composition in a) can be kept at 4° C. for about 1 to about 9 days. In an embodiment, the preserved sperm cells composition in a) is kept at 4° C. for about 1 to about 9 days.

The ejaculate containing sperm cells can be mixed with a cholesterol: carrier complex and/or sperm cells preserving composition within less than or about 5 minutes after it is obtained from an animal, or the ejaculate containing sperm cells can be maintained in its own plasma from about 30 min to about 60 min, optionally at room temperature, optionally about 22°, optionally about 4° C. In an embodiment, the ejaculate containing sperm cells is mixed with a cholesterol: carrier complex and/or sperm cells preserving composition within less than or about 5 minutes after it is obtained from an animal. In an embodiment, the ejaculate containing sperm cells is mixed with a cholesterol: carrier complex and/or sperm cells preserving composition within from about 30 min to about 60 min after it is obtained from an animal, optionally at room temperature, optionally about 22°, optionally about 4° C.

The CC complex can be prepared for example as described in Example 1. PEG and PEG-cholesterol conjugates can be purchased for example from Sigma Aldrich Chemical Company. PEG-cholesterol conjugates can be generated for example using the DCC (N,N'-dicyclohexylcarbodiimide, DCC)/(4-dimethylaminopyridine, 4-DMAP) esterification method. The PEG moiety can also be added. For plant sterols, pegylated plant sterols can be produced for example by the reaction of the sterol hydroxyl with ethylene oxide.

In one embodiment, the cholesterol:cyclodextrin complex (CC complex) is at a concentration of at least 0.125 mg/ml of the preserving composition, the cholesterol: carrier complex sperm cell composition or the preserved sperm cells composition. In one embodiment, the CC complex is at least 0.125 mg/ml of the cholesterol: carrier complex sperm cell composition or the preserved sperm cells composition. In one embodiment, the CC complex is at least 0.125 mg/ml of the cholesterol: carrier complex sperm cell composition and/or the preserved sperm cells composition. In one embodiment, the CC complex is from about 0.25 mg/mL to about 0.5 mg/mL of the cholesterol: carrier complex sperm cell composition and/or the preserved sperm cells composition. In one embodiment, the CC complex is about 0.25 mg/mL of the cholesterol: carrier complex sperm cell composition and/or the preserved sperm cells composition. In one embodiment, the CC complex is about 0.5 mg/mL of the cholesterol: carrier complex sperm cell composition and/or the preserved sperm cells composition. In one embodiment, the cholesterol: carrier complex preservative composition or the sperm cells preserving composition comprises about or at least 0.125 mg/ml of a CC complex, optionally from about 0.25 mg/mL to about 0.5 mg/mL, optionally about 0.25 mg/mL, optionally about 0.5 mg/mL, and a biological buffer, is substantially free of animal phospholipid, animal protein, and/or animal lipoprotein, and is provided in a reconstituted solution. In an embodiment, the CC complex is in powder form prior to reconstitution or use.

The concentration and/or ratio of CC complex added to ejaculate and/or isolated sperm directly or provided in the preserving compositions such as in the sperm cells preserving compositions or after addition, for example in the preserved sperm cells composition is titrated. In one embodiment, the amount of CC complex is between about 0.125 mg/mL to about 10 mg/mL in the preserving composition, optionally the cholesterol: carrier complex preserving composition, the sperm cells preserving composition, or in the cholesterol: carrier sperm cells composition or in the preserved sperm cells composition, such as at least 0.125, 0.25, 0.375, 0.5, 0.675, 0.75, 0.875, or 1 mg/mL CC complex, and at most about 0.75, 0.875, 1, 1.5, 2, 2.5, 3, 3.5, 4, 4.5, 5, 5.5, 6, 6.5, 7, 7.5, 8, 8.5, 9, 9.5, or 10 mg/mL CC complex. In an embodiment, the amount of CC complex is between about 0.5 mg/mL to about 20 mg/mL, optionally 2 mg/mL. The concentration can be any 0.01 mg increment between 0.125 and 20 mg/L.

In one embodiment, the examples can be used to calculate suitable ratios can concentration. For example as shown in the Examples semen with sperm concentration of about 100 million per ml are exposed to about 0.5 mg/ml of CC complex preserving composition. After 15 min exposure at 22 C, the CC semen composition is diluted with TG extender (2×) providing a final concentration of CC of about 0.25 mg/ml and a sperm concentration of about 50 million/ml.

The CC complex can be made as a composition as described in Example 1 and used directly or added to a preserving composition comprising a cryoprotectant. In an embodiment, CC complex is prepared as described in Example 1 and the CC complex composition is added to the sperm cells preserving composition, in powder (e.g. the preservation solution is used to reconstitute the CC complex) or added in a solution form. In an embodiment, the CC complex is in powder form for example where the solvents used in its preparation such as methanol and chloroform, have been evaporated. In an embodiment, the CC complex is in solution form, optionally in solvent or reconstituted in a biological buffer such as Tris buffer.

In another embodiment, a composition described herein such as a preserving composition, optionally the sperm cells preserving composition further comprises one or more of a carbohydrate such as fructose, a pH stabilizer such as citric acid monohydrate and an antibiotic such as gentamycin, tylosin, or linco-spectin.

In one embodiment, the preserving composition comprises tris buffer, optionally about 3% (w/v), for example 3.03% (w/v), citric acid monohydrate optionally about about 1.74% (w/v), a carbohydrate source such as fructose for example at 1.24% (w/v) a cryoprotectant such as glycerol optionally between 0 and 22%, for example 14% (v/v) optionally with CC complex added or as a separate composition for example wherein the CC complex is at a concentration of about 0.5 mg/ml to about 2 mg/ml.

The methods as described herein can comprise sequential addition of various compositions. In some embodiments, the ejaculate and sperm are diluted prior to combination with a cholesterol: carrier complex preserving composition or a sperm cells preserving composition comprising cholesterol: carrier complex. They can also be diluted afterwards or combined with one or more preserving compositions or additives described herein.

For example the diluted ejaculate or sperm cells can be combined with a cholesterol: carrier complex, optionally a CC complex preserving composition and/or a PEG-C conjugate preserving composition, followed by preserving composition comprising a cryoprotectant and/or other components described herein.

Where the intent is to not freeze the semen or sperm a cryoprotectant can be omitted.

Accordingly, in one embodiment the method comprises:
a. combining an ejaculate containing sperm cells and/or isolated sperm cells with a preserving composition comprising a cholesterol:cyclodextrin complex (CC complex) and/or a PEG conjugated cholesterol (PEG-C conjugate) to provide a cholesterol carrier sperm cells composition;
b. combining the cholesterol carrier sperm cells composition with a preserving composition comprising a cryoprotectant, optionally glycerol, optionally a cell permeable anti-oxidant peptide, and a biological buffer to provide a preserved sperm cells composition; and
c. freezing the preserved sperm cells composition,
wherein the the preserving composition is substantially free of animal phospholipid, animal protein, and/or animal lipoprotein. In an embodiment, prior to or after combining ejaculate or isolated sperm cells with the sperm cells preserving composition, the ejaculate or the sperm cells composition is diluted in dilution solution to a selected sperm concentration.

In an embodiment, one or more of the method steps comprises incubating for less than about 15 min. The incubation can be for example any time between 5 and 15 minutes or between 10 and 15 minutes. The incubation can be performed at around room temperature for example from about from 20 to 25° C., optionally 22° C. One or more of the incubations for example step b can be performed in an environment at about from 20 to 25° C., optionally about 22° C., or at about from 0 to 10° C., optionally about 4° C.

In one embodiment, the method of preserving a semen or sperm cells comprises combining an ejaculate containing sperm cells with a preserving composition comprising a biological buffer, and a cholesterol:cyclodextrin complex (CC complex) and/or a PEG conjugated cholesterol (PEG-C conjugate). In an embodiment, the preserving composition further comprises glycerol, and/or a cell permeable anti-oxidant peptide, and/or a biological buffer. In an embodiment, the preserving composition is substantially free of animal phospholipid, animal protein, and/or animal lipoprotein. In an embodiment, the method comprises keeping the preserved sperm cells composition at about 4° C. for about 1 day to about 9 days after a step described herein, optionally step a), b), or c) above or after step i) or ii). In an embodiment, the method comprises freezing preserved sperm cells composition.

In an embodiment, the cell permeable anti-oxidant peptide is added to any step in the methods described herein. In an embodiment, the cell permeable anti-oxidant peptide is added any composition described herein or preserving composition for semen. The composition may be at room temperature for example at about 22° C. or warmed for example to about 37° C. In an embodiment, the composition comprising the CPP is warmed to a temperature at or between about 30-39° C. In an embodiment, the cell permeable anti-oxidant peptide is added to any composition described herein at about 20° C., at about 21° C., about 22° C., about 23 C, about 24 C, about 25, about 26, about 27. about 28, about 29, about 30, about 31, about 32, about 33, about 34, about 35, about 36, about 37, about 38, about 39 or about 40 C. In one embodiment, the cell permeable anti-oxidant peptide (also referred to as CPP herein) is provided in a sperm cell preserving composition comprising CC complex and a tris glycerol buffer that is warmed to about 37° C.

In one embodiment, prior to and/or after combining ejaculate or the sperm cells with a preserving composition such as the cholesterol: carrier complex preserving composition or the sperm cells preserving composition, the ejaculate or the sperm cells or combination e.g. combined ejaculate: sperm cells preserving solution, is diluted in dilution solution to a selected sperm concentration. In an embodiment, the sperm concentration is from about 25 million cells/mL to about 100 million cells/mL, optionally about 50 million cells/mL.

In one embodiment, the amount of glycerol in the sperm cells preserving composition is more than 0% (v/v), for example between about 1% and 40% (v/v), between about 2% and 22% (v/v), or between about 4% and 22% (v/v). The concentration of glycerol can vary and can amended to provide a desired final concentration upon dilution with the ejaculate and/or sperm cells (or diluted ejaculate and/or sperm cells). In another embodiment, the amount of glycerol in the preserved sperm cells composition is more than 0% (v/v), between about 1% and 11% (v/v), between about 2% and 11% (v/v), between about 3% and 11% (v/v), between about 5% and 11% (v/v), or between about 5% and 7% (v/v). The amount of glycerol can for example be about 2%, about 3%, about 4%, about 5%, about 6%, about 7%, about 8%, about 9%, about 10% or about 11% or any range therebetween, such as about 1 to 11%, or 3 to about 7%.

In another embodiment, the cholesterol: carrier or the sperm cells preserving composition, or the preserved sperm cells composition, comprises between about 0.125 mg/mL to about 10 mg/ml cholesterol:cyclodextrin complex, preferably between about 0.5 mg/mL to about 2 mg/mL, optionally 1 mg/mL.

In an embodiment, from about 0.25 mg to about 10 mg or from about 0.5 to about 2 mg of CC complex, optionally 1 mg CC complex is added per ml of ejaculate. In an embodiment, the ejaculate is diluted in a biological buffer to 100 million sperm per mL. In an embodiment, from about 0.25 mg CC complex to 1 mg CC complex is added per 100 million sperm per ml. In an embodiment, about 0.5 mg CC complex is added per 100 million sperm per ml.

Plant cholesterol or phytosterol, which is a plant sterol, is shown herein to be functionally redundant with animal cholesterol in regard to maintaining membrane structural integrity and fluidity of bull semen. Plant cholesterol or phytosterol can substitute for animal cholesterol in CC complex in a cholesterol: carrier complex preserving composition or in a sperm cells preserving composition, or in a preserved sperm cells composition. In an embodiment, the cholesterol is plant cholesterol or a plant sterol, optionally a phytosterol, or a stanol, or a combination thereof. In an embodiment, a phytosterol is selected from the group consisting of beta-sitosterol, campesterol, stigmasterol, and Phytocol, or combination thereof. In an embodiment, the phytosterol is beta-sitosterol, In an embodiment, the phytosterol is campesterol. In an embodiment, the phytosterol is stigmasterol. In an embodiment, the phytosterol is Phytocol. The plant cholesterol may be extracted from plants but may also be from a synthetic source, and it may be modified or contain other components. In an embodiment, the plant cholesterol or the phytosterol is from peanuts, flaxseeds, nuts, avocados, and/or hemp seeds, a modified form thereof, or from a synthetic source, or a combination thereof.

Plant cholesterol is commercially available for example PhytoChol, (Wilshire Technologies, NJ). In an embodiment, the plant cholesterol is PhytoChol.

Cyclodextrin is an integral part of the CC complex. In an embodiment the cyclodextrin comprises or is selected from the group consisting of α-cyclodextrin, β-cyclodextrin, γ-cyclodextrin, methyl-α-cyclodextrin, methyl-β-cyclodextrin, methyl-γ-cyclodextrin, and hydroxypropyl-beta-cyclodextrin. In an embodiment the cyclodextrin is α-cyclodextrin, β-cyclodextrin, γ-cyclodextrin, methyl-α-cyclodextrin, methyl-β-cyclodextrin, methyl-γ-cyclodextrin, or hydroxypropyl-beta-cyclodextrin, or a combination thereof. In an embodiment, the cyclodextrin comprises or is methyl β-cyclodextrin. In an embodiment, the cyclodextrin comprises or is hydroxypropyl-beta-cyclodextrin.

The ratio of cholesterol to cyclodextrin can vary. In an embodiment, the ratio by weight of cholesterol to cyclodextrin in a cholesterol:cyclodextrin complex is about or at least 1:100, 2:100, 3:100, 4:100, 5:100, 6:100, 7:100, 8:100, 9:100, 10:100, 11:100, 12:100, 13:100, 14:100, 15:100, 16:100, 17:100, 18:100, 19:100, 20:100, 21:100, 22:100, 23:100, 24:100, 25:100, 26:100, 27:100, 28:100, 29:100, or 30:100, optionally about or at least 9:100 or 20:100, preferably about or at least 9:100. For example, the ratio by weight of cholesterol to cyclodextrin can be a range or a specific ratio. The range can be any range between 1:100 to 30:100, including for example any 0.1 increment such as a range of 1.1 to 100 or 1 to 29.9. Similarly, a specific ratio can be any 0.1 increment between and including 1:100 and 30:100. In a specific embodiment, the ratio by weight of cholesterol to cyclodextrin is about 9:100.

In another embodiment, the molar ratio of cholesterol to cyclodextrin in a cholesterol:cyclodextrin complex is between 0.05 to 1, such as at least or about 0.05, 0.10, 0.15, 0.2, 0.25, 0.3, 0.35, 0.4, 0.45 and at most 0.3, 0.35, 0.4, 0.45, 0.5, 0.55, 0.6, 0.65, 0.7, 0.75, 0.8, 0.85, 0.9, 0.95, or 1. For example, the molar ratio of cholesterol to cyclodextrin can be a range or a specific ratio. The range can be any range between 0.05 to 1, including for example any 0.01 increment such as a range of 0.06 to 1 or 0.05 to 0.99. Similarly, a specific ratio can be any 0.01 increment between and including 0.05 and 1.

For example, the ratio by weight of cholesterol to methyl β-cyclodextrin in a cholesterol:cyclodextrin complex by weight is about or at least 1:100, 2:100, 3:100, 4:100, 5:100, 6:100, 7:100, 8:100, 9:100, 10:100, 11:100, 12:100, 13:100, 14:100, 15:100, 16:100, 17:100, 18:100, 19:100, 20:100, 21:100, 22:100, 23:100, 24:100, 25:100, 26:100, 27:100, 28:100, 29:100, or 30:100, optionally about or at least 9:100 or 20:100, preferably about or at least 9:100. In another embodiment, the molar ratio of cholesterol to methyl β-cyclodextrin in a cholesterol:cyclodextrin complex is between 0.05 to 1, such as at least 0.05, 0.10, 0.15, 0.2, 0.25, 0.3, 0.35, 0.4, 0.45 and at most 0.3, 0.35, 0.4, 0.45, 0.5, 0.55, 0.6, 0.65, 0.7, 0.75, 0.8, 0.85, 0.9, 0.95, or 1. In a specific embodiment, the ratio by weight of cholesterol to methyl β-cyclodextrin is about 9:100.

The freezing of the semen or sperm cells can be carried out according to a freezing curve. For example, semen packaged in a French straw can be frozen to −80° C. in a programmable cell freezer such as ICE-CUBE 14-S, Sy-Lab Version 1.30, Gerate GmbH, Neupurkdersdof, Austria using a freezing curve as reported in Anzar et al. 2011. For example, in the cell freezer, semen filled French straws can be cooled from +4° C. to −10° C.@−3° C. min$^{-1}$, and from −10° C. to −80° C.@−40° C. min$^{-1}$. In an embodiment, the method of freezing semen or sperm cells comprises a use or a method according to a freezing curve described in Example 4. In an embodiment, the method of freezing semen or sperm cells comprises a use or a method according to Anzar et al, 2011. In an embodiment, semen or sperm cells packaged in a French straw is frozen to about −80° C. in a programmable cell freezer. In an embodiment, the freezer is ICE-CUBE 14-S, Sy-Lab Version 1.30 or like freezer. In an embodiment, semen or sperm cells filled French straws is cooled from +4° C. to −10° C.@−3° C. min$^{-1}$, and from −10° C. to −80° C.@−40° C. min$^{-1}$.

After one or more of the steps such as after the step of combining ejaculate with a composition described herein such as the cholesterol: carrier complex preserving composition, the sperm cells preserving composition, and/or after adding a biological buffer, and/or a cryoprotectant, optionally glycerol, and/or a carbohydrate, and/or a pH stabilizer, and/or a cell permeable anti-oxidant peptide in one or more steps or preserving compositions, diluting the ejaculate in dilution solution to a selected sperm concentration, the composition comprising ejaculate may be subjected to one or more cooling steps prior to freezing as part of a freezing method.

An accelerated freezing method as described herein can also be employed. The accelerated cooling freezing method can be used with various preserving compositions Conventionally, the cooling steps would be protracted and/or require the use of a cold room. In the absence of using egg yolk, the preservation method can be accelerated. For example, as shown in Table 2, the conventional protocol using egg yolk would take greater than 2 hrs to complete. Using CC complex instead, an accelerated freezing protocol is possible. For example, cooling ejaculate according to the accelerated protocol shown can be completed in about 35 min.

In one embodiment, the ejaculate is cooled to room temperate prior to or after combining with a preserving composition or dilution solution. In some embodiments, the ejaculate is diluted with dilution solution and/or combined with one or more preserving composition(s) then cooled to about room temperature. This cooling step can take for example about 10-30 minutes. Longer times can also be used if convenient. The preserving composition such as the cholesterol: carrier complex preserving composition or the sperm cells preserving composition can be added before or after cooling to 22° C. or cooling to 10° C. In some embodiments, cooling from about 37 C to about 22 C is accomplished in approximately 15 min, for example at a rate of about 0.5-2° C. per/minute.

In some embodiments, after cooling to about room temperature, the composition comprising ejaculate is cooled to 10° C. according at a rate of about 0.5-2° C. per/minute prior to freezing for example in liquid nitrogen. The timed cooling can be accomplished using a programmable freezing apparatus. In another embodiment, the composition cooled to 10° C., is then cooled to −80° C. optionally at a rate of about 30° C. to 60° C./min, for example about 40° C./min, by optionally using a programmable freezing apparatus (e.g. a programmable freezer). In yet other embodiments, after cooling to about room temperature, the composition comprising the composition comprising ejaculate is frozen, by directly placing the composition in liquid nitrogen.

In an embodiment, the accelerated freezing method outlined in Table 2 is used. The incubation times that are stipulated can range from about 20% less of each stipulated time. Longer times can also be used, for example up to 50% longer.

In the present disclosure, each of the steps is carried out without the need of the use of a 4° C. cold room. In an embodiment, each of the steps is performed above 10° C., above 15° C., above 20° C., or at or above room temperature prior to freezing for example in liquid nitrogen. In another embodiment, each of the steps is performed below 40° C. Any temperature, between 10° C. and 40° C., preferably below 27° C. can be used.

In addition to cooling steps, one or more of the steps can include an incubation, for example after addition of a the cholesterol: carrier complex preserving composition or the sperm cells preserving compositions, the composition comprising ejaculate may be incubated for a length of time, optionally about or at least 5 min to about or up to 30 min, optionally about or up to 15 min. In an embodiment, the composition comprising ejaculate is incubated for about or at least 5 min to about or up to 30 min, optionally about or up to 15 min. The incubation can take place at a temperature between from about 4 to about 37° C., or any temperature or range therebetween.

In an embodiment, the method comprises one or more or all of the steps of the method shown in FIG. 1 (right side).

In an embodiment, the ejaculate is diluted using a warm dilution solution, optionally having a temperature of about 32, 33, 34, 35, 36, or 37° C., to a selected sperm concentration and optionally cooled to about room temperature, optionally to about 18, 19, 20, 21, 22, 23, or 24° C., prior to combining ejaculate with the cholesterol: carrier complex preserving composition or the sperm cells preserving composition.

In another embodiment, prior to freezing, the preserved sperm cells composition is packaged in a straw.

In an embodiment, the steps further comprise thawing the preserved sperm cells composition. In an embodiment, the preserved sperm cells composition is thawed at 37° C. for about 60 sec, or at least 60 sec, prior to use or preparation for use.

The skilled person can readily recognize that the methods and compositions described herein can be used on ejaculate or sperm cells from a variety of sexual animals. In an embodiment, the ejaculate is from a mammal, optionally an ungulate, such as a livestock ungulate or a domesticated ungulate, optionally a ruminant, stallion or boar. In a further embodiment, the ungulate is a bull or bison.

Also provided are compositions. In an embodiment, the composition is a cholesterol: carrier complex preserving composition or a sperm cells preserving composition with or without ejaculate and/or isolated sperm cells comprising about at least 0.125 mg/ml of a cholesterol:cyclodextrin complex (CC complex) and a biological buffer, and substantially free of animal phospholipid, animal protein, and/or animal lipoprotein. In an embodiment, the amount of CC complex in the composition is about 0.125 mg/mL to about 10 mg/mL in the sperm cells preserving composition, such as at least 0.125, 0.25, 0.375, 0.5, 0.675, 0.75, 0.875, or 1 mg/mL CC complex, and at most about 0.75, 0.875, 1, 1.5, 2, 2.5, 3, 3.5, 4, 4.5, 5, 5.5, 6, 6.5, 7, 7.5, 8, 8.5, 9, 9.5, or 10 mg/mL CC complex. In a specific embodiment, the amount of CC complex is between about 0.5 mg/mL to about 1 mg/mL of the cholesterol: carrier complex preserving composition or the sperm cells preserving composition.

In an embodiment, the cholesterol: carrier complex preserving composition or the sperm cells preserving composition comprises a cholesterol that is a plant cholesterol. In another embodiment, the cholesterol is animal cholesterol. In yet another embodiment, the cholesterol is a combination of animal and plant cholesterol. In another embodiment, the carrier is a cyclodextrin for example a cyclodextrin described herein, such as methyl β-cyclodextrin. In another embodiment, the cyclodextrin is hydroxypropyl-β-cyclodextrin.

The present disclosure also provides for methods using and compositions comprising cell-permeable anti-oxidant peptides. It is demonstrated herein, that cell-permeable anti-oxidant peptides can protect sperm from damage involving reactive oxygen species (ROS). In an embodiment, the composition, optionally the cholesterol: carrier complex preserving composition or the sperm cells preserving composition comprises a cell permeable anti-oxidant peptide. In an embodiment, the cell permeable anti-oxidant peptide is SS31, or a variant or derivative thereof. In an embodiment, the cell permeable anti-oxidant peptide is mTP4, or a variant or derivative thereof. In an embodiment, the cell permeable anti-oxidant peptide plays physiological roles in sperm cells health and viability. In an embodiment, the cell permeable anti-oxidant peptide is in anhydrous, powder, resuspension or solution form. In an embodiment, the cell permeable anti-oxidant peptide is in anhydrous form. In an embodiment, the cell permeable anti-oxidant peptide is in powder form. In an embodiment, the cell permeable anti-oxidant peptide is in resuspension form. In an embodiment, the cell permeable anti-oxidant peptide is in solution form and is added to the composition.

In this disclosure, the damage to mammalian sperm was prevented using cell-penetrating peptides (DMT-SS31 and DMT-mTP4, hereafter called SS31 and mTP4). As shown herein, the post-thaw longevity of cryopreserved bovine sperm was improved when using cell permeating anti-oxidant peptides (SS31 and mTP4). Accordingly, the cell permeating antioxidant peptides can be used in any of the compositions or methods described and may also be used to improve sperm parameters during cryopreservation in the absence of cholesterol carrier. Accordingly also provided in one aspect, is a preserving composition comprising a cell permeable antioxidant peptide. Further, also provided in another aspect is a method of comprising providing a preserving solution comprising a cell permeable antioxidant peptide.

In one embodiment, the cell-penetrating peptide is DMT-SS31. In another embodiment, the cell-penetrating peptide is DMT-mTP4. A combination can also be used.

The concentration of the cell permeable antioxidant peptide is for example 5-30 micromolar for every about 25 to 75 million sperm. For example as described in the Examples, 0.5 µM SS31 or mTP4 was added per ml semen containing about 50 million sperm. A concentration of 20 µM SS31 or mTP4 per ml of semen containing 50 million sperm was also used in other experiments.

Also provided is a composition comprising ejaculate and/or isolated sperm cells and a preserving composition described herein, optionally a cholesterol: carrier complex preserving composition and/or a sperm cells preserving composition described herein. The composition is optionally frozen, optionally in a straw or other container, such as a sterile vial or sterile tube, optionally in an individual dosage form or a multi-individual dosage form. The composition for example can be comprised in a container where the temperature is maintained below 0° C., for example in a shipping container or package comprising liquid nitrogen or dry ice.

In an embodiment, the semen or sperm cells are centrifuged to concentrate the semen or the sperm cells. In an embodiment, the semen or sperms are sorted for X-chromosome and Y-chromosome bearing sperm by cell sorter and isolated to provide isolated sperm cells.

The number of sperm per dose is relevant in artificial insemination. In an embodiment, the compositions are packaged in individual doses, optionally in straws. In another embodiment, the compositions are packaged as multi-individual doses, for example a multiple of an individual dosage form.

In a further embodiment, there is provided in an individual dosage form comprising at least or about 1 000 000, 2 000 000, 3 000 000, 4 000 000, 5 000 000, 6 000 000, 7 000 000, 8 000 000, 9 000 000, or 10 000 000 sperm/dose in a preserving composition. The number of sperm per dose in a preserving composition can also be up to 25-30 million or any number between 1 million and 30 million. In an embodiment, the number of sperm per dose in a preserving composition is up to about 30 million, or any number between 1 million and 30 million.

Figure 7:
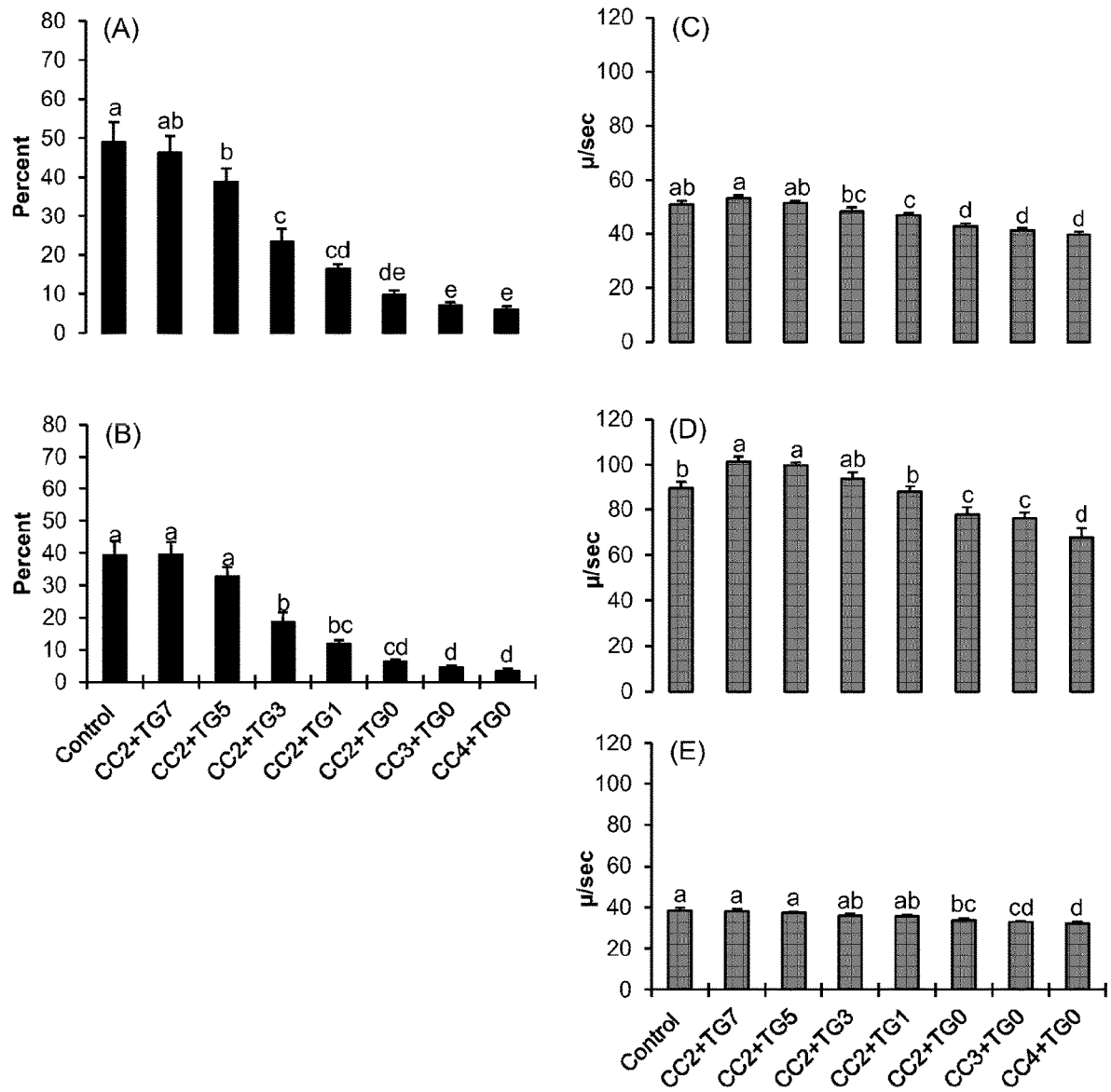
FIGS. 7A to 7E are a plurality of graphs depicting sperm properties post thaw.
Figure 8:
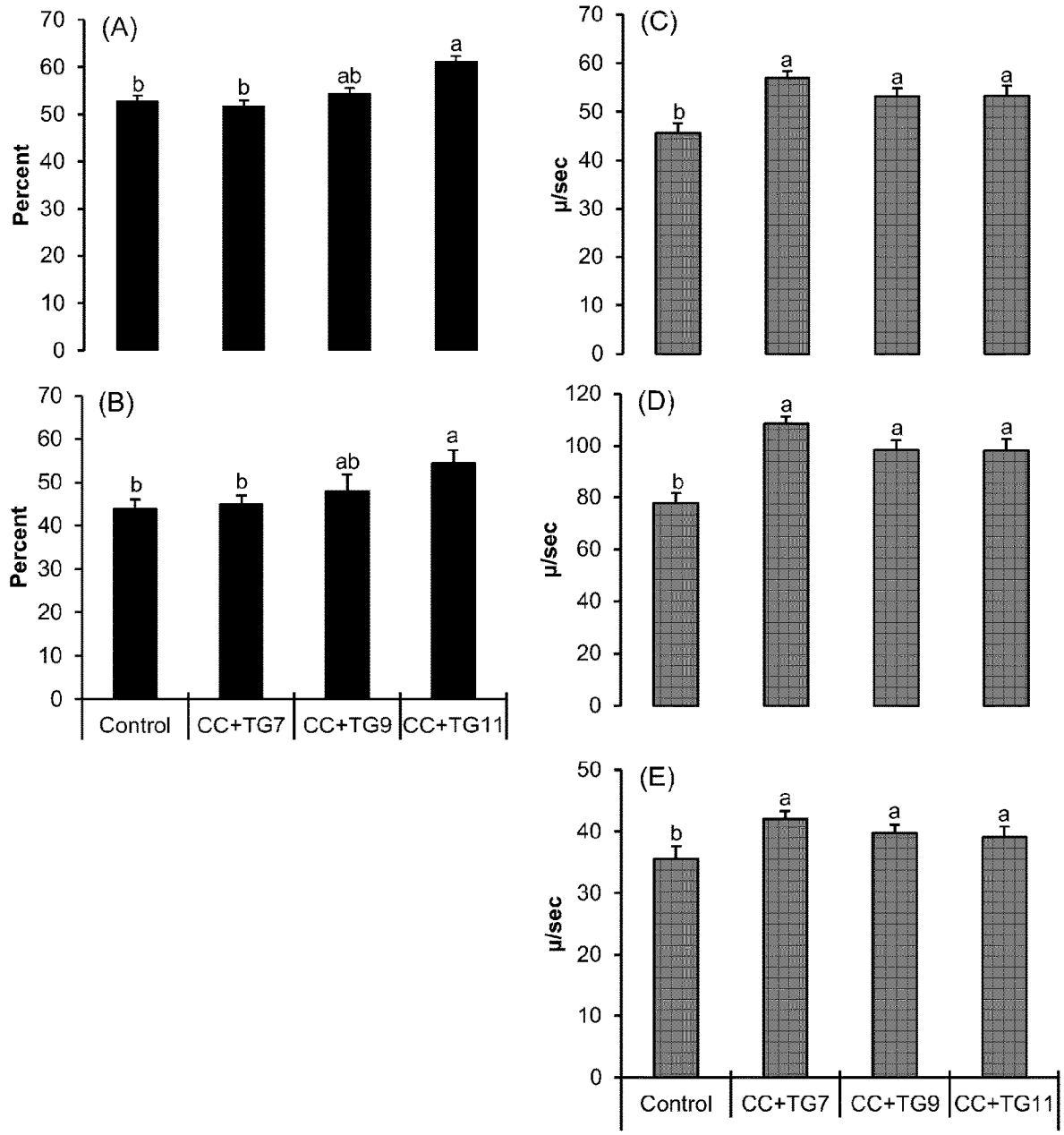
FIGS. 8A to 8E are a plurality of graphs depicting post-thaw sperm characteristics.

The quality of post-thawed sperms can be assessed by motion and structural characteristics, for example, by measuring sperm such as total and progressive motility, velocity such as average path, curvilinear, and straight line velocity, and integrities such as plasma membrane (PM) and acrosome (AR) integrities, for example as described in Examples 4 and 5. Total motility refers to % of all moving sperms. Progressive motility refers to % of all sperms moving in straight line. Average path, curvilinear, and straight line velocity of sperms as presented as $\mu m\ sec^{-1}$. These motility and velocity parameter can be assessed using Computer Assisted Semen Analysis (CASA) for example, SpermVision 3.5, Minitube (Ingersoll, Ontario, Canada) as described in Anzar et al. 2011). As described, post-thawed sperms using methods and compositions for freezing sperms described in Examples 4 and 5 were assessed for total motility and progressive motility as well as various velocity parameters. As shown for example in FIGS. 7 and 8, semen preserved using preserving compositions comprising CC complex had comparable or better sperm parameters. Post-thawed sperms from methods and compositions for freezing sperms described in the Examples provided herein have average path velocity of at least 20 $\mu m\ sec^{-1}$, or between about 20 and 120 $\mu m\ sec^{-1}$. It is also shown post-thawed sperms from methods and compositions for freezing sperms described in the Examples provided herein have curvilinear velocity of at least 20 $\mu m\ sec^{-1}$, or between about 20 and 150 $\mu m\ sec^{-1}$. In an embodiment, post-thawed sperms from methods and compositions for freezing sperms described in the Examples provided herein have straight line velocity of at least 20 um $sec^{-1}$, or between about 20 and 120 $\mu m\ sec^{-1}$. In some embodiments, the method further comprises assessing one or more sperm parameters, for example testing a dosage for one or more sperm parameters optionally selected from total motility, progressive motility, average path velocity, curvilinear velocity, and/or straight line velocity. In an embodiment, the total motility, progressive motility, average path velocity, curvilinear velocity, and/or straight line velocity is measured by CASA, optionally SpermVision 3.5.

Structural characteristics of post-thawed sperms such as plasma membrane (PM) and acrosome (AR) integrities can be analyzed by a flow cytometer, for example, Partec Cyflow Space, version 2.4 by Partec GmbH (Munster, Germany), for example, equipped with argon laser, for example, 400 mW argon laser, for example as described in Examples 4 and 5. After thawing, fluorescent dyes such as fluorescein isothiocyanate-peanut agglutinin (FITC-PNA; Sigma chemicals, St. Louis, MO; stock 1 mg $mL^{-1}$ in PBS) and propidium iodide (PI; Invitrogen) are added to the semen, incubated for, for example, 10 min at 37° C. Sperms in each sample are fixed by adding, for example, 10 µL of 10% formaldehyde and analyzed within a few hours. FITC-PNA and PI are excited with, for example, 488 nm blue laser and their fluorescent data are recorded with photo multiplier detectors FL-1 and FL-3, respectively (see Anzar et al. 2011) after gating sperm population with forward and side scatters. Sperms with intact PM and AR excluded PI and FITC-PNA, whereas sperms with compromised PM and AR stained red (PI) and green (FITC), respectively. As demonstrated herein, plasma membrane (PM) and/or acrosome (AR) integrities of post-thawed sperms can be measured using a flow cytometer, optionally Partec Cyflow Space. In an embodiment, post-thawed sperms from methods and compositions for freezing sperms described in the Examples provided herein have the same or less than about 20%, less than about 18%, less than about 16%, less than about 14%, less than about 12%, or less than about 11% decline in sperm with intact plasma membrane and intact acrosomes (IPM-IAR).

The quality of post-thawed sperms can be assessed by insemination rate of these sperms in a female animal. In some methods, the method further comprising inseminating a female animal.

The insemination protocol can be any acceptable protocol, for example, the one described in Example 2, in synchronized and non-synchronized cows or other animals.

As demonstrated in the Examples, post-thawed sperms from methods and compositions for freezing sperms described in the Examples provided herein provides sperms with same or higher fertility rate than a conventional semen extender for example using egg yolk or milk proteins in an animal, optionally a cow.

In an embodiment, the animal is a cow. In an embodiment, post-thawed sperms from methods and compositions for freezing sperms described in the Examples provided herein provides sperms with pregnancy rate of at least 30%, 35%, 40%, 45%, 50%, 55%, 60%, 65%, 70%, 75%, 80%, 85%, 90%, 95%, or 100%. In an embodiment, post-thawed sperms from methods and compositions for freezing sperms described in the Examples provided herein provides sperms with pregnancy rate of at least 30%, 35%, 40%, 45%, 50%, 55%, 60%, 65%, 70%, 75%, 80%, 85%, 90%, 95%, or 100%. In an embodiment, post-thawed sperms from methods and compositions for freezing sperms described in the Examples provided herein provides sperms with pregnancy rate of between about 30% and 100%.

As mentioned, the methods and compositions described in the Examples provided herein allow for rapid or accelerated freezing of semen without or with minimal adverse effects to the sperms.

In an aspect, also provided is a method of accelerated freezing of semen or sperm cells comprising,
 a. combining an ejaculate containing sperm cells and/or isolated sperm cells with
  i. a cholesterol: carrier complex preserving composition to provide a cholesterol: carrier sperm cells composition and cooling to room temperature prior to or after combining with the cholesterol: carrier complex preserving composition, optionally incubating for about 10-15 min,
  ii. combining the cholesterol: carrier sperm cells composition with a sperm cells preserving composition comprising a cryoprotectant and/or a carbohydrate, and a biological buffer to provide a preserved sperm cells composition and cooling to about 10° C. or about 4° C. at a rate of temperature drop of about 0.5-2° C. per/minute, prior to or after combining with the sperm cells preserving composition; or
  i. a sperm cells preserving composition comprising a cholesterol carrier complex, a cryoprotectant and/or a carbohydrate, and a biological buffer to provide a preserved sperm cells composition and cooling to room temperature prior to or after combining with the sperm cells preserving composition, optionally incubating for about 10-15 min, cooling to about 10° C. or about 4° C. at a rate of temperature drop of about 0.5-2° C. per/minute, after combining with the sperm cells preserving composition;
 b. cooling the preserved sperm cells composition to about or less than −80 C at a rate of temperature drop of about −20° C./min to about −60° C./min; optionally further cooling the preserved sperm cells composition, for example by inserting the composition in liquid nitrogen.
wherein the cholesterol: carrier complex preserving composition and/or the sperm cells preserving compositions is/are substantially free of animal phospholipid, animal protein, and/or animal lipoprotein, for example free of animal source ingredients.

Alternatively, also provided is a method of accelerated freezing of semen or sperm cells comprising,
 a. cooling an ejaculate containing sperm cells and/or isolated sperm cells to room temperature,
 b. combining an ejaculate containing sperm cells and/or isolated sperm cells with
  i. a cholesterol: carrier complex preserving composition to provide a cholesterol: carrier sperm cells composition and, optionally incubating for about 10-15 min,
  ii. combining the cholesterol: carrier sperm cells composition with a sperm cells preserving composition comprising a cryoprotectant and/or a carbohydrate, and a biological buffer to provide a preserved sperm cells composition; or
  i. with a sperm cells preserving composition comprising a cholesterol carrier complex, a cryoprotectant and/or a carbohydrate, and a biological buffer to provide a preserved sperm cells composition, optionally incubating for about 10-15 min,
 c. freezing the preserved sperm cells composition, optionally cooling to about 10° C. or about 4° C. at a rate of temperature drop of about 0.5-2° C. per/minute, after combining with the sperm cells preserving composition, cooling the preserved sperm cells composition to about or less than −80C at a rate of temperature drop of about −20° C./min to about −60° C./min; optionally further cooling the preserved sperm cells composition, for example by inserting the composition in liquid nitrogen;
wherein the cholesterol: carrier complex and/or the sperm cells preserving composition is substantially free of animal phospholipid, animal protein, and/or animal lipoprotein, for example free of animal source ingredients.

In an embodiment, the accelerated freezing method is as described in the Examples. In an embodiment, the method comprises packaging the preserved sperm composition, optionally in a straw, optionally prior to or after cooling to about 10° C. or about 4° C.

The methods for accelerated freezing described herein use a preserving composition comprising any cholesterol: carrier complex, any cryoprotectant, any carbohydrate, and/or any biological buffer, at any amount, concentration and/or ratio described herein. The methods may further utilize compositions that comprise any cell permeable anti-oxidant peptide, any pH stabilizer, any antibiotic or antibiotic cocktail, at any amount, concentration, and/or ratio described herein. The methods may be used with sperm cells of any animal, at any concentration and/or ratio with any component in any composition described herein. The methods comprise any freezing instrument, protocol, freezing rate described herein.

In an embodiment, the freezing is programmable freezing or vapor freezing. In an embodiment, the programmable freezing is a drop in temperature of about a rate of about 20° C./min, about 30° C./min, about 40° C./min, about 50° C./min or about 60° C./min. In an embodiment, the freezing is to about from −80° C. to −196° C.

In an embodiment, the accelerated method comprises a total time to freezing sperm from about 37° C. or above room temperature to about or less than −80° C. in less than about 60 min, about 55 min, about 50 min, about 45 min, about 40 min, about 35 min, or about 30 min.

For example as demonstrated herein, the methods and compositions for freezing sperms described in the Examples freezes sperms in between about 30 min and 45 min.

In an embodiment, the methods and compositions for freezing sperms described herein provided herein freezes sperms in less than 45 min or 35 min, comprises a preserving composition described herein, wherein the preserving composition is substantially free of animal phospholipid, animal protein, and/or animal lipoprotein, for example free of animal source ingredients.

In an embodiment, the freezing method used is vapor freezing. In another embodiment, the freezing method used is programmable freezer freezing In an embodiment, the vapor is nitrogen vapor.

In another aspect, the cell permeable anti-oxidant peptides described herein can be used to prevent sperm cell death, used optionally in the absence of a cholesterol: carrier complex.

Accordingly, also provided is a method of preventing sperm cell death comprising combining an ejaculate containing sperm cells and/or isolated sperm cells with a cell permeable anti-oxidant peptide to provide a protected sperm cells composition, wherein the protected sperm cells composition is substantially free of a cholesterol: carrier complex.

In an embodiment, the cell permeable anti-oxidant peptide comprises SS31 and/or mTP4. In an embodiment, the cell permeable anti-oxidant peptide is at any concentration described herein. In an embodiment, the cell permeable anti-oxidant peptide is at a concentration sufficient to improve post-thaw quality and/or longevity of cryopreserved sperm cells, optionally by at least 10%, at least 20% or greater. In an embodiment, improvement of post-thaw quality and/or longevity is assessed by any motion and structural characteristics described herein, measured by any methods and techniques described herein. The present disclosure furthermore provides a kit or package comprising one or more of a preserving composition such as a cholesterol: carrier complex preserving composition, a sperm cells preserving composition comprising a cholesterol:cyclodextrin complex (CC complex) or a PEC-C conjugate and a biological buffer, with the any of the compositions optionally comprising one or more of a cryoprotectant, optionally glycerol, a carbohydrate, a pH stabilizer, an antibiotic or antibiotic cocktail, and a cell permeable anti-oxidant peptide, each as described herein.

In an embodiment, the kit further comprises a one or more straws such as French straws for packaging preserved ejaculate.

The methods and products can be used for artificial insemination. Semen preserved using cholesterol (e.g. without egg yolk or milk) can be used for artificial insemination for example in synchronized and non-synchronized animals such as cows.

The following non-limiting Examples are illustrative of the present disclosure:

EXAMPLES

Example 1

Preparation of Tris Buffer & Extenders
1) Tris-citric acid buffer (TB) was prepared by dissolving tris 3.03% (w/v), citric acid monohydrate 1.74% (w/v) and fructose 1.24% (w/v) in Milli-Q distilled water. 2) Tris citric acid-egg yolk-glycerol (TEYG) extender contained egg yolk 40% (v/v), glycerol 14% (v/v) in TB. 3) Tris-glycerol extender (TG) contained glycerol 14% (v/v) in TB. Both TEYG and TG extenders contained gentamycin (500 ug/mL), tylan (100 ul/mL) and linco-spectin (300/600 µg/ml). The extenders TEYG and TG were centrifuged at 12000×g for 15 min at 4° C. The supernatant was stored at −20° C. and thawed at 37° C. before use. The TEYG and TG buffers as prepared are double strength (2×).

Preparation of Cholesterol: Cyclodextrin (CC) Complex

Cholesterol (SIGMA) and methyl β-cyclodextrin (SIGMA) complex was prepared, according to the procedure described by Purdy and Graham (2004). Solution 'A' was prepared by dissolving 200 mg cholesterol (Cat. C8667, Sigma, CAS Number 57-88-5) in 1 ml of chloroform, in a glass tube. In a separate glass tube, solution 'B' was prepared by dissolving 1 g methyl β-cyclodextrin (Cat. C4555, Sigma, CAS Number 128446-36-6) in 2 ml methanol. A 0.45 ml from solution 'A' (i.e. containing 90 mg cholesterol) was added to the solution 'B', stirred well until the solution became homogenous. The mixture was poured into a glass petri dish and the solvent was slowly dried with nitrogen gas. The crystals were further dried in desiccator overnight and stored at 22° C. in a glass container until used. On the day of experiment, a working solution was prepared by dissolving 50 mg cholesterol:cyclodextrin complex (CC complex) in Tris buffer at 37° C. or 22° C. and vortexed gently.

Semen Collection and Initial Evaluation

Semen was collected twice a week from 4 beef bulls, stationed at Goodale Research Farm, with an electro-ejaculator (Pulsator W, Lane Manufacturing Denver, CO, USA) according to Animal Use Protocol approved by Animal Care Committee, University of Saskatchewan, Saskatoon. Semen was transported to the Cryobiology Lab at University of Saskatchewan, Saskatoon, in a mobile incubator (37° C.) within 1 hour. Semen ejaculates were initially evaluated with computer-assisted sperm analyzer (CASA; SpermVision 3.5, Minitube, Ingersoll, Ontario, Canada). The semen ejaculates with sperm motility >60% and concentration >200×$10^6$/mL were selected for further processing.

Cryopreservation of Semen without Exogenous Protein (Egg Yolk)

The outline of this experiment is presented in FIG. 1. After initial evaluation, fresh semen was divided into two aliquots. Semen in aliquot 1 was diluted to 50×$10^6$ mL$^{-1}$ in conventional TEYG extender (control semen), and cooled and kept in water bath at 22° C. Aliquot 1 was, slowly cooled to 4° C. and frozen as described below. Semen in aliquot 2 was diluted to 100×$10^6$ sperm mL$^{-1}$ with TB at 37° C. and cooled to 22° C. After reaching 22° C., semen was first treated with exogenous cholesterol in CC (0 or 2 mg mL$^{-1}$)

at 22° C. for 15 min, and then divided into two sub-aliquots. The semen in sub-aliquot 2.1 was diluted to 50×106 mL$^{-1}$ in TG (without egg yolk) extender at 22° C., slowly cooled to 4° C. and frozen as described below. The semen in sub-aliquot 2.2 was first slowly cooled to 4° C. and then diluted in TG (without egg yolk) extender at 4° C. to final sperm concentration 50×10$^6$ mL$^{-1}$.

Aliquots 1, 2.1 and 2.2 were slowly cooled by placing semen tubes in 500 ml beaker containing water (22° C.) and shifted to walk-in cold room (4° C.). After cooling to 4° C. in 90-100 min, semen was packaged in 0.5 ml French straws. Semen straws were frozen to −80° C. in a programmable cell freezer (ICE-CUBE 14-S, Sy-Lab Version 1.30, Gerate GmbH, Neupurkdersdof, Austria) using freezing curve reported earlier (Anzar et al. 2011) with little modification. In cell freezer, semen straws were cooled from +4° C. to −10° C.@−3° C. min$^{-1}$, and from −10° C. to −80° C.@−40° C. min$^{-1}$. After reaching −80° C., semen straws were plunged in liquid nitrogen and stored for at least 24 h. Three straws per sample per bull were thawed in a water bath at 37° C. for about 60 sec, and pooled. Post-thaw motility characteristics were evaluated using Computer Assisted Semen Analysis (CASA).

As shown in Table 2, the accelerated freezing procedure of the present disclosure using CC without the use of egg yolk saves significant amount of time as compared with the conventional step-wise processing time in routine freezing using egg yolk (35 min vs >2 hours).

TABLE 2

Step-wise processing time in routine freezing using egg yolk and accelerated freezing using CC.

Routine freezing with egg yolk:

| | | |
|---|---|---|
| 1. | Cooling from body temperature to 22° C. | 20 min |
| 2. | Cooling 22° C. to 4° C. | >90 min |
| 3. | Packaging of straws at 4° C.-depending upon number of straws | |
| 4. | Cooling from 4° C. to −10° C. @ −3° C./min | 5 min |
| 5. | Cooling from −10° C. to −80° C. @ −10° C./min | 7 min |
| 6. | Plunging in liquid nitrogen | |
| | Total duration: | >2 hrs |

Accelerated freezing with CC (egg yolk free)

| | | |
|---|---|---|
| 1. | Cooling from body temperatureto 22° C. | 20 min |
| 2. | Packaging of straws at 22° C. Depending upon number of straws | |
| 3. | Cooling from 22° C. to +10° C. @ 1° C./min | 12 min |
| 4. | Cooling from +10° C. to −80° C. @ −40° C./min | 3 min |
| 5. | Plunging in liquid nitrogen | |
| | Total duration | 35 min |

Example 2

Cholesterol: Cyclodextrin Complex

The purpose of this study was to determine the fertility potential of semen extended with cholesterol of plant origin (PhytoChol, Wilshire Technologies, NJ) in a fixed time insemination program for beef cows. Cholesterol: cyclodextrin complex (CC complex) has been used as an adjunct in semen extenders carrying egg yolk to facilitate the delivery of exogenous cholesterol into sperm plasma membranes. Cholesterol increases membrane stability and resist phase transition changes, and cyclodextrins can act as carriers for hydrophobic molecules such as cholesterol. Improvement of sperm cryopreservation parameters are seen after semen treatment with the combination of CC and egg yolk in stallion (Combes et al. 2000), bull (Purdy & Graham 2004), boar (Tomás et al. 2011) and Bison (Hussain et al, 2013). However, CC has not been used alone as a semen extender in the absence of egg yolk.

Methods and Solutions

Preparation of tris buffer and extenders and cholesterol: cyclodextrin (CC) complex, and procedures for cryopreservation of semen were as described in Example 1.

Semen Collection and Processing

Figure 2:
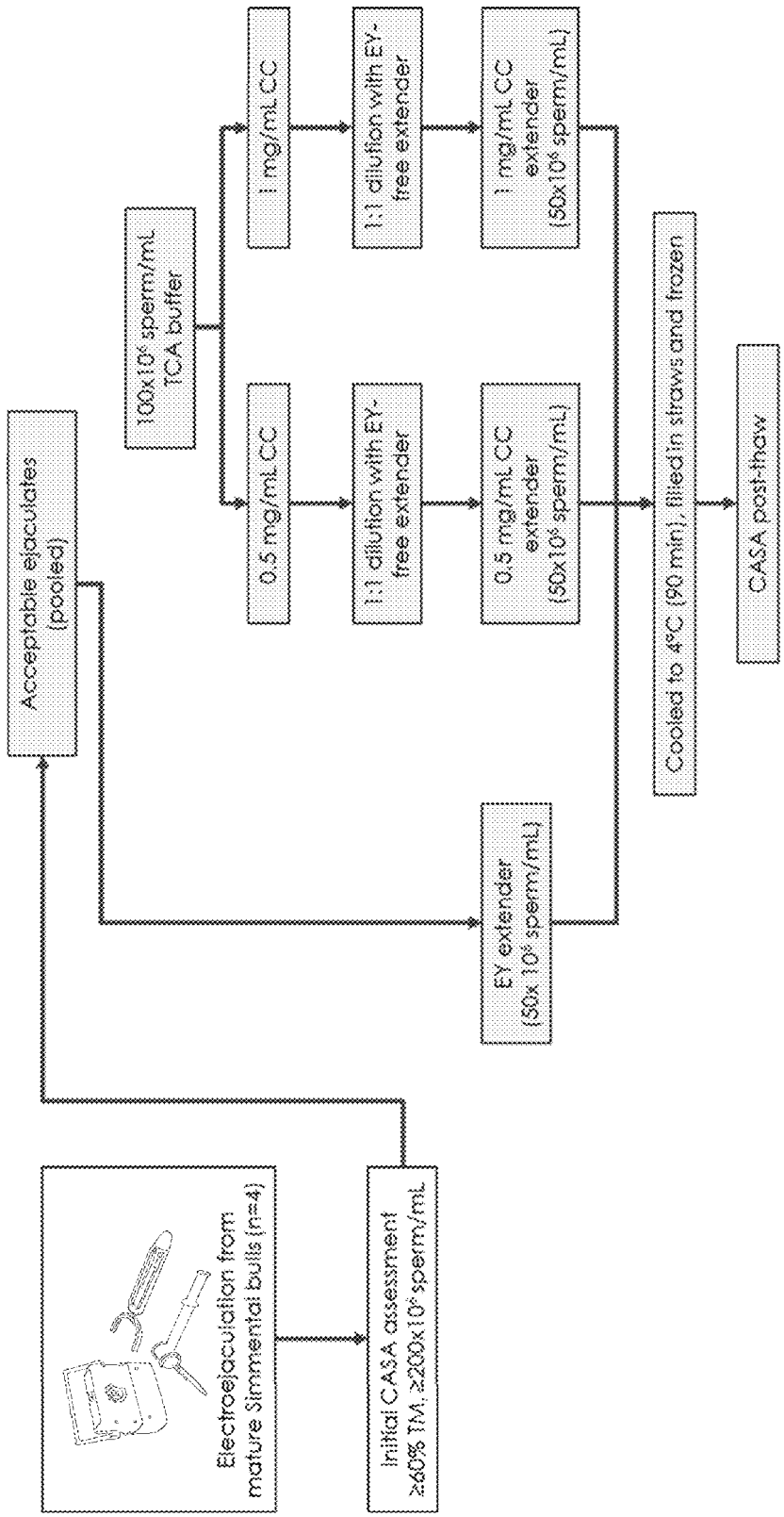
FIG. 2 is a flow chart of semen collection and processing.

A flow chart of semen collection and processing is shown in FIG. 2. Semen was collected by electro-ejaculation from mature Simmentals bulls (n=4 bulls, 4 replicates/bull) and analyzed using Computer Assisted Semen Analysis (CASA). Ejaculates from different bulls with ≥200×10$^6$ sperm/mL and ≥60% total motility were pooled. The pooled ejaculates were distributed into three treatments and diluted to 50×10$^6$/mL in Tris-citric-acid base extenders containing either egg yolk (20% v/v egg yolk, control), 0.5 mg cholesterol: cyclodextrin complex (CC) per mL semen, or 1.0 mg CC per mL semen. Glycerol (7% v/v) was added to each extender. Extended semen was loaded into 0.5 mL straws and frozen to −196° C. Post-thaw sperm motility was analyzed using CASA.

Fixed-Time Artificial Insemination

Figure 3:
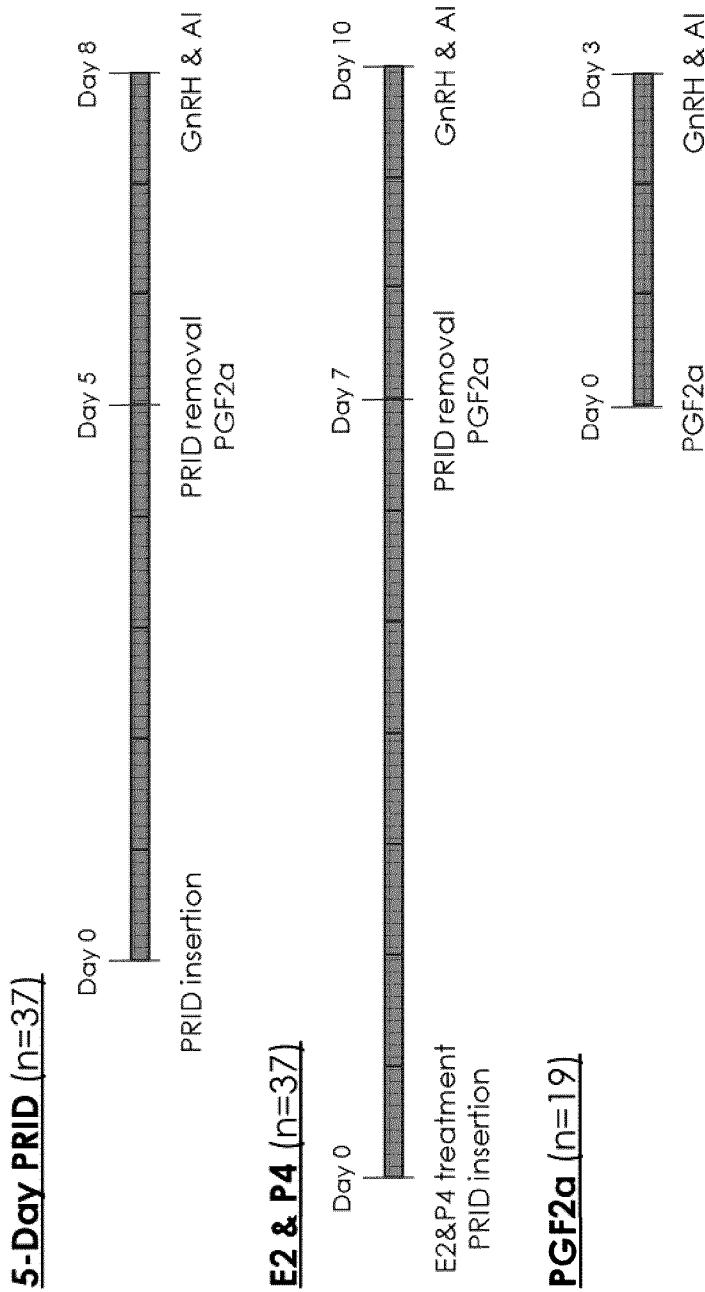
FIG. 3 is exemplary time-lines depicting fixed-time artificial insemination. Ovulation was synchronized among multiparous beef cows using one of three protocols.

Semen for insemination was thawed at 37° C. for about 60 sec as in Example 1. Frozen semen can be thawed for greater than 60 sec. Ovulation was synchronized among multiparous beef cows using one of three protocols (FIG. 3): 1) 5-day intravaginal progesterone-releasing device (PRID) and PGF2α treatment on the day of PRID removal (n=37 on random days of cycle); 2) estradiol+progesterone treatment and 7-day PRID followed by PGF2α on the day of PRID removal (n=37 on random days of cycle); or 3) PGF2α alone (n=19 on Day 7 to 9 from ovulation). Cows were treated with GnRH and assigned randomly to be inseminated with one of the three semen treatments 72 h after PGF2α treatment. Ovulations were confirmed and pregnancies were diagnosed 28-35 days after insemination by ultrasonography.

Results

Post-thaw sperm motility was compared among extenders by analysis of variance. Total motility (52±3%, 59±3% and 62±7%) and progressive motility (47±3%, 54±3% and 58±6%) did not significantly differ among the egg yolk, 0.5 mg CC and 1.0 mg CC extenders, respectively (Table 3). There is a trend of increased motility with CC.

TABLE 3

Effect of semen extender on post-thaw sperm total and progressive motility.

| Extender | Total Motility (%) | Progressive Motility (%) |
|---|---|---|
| Egg yolk | 52 ± 3 | 47 ± 3 |
| 0.5 mg/mL CC | 59 ± 3 | 54 ± 3 |
| 1 mg/mL CC | 62 ± 7 | 58 ± 6 |

Values are expressed as mean ± SEM · EY, n = 4; 0.5 mg/mL CC, n = 4; 1 mg/mL CC, n = 4.
No difference among treatments (p > 0.05).

Pregnancy rates were compared among groups by generalized linear mixed model. There were no differences in pregnancy rates among synchronization groups; therefore, data were combined to compare the effects of semen extender. Four cows were excluded due to improper synchronization treatment. Pregnancy rates of cows inseminated with egg yolk (n=31), 0.5 mg CC (n=31) and 1.0 mg CC (n=27) semen were 32%, 74% and 52%, respectively (P<0.05) (Table 4). Fertility in cattle inseminated using semen extended with cholesterol of plant origin has not been previously reported. We conclude that plant cholesterol may be used to replace animal proteins (egg yolk or milk origin) in bovine semen cryopreservation.

TABLE 4

Effect of semen extender on pregnancy rates in synchronized beef cows.

| Extender | Pregnant (n) | Ovulated (n) | Pregnancy rate |
|---|---|---|---|
| Egg yolk | 9 | 31 | 32%$^a$ |
| 0.5 mg/mL CC | 22 | 31 | 74%$^b$ |
| 1 mg/mL CC | 14 | 27 | 52%$^b$ |

Subscripts denote significant difference in column (p < 0.05).

Conclusions

Cholesterol-cyclodextrins can replace egg yolk and milk proteins in bovine semen cryopreservation. There was no difference in post-thaw sperm parameters compared to egg yolk extender. Acceptable field fertility can be achieved in synchronized beef cows following fixed-time artificial insemination with animal protein-free semen.

Example 3

Cryopreservation of Bull Semen without Exogenous Animal Protein and Equilibration Time I Production of bull semen without exogenous animal protein in the shortest possible time has been a goal for animal scientists and sperm cryobiologists, for a long time. In this study, treatment of bull semen with exogenous animal or plant cholesterol replaced egg yolk completely from semen processing and led to freeze semen in a short time.

Bovine semen cryopreservation is a popular and successful technique for conservation and exploitation of genetically superior animals. Routinely, bull semen is frozen in extender containing egg yolk or milk products, and slowly cooled to 4° C. in few hours. However, egg yolk and milk pose biosecurity risks to human involved in semen processing. At a typical commercial breeding centre, the existing semen cryopreservation procedure is quite time-consuming. Cholesterol-cyclodextrin (CC) complex along with egg yolk has been used to improve the cryosurvival of mammalian sperm (Purdy and Graham, 2004). The objectives of this study were to replace egg yolk with exogenous animal- and plant-based cholesterol, to compare the animal and plant cholesterol to cryopreserve bull semen without egg yolk, and to accelerate the semen cryopreservation processing time using animal and plant based cholesterol.

Material and Methods

Semen was collected by electro-ejaculation from 5 Black Angus beef bulls stationed at University of Saskatchewan Livestock Farm. Semen was analysed using CASA. Ejaculates possessing >60% sperm motility and >400 million/mL concentration were pooled, and placed at 22° C. for 15 min. Semen was divided into 4 groups: 1) semen extended tris citric acid (TB)-egg yolk (20% v/v)-glycerol (abbreviated as "TEYG") [(7% v/v) extender; 2) semen pre-exposed to plant CC (1 mg/ml) for 15 min and then extended in TB-glycerol (7% v/v) extender without egg yolk; 3) as in group 2, except animal CC (1 mg/ml) was used instead of plant CC; and 4) semen without egg yolk and CC, but extended in TB-glycerol (7% v/v). Each kind of semen was frozen as per routine (Routine Freezing, RF; as described in Table 2 of Example 1) or frozen with accelerated procedure without equilibration and using fast cooling rate (Accelerated Freezing, AF). In RF, semen straws were cooled to 4° C. for at least 90 min, filled in 0.5 ml-straws and frozen as follow: from 4° C. to −10° C.@−3° C./min and from −10° C. to −80° C.@−40° C./min. In AF, semen straws were filled at room temperature and frozen as follow: from 22° C. to 10° C.@−1° C./min and from 10° C. to −80° C.@−40° C./min. After reaching −80° C., semen straws were plunged in liquid nitrogen. Semen straws were thawed at 37° C. for 1 min. Post-thaw sperm motilities were analysed with CASA, and intact plasma membrane and acrosomes were analysed with flow cytometer using FITC-PNA/PI assay. This experiment was repeated five times (replicates) on different dates in same season. Data were analysed using ANOVA.

Results

Using RF, post-thaw sperm motilities, and plasm membrane and acrosome integrities were statistically similar between egg yolk, and plant and animal CC groups (Table 5). Using accelerated freezing, plant and animal CC yielded better post-thaw sperm total and progressive motilities than egg yolk extender (P<0.05) (Table 5). Accelerated freezing adversely affected egg yolk extended semen (P<0.05); whereas, AF did not show any adverse effect in plant and animal CC groups (P>0.05) (Table 5).

TABLE 5

Effects of routine freezing vs accelerated freezing using different semen extenders

| | Routine Freezing | | | | Accelerated Freezing | | | |
|---|---|---|---|---|---|---|---|---|
| | EY | Plant CC | Animal CC | No EY-No CC | EY | Plant CC | Animal CC | No EY-No CC |
| Mot % | 48 ± 4.9$^a$ | 52 ± 5.3$^a$ | 49 ± 4.7$^a$ | 16 ± 4.4$^b$ | 24 ± 3.2$^{B*}$ | 43 ± 3.1$^A$ | 47 ± 3.3$^A$ | 8 ± 1.7$^C$ |
| PMot % | 38 ± 3.5$^a$ | 44 ± 5.0$^a$ | 43 ± 4.9$^a$ | 11 ± 2.8$^b$ | 20 ± 3.5$^{B*}$ | 36 ± 1.9$^A$ | 38 ± 2.3$^A$ | 6 ± 1.5$^C$ |
| IPM-IACR % | 44 ± 6.3$^a$ | 52 ± 6.3$^a$ | 52 ± 7.1$^a$ | 18 ± 5.5$^b$ | 30 ± 6.2$^a$ | 46 ± 3.9$^a$ | 41 ± 3.3$^a$ | 10 ± 4.6$^b$ |

Superscripts ($^{a,b}$) denote difference in extender treatments within routine freezing group
Superscripts ($^{A,B,C}$) denote difference in extender treatments within accelerated freezing group
Asterisk (*) denotes difference between freezing procedure in sperm characteristics, within a treatment.

Conclusion

Bull semen can be frozen without egg yolk, using exogenous cholesterol, regardless of their source (plant or animal). Bull semen treated with exogenous cholesterol can be frozen by eliminating long equilibration time leading to a quicker procedure of semen cryopreservation.

Example 4

Figure 4:
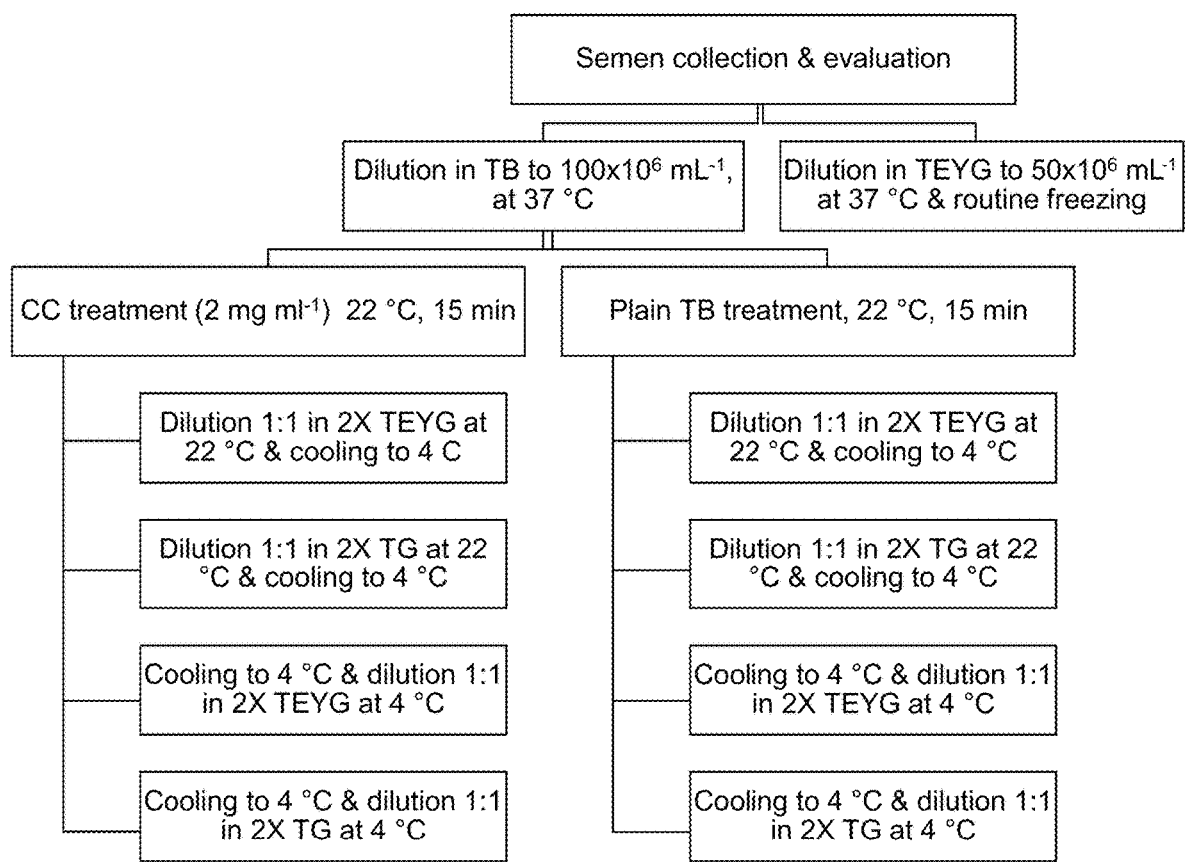
FIG. 4 is a schematic diagram of a representative method of semen freezing with and without egg yolk. Abbreviations: CC (cholesterol-cyclodextrin complex), TB (tris-citric acid buffer), TEYG (tris-citric acid-egg yolk-glycerol extender), TG (tris-citric acid-glycerol extender), 2× (double strength).

Cryopreservation of Bull Semen without Exogenous Animal Protein and Equilibration Time I The outline of this experiment is presented in FIG. 4. After initial evaluation, fresh semen was divided into two aliquots. Semen in aliquot 1 was diluted to $50 \times 10^6$ sperm $mL^{-1}$ in conventional Tris citric acid-egg yolk-glycerol (TEYG) extender (i.e. 'control semen') at 37° C., and kept in water bath (22° C.), along with other aliquots. Semen in aliquot 2 was diluted to $100 \times 10^6$ sperm $mL^{-1}$ with Tris buffer (TB) at 37° C. and cooled to 22° C. in water bath. At 22° C., semen was treated either with 2 mg $mL^{-1}$ CC complex or with equal volume of TB, at 22° C. for 15 min. One set of CC- and TB-treated semen samples were diluted with 2×TEYG or 2× TG extenders (1:1, final concentration $50 \times 10^6$ sperm $mL^{-1}$) at 22° C. and slowly cooled to 4° C. Another set of CC- and TB-treated semen samples were first slowly cooled to 4° C., and then diluted with 2×TEYG or 2× TG extenders (1:1, final concentration $50 \times 10^6$ $mL^{-1}$). Slow cooling of semen samples from 22° C. to 4° C. was achieved in a walk-in cold room (4° C.) in 90-100 min. Semen was packaged in 0.5 ml French straws and frozen to −80° C. in a programmable cell freezer (ICE-CUBE 14-S, Sy-Lab Version 1.30, Gerate GmbH, Neupurkdersdof, Austria) using freezing curve reported earlier (Anzar et al. 2011). Briefly, in cell freezer, semen straws were cooled from +4° C. to −10° C.@−3° C. $min^{-1}$, and from −10° C. to −80° C.@−40° C. $min^{-1}$. At −80° C., semen straws were plunged in liquid nitrogen and stored for at least 24 h. Three straws per sample per bull were thawed in a water bath at 37° C. for 60 sec, and pooled. Post-thaw motility characteristics were evaluated using CASA.

Cleavage and Blastocyst Rates

Cleavage and blastocyst rates were determined based on examination of embryo under inverted microscope.

Statistical Analysis

Figure 5:
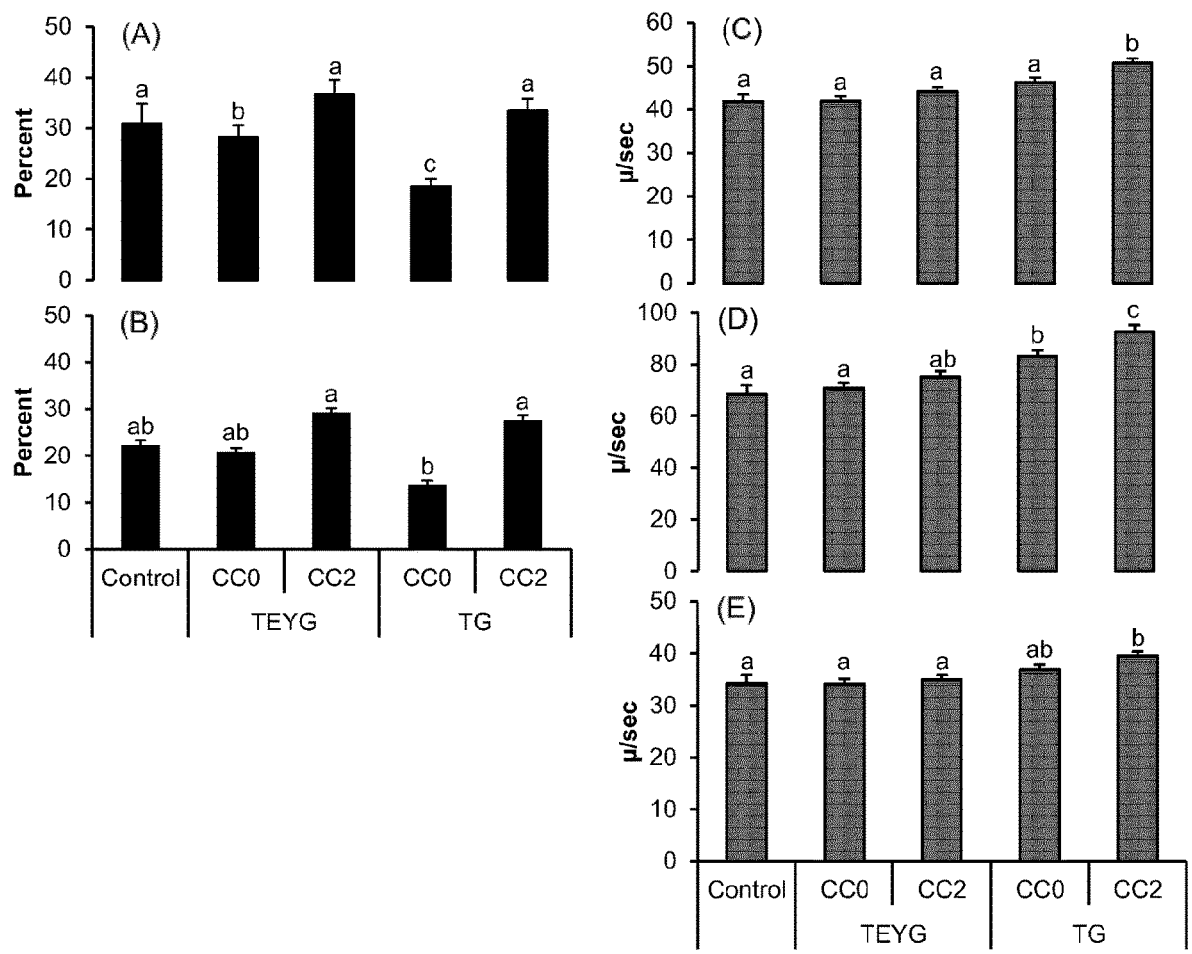

Data were expressed as means±SEM and analyzed using SAS® MIXED procedure (version 9.2, SAS institute Inc. Carry, NC). In this Example, first 2×2 factorial design was used to observe the effects of CC and temperature of addition of glycerolated extender (TG). Later, data were pooled over temperature due to lack of significant difference and completely randomized design was used to compare semen in different extenders. In Example 4, the effects of glycerol concentration were analyzed using completely randomized design, at 0 and 2 h separately. In case of $P<0.05$, means were separated using Tukey's test. Cleavage and blastocyst rates in TEYG and CC-TG semen were analyzed using Chi-square test. In FIG. 5, data were pooled over temperature of glycerol addition due to its lack of significance.

Results

Figure 6:
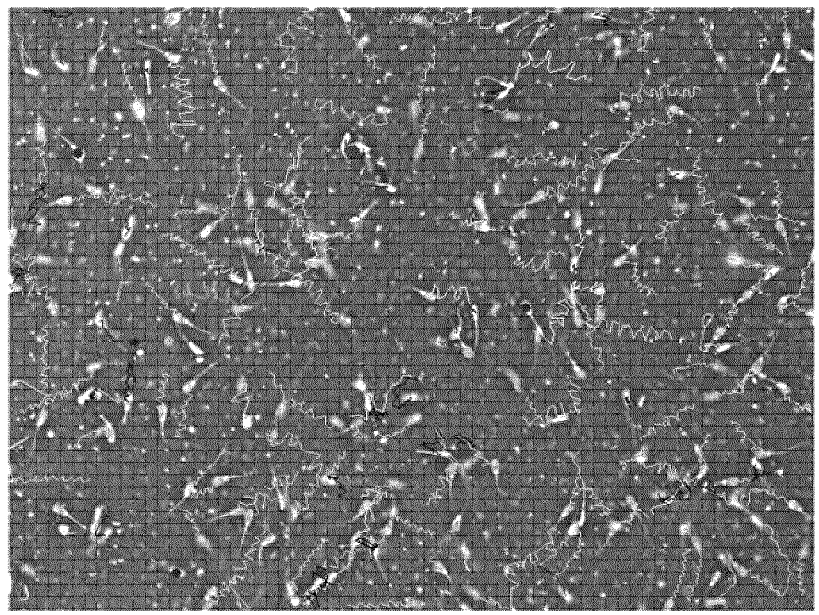
FIGS. 6A and B show video stills of post-thaw sperms.
FIG. 6B shows a video still of post-thaw sperms without egg yolk.
Figure 6:
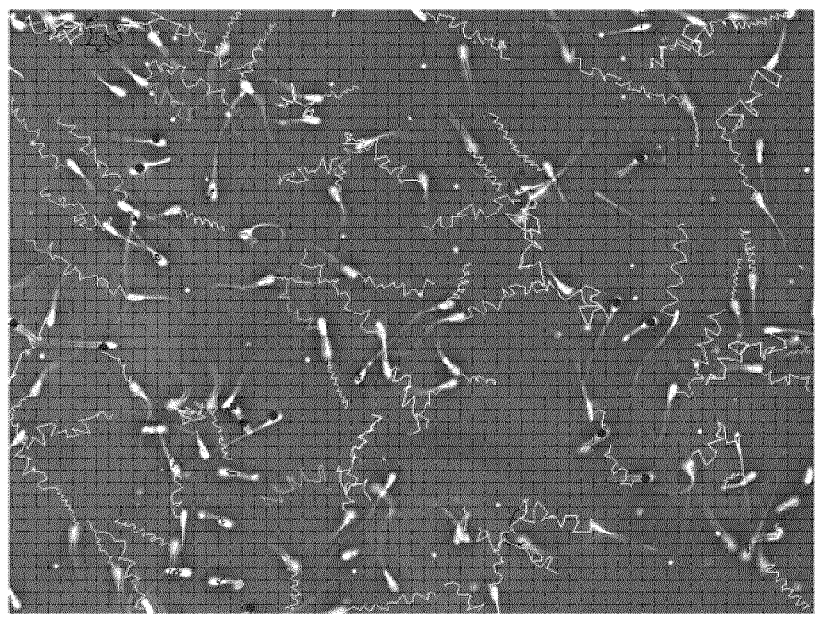

The effects of temperature of glycerol addition and extender x temperature of glycerol addition interaction on motion characteristics were not significant. Therefore, data (pooled over temperature) on motion characteristics in control and treatment groups are presented in FIG. 5. Total and progressive motilities were statistically equal between control (TEYG) and CC-treatment groups (regardless of presence or absence of egg yolk). Sperm treated with CC complex before dilution in TEYG or TG extenders showed higher ($P<0.05$) sperm total and progressive motilities. Both sperm motilities were the lowest ($P<0.05$) in the absence of CC complex treatment and egg yolk. Average path, curvilinear and straight-line velocities were higher ($P<0.05$) in CC-TG than control and TEYG frozen semen. Under CASA, the background of sperm diluted in CC-TG extender was much clear than in TEYG extender (FIG. 6).

These experiments demonstrate the successful cryopreservation of bull semen without adding any exogenous protein (animal or plant origin) in semen extender. Treatment of bull sperm with CC complex before cooling completely removed the need of egg yolk from conventional semen cryopreservation procedure.

This study clearly demonstrated that post-thaw sperm motilities and velocities were similar or better in egg yolk-free CC-TG extender than in conventional TEYG extender. Regardless of the presence or absence of egg yolk, the treatment of sperm with CC complex improved post-thaw sperm motility. Without wishing to be bound by theory, higher post-thaw velocities in sperm pre-exposed to CC-complex and diluted in tris-glycerol extender rather than egg yolk might be due to density of egg yolk content, as evident in video stills. It indicated that bull semen can be successfully frozen without egg yolk provided sperm are treated with CC complex before dilution in glycerolated extender. Egg yolk, one of the most common ingredient in extender, contributes its lipidoproteins, cholesterol and anti-oxidant moieties on sperm membrane (Bergeron and Manjunath 2006b). Low density lipoproteins fraction present in egg yolk protects bull sperm during initial cooling (Pace and Graham 1974; Moussa et al. 2002).

Both sperm motilities were the lowest when semen was frozen without CC complex treatment and egg yolk in extender. It indicated that glycerol alone in extender cannot protect sperm during initial cooling. Bull sperms need egg yolk in extender and/or CC complex treatment to survive damage during initial cooling from room to refrigerated temperature. In these Examples, a true protective effect of CC-complex during initial cooling was determined by adding the glycerolated (TG) extender at 22 or 4° C. Earlier, it has been suggested that addition of glycerol at 5° C. provided better protection to bovine spermatozoa during freezing compared to addition at >5° C. (Polge 1952). In these Examples, lack of difference in sperm motilities due to temperature of glycerol addition confirmed that CC complex can solely protect bull sperm against initial cooling. The skilled person can readily recognize that the glycerolated extender can be added in semen at 22° C.

Example 5

Effect of Glycerol Concentration in Extender on Cryopreservation of Semen without Exogenous Protein In this Example, control semen containing egg yolk was processed as in Example 4. Based on results from Example 4, semen was treated with CC complex at 22° C. for 15 min and diluted (1:1) with TG extender varying in glycerol concentration, to final sperm concentration $50 \times 10^6$ $mL^{-1}$. Two separate trials were conducted to test the effect of glycerol concentration in TG extender on cryopreservation of semen. Sperm treated with CC and diluted in TG extender were collectively called CC-TG semen.

Trial 1: In this trial, bull sperm were treated with CC complex (2 mg $mL^{-1}$ semen) at 22° C. for 15 min. Semen was diluted (1:1) with TG extender such that final glycerol concentration was 1, 3, 5 or 7% (v/v). In addition, bull sperm were treated with CC complex 2, 3 or 4 mg $mL^{-1}$ semen and diluted with plain TG extender (0% glycerol) to examine if CC complex is sufficient enough to cryoprotect bull sperm without glycerol in extender.

Trial 2: In this trial, bull sperm were treated with CC complex (2 mg $mL^{-1}$) at 22° C. for 15 min and semen was diluted (1:1) in TG extender such that final glycerol concentration is 7, 9 or 11% (v/v).

In both trials, semen diluted and frozen in TEYG was considered as first control and semen diluted and frozen in CC-TG7% glycerol was considered as second control. All control and treatment group semen samples were cooled to 4° C. and frozen in programmable cell freezer as in Example 4.

Post-thaw sperm motility parameters were assessed using CASA. Sperm plasma membrane (PM) and acrosome (AR) integrities were evaluated with flow cytometer, at 0 and 2 h post-thaw while incubating at 37° C. in a water bath.

Computer-Assisted Sperm Analysis

Fresh semen was first diluted 1:20 in TCM-199 (37° C.) whereas frozen thawed semen was evaluated as such. An aliquot (2.5 µl) of semen sample was loaded in a pre-warmed (37° C.) chamber slide (Leja Netherlands; 20 µM depth). At least 200 sperms were analyzed for total motility (% of all moving sperms), progressive motility (% of all sperms moving in straight line), average path velocity (VAP, µm sec$^{-1}$), curvilinear velocity (VCL, µm sec$^{-1}$) and straight line velocity (VSL, µm sec$^{-1}$) using CASA (Anzar et al. 2011).

Flow Cytometer Analysis

Flow cytometer analysis was conducted to evaluate sperm plasma membrane (PM) and acrosomes (AR) integrities, as described earlier (Anzar et al. 2011). After thawing, semen was diluted to 1×10$^6$ sperm mL$^{-1}$ in PBS-0.5% BSA solution. Then, fluorescent dyes i.e. 1 µL fluorescein isothiocyanate-peanut agglutinin (FITC-PNA; Sigma chemicals, St. Louis, MO; stock 1 mg mL$^{-1}$ in PBS) and 6.25 µL propidium iodide (PI; Invitrogen; stock 2.4 mM in water) were added mL$^{-1}$ semen, incubated for 10 min at 37° C. Sperms in each sample were fixed by adding 10 µL of 10% formaldehyde and analyzed within a few hours. At least 10,000 sperms of each semen sample were analyzed with flow cytometer (Partec Cyflow Space, version 2.4 by Partec GmbH, Munster, Germany) equipped with 400 mW argon laser. FITC-PNA and PI were excited with 488 nm blue laser and their fluorescent data were recorded with photo multiplier detectors FL-1 and FL-3, respectively (Anzar et al. 2011) after gating sperm population with forward and side scatters. Sperms with intact PM and AR excluded PI and FITC-PNA, whereas sperms with compromised PM and AR stained red (PI) and green (FITC) respectively.

Results

Trial 1: Post-thaw motion and structural characteristics of bull sperm frozen in CC-TG extender containing ≤7% glycerol concentration are presented in FIG. 7 and Table 6, respectively. Sperm total motility was higher (P<0.05) in TEYG control semen and CC-TG7% than other semen groups. Similarly, post-thaw sperm progressive motility among TEYG control, CC-TG7% and CC-TG5% was not different significantly. Post-thaw sperm average path velocities were similar (P>0.05) among TEYG control, CC-TG7% and CC-TG5% but higher than rest of low glycerol concentrations. Curvilinear velocity was higher (P<0.05) in CC-TG7% and CC-TG5% than TEYG control semen. Straight-line velocity was higher (P<0.05) in sperm treated with CC and diluted in glycerolated (TG) extenders than in glycerol-free extender. Overall, sperm motilities and velocities decreased (P<0.05) with decline in glycerol concentrations in TG extender. Regardless of CC complex treatment, sperm did not freeze well without glycerol.

TABLE 6

Post-thaw plasma membrane and acrosome integrities of bull semen frozen without egg yolk (except control group) in extenders containing lower than conventional glycerol concentration.

| | IPM-IAR | IPM-CAR | CPM-IAR | CPM-CAR |
|---|---|---|---|---|
| Control | 40 ± 3.7$^a$ | 2 ± 0.3$^{ab}$ | 20 ± 1.0$^a$ | 38 ± 3.2$^f$ |
| CC2 + G7 | 33 ± 3.2$^b$ | 1 ± 0.3$^{ab}$ | 9 ± 1.0$^b$ | 57 ± 3.7$^e$ |
| CC2 + G5 | 33 ± 3.4$^b$ | 1 ± 0.2$^{ab}$ | 10 ± 1.3$^b$ | 56 ± 3.6$^e$ |
| CC2 + G3 | 20 ± 3.3$^c$ | 1 ± 0.2$^{ab}$ | 10 ± 1.2$^b$ | 69 ± 3.3$^d$ |
| CC2 + G1 | 12 ± 1.8$^d$ | 3 ± 1.5$^a$ | 12 ± 1.7$^b$ | 73 ± 2.6$^{cd}$ |
| CC2 + G0 | 4 ± 0.4$^e$ | 1 ± 0.1$^b$ | 10 ± 1.3$^b$ | 85 ± 1.4$^a$ |
| CC3 + G0 | 4 ± 0.6$^e$ | 1 ± 0.2$^{ab}$ | 12 ± 1.5$^b$ | 83 ± 2.1$^{ab}$ |
| CC4 + G0 | 4 ± 0.6$^e$ | 3 ± 1.8$^{ab}$ | 12 ± 1.9$^b$ | 77 ± 4.2$^{bc}$ |

Bull sperm were pre-exposed to cholesterol-cyclodextrin (CC; 2, 3 or 4 mg ml$^{-1}$) complex at 22° C. for 15 min and then diluted in tris extenders containing different glycerol concentration (G; 7, 5, 3, 1 or 0%, v/v) 22° C.. Data are presented as mean ± SEM of six independent replicates. Means with different superscripts$^{a-f}$, within a column, differ from each other (P < 0.05).
Abbreviations:
CC—cholesterol-cyclodextrin complex;
G—glycerol;
IPM-IAR—intact plasma membrane and intact acrosomes;
IPM-CAR—intact plasma membrane and compromised acrosomes;
CPM-IAR—compromised plasma membrane and intact acrosomes;
CPM-CAR—compromised plasma membrane and compromised acrosomes.

Post-thaw sperms with intact plasma membrane and intact acrosomes (IPM-IAR) were most prevalent in the TEYG control semen but this population decreased with concomitant increase in sperms with compromised plasma membrane and compromised acrosomes (CPM-CAR) as glycerol concentration declined in TG extender.

Trial 2: Post-thaw motion and structural characteristics of bull sperm frozen in TEYG and CC-TG extender containing ≥7% glycerol concentration (i.e. 7, 9 and 11%) are presented in FIG. 8 and Table 7. Sperm total and progressive sperm motilities were higher in CC-TG11% than control and CC-TG7% treatments. Average path and curvilinear velocities were higher (P<0.05) in CC-TG groups, regardless of glycerol concentrations, than TEYG control group.

TABLE 7

Post-thaw plasma membrane and acrosome integrities of bull sperm frozen without egg yolk (except control group) in extenders containing higher than conventional glycerol concentration.

| | IPM-IAR | IPM-CAR | CPM-IAR | CPM-CAR |
|---|---|---|---|---|
| Control | 48 ± 3.4$^a$ | 2 ± 0.2$^a$ | 22 ± 1.3$^a$ | 28 ± 3.2$^b$ |
| G7 | 37 ± 3.3$^b$ | 1 ± 0.2$^b$ | 10 ± 1.3$^b$ | 51 ± 3.4$^a$ |
| G9 | 35 ± 4.2$^b$ | 1 ± 0.2b$^b$ | 10 ± 0.9$^b$ | 55 ± 4.4$^a$ |
| G11 | 34 ± 4.1$^b$ | 1 ± 0.2$^b$ | 8 ± 1.0$^b$ | 56 ± 4.2$^a$ |

Bull sperm were pre-exposed to exogenous cholesterol-cyclodextrin complex (CC; 2 mg/ml) at 22° C. for 15 min and then diluted in TG extenders containing different glycerol concentration (CC; 7, 9 or 11%, v/v) at 22° C.. Data are presented as mean ± SEM of six independent replicates. Means with different superscripts ± within a column differ from each other (P < 0.05).
Abbreviations:
CC—cholesterol-cyclodextrin complex;
G—glycerol;
IPM-IAR—intact plasma membrane and intact acrosomes;
IPM-CAR—intact plasma membrane and compromised acrosomes;
CPM-IAR—compromised plasma membrane and intact acrosomes;
CPM-CAR—compromised plasma membrane and compromised acrosomes.

Post-thaw sperm with IPM-IAR were higher in TEYG control than all CC treatment groups (P<0.05). The corresponding sperm population with CPM-CAR was lower in control than all CC treatment groups.

CC complex could not replace glycerol which remained essential for protection of sperm against deep-freezing.

These results revealed that post-thaw sperm motilities and velocities were dependent upon concentration of glycerol in TG extender. An increase in CC complex from 2 mg/ml to 4 mg/ml without glycerol yielded only <10% sperm motility and sperm with IPM-IAR. This Example showed that treatment of sperm with 2 mg CC complex and 5% to 7% glycerol in TG extender is a suitable combination for freezing bull semen without egg yolk. There was a 7-11% decline in sperm with intact plasma membrane and intact acrosomes (IPM-IAR) in CC-TG extender as compared to TEYG extender. Biologically this difference is not that great to influence fertility in cows. Without wishing to be bound theory, the small effect might be due to detrimental effects of glycerol, as it has been suggested that glycerol could activate various caspases which may lead to human sperm to undergo programmed cell death (Wundrich et al. 2006).

Example 6

In Vitro Fertilization Ability of Bovine Semen Frozen With and Without Egg Yolk

Beef bull semen was frozen with and without egg yolk as described in Example 4. Dairy bull semen procured from a Canadian breeding station was used as an internal control. In vitro maturation, fertilization and culture procedures were conducted as described earlier (Prentice-Biensch et al. 2012). Ovaries were collected from slaughtered cows and transported to lab at 22° C. within 8 h. The immature cumulus oocyte complexes (COCs) were aspirated from follicles (3-8 mm diameter). The immature COCs, containing more than three layers of cumulus cells and uniform cytoplasm, were washed (3×) in maturation medium (TCM-199 supplemented with 5% v/v calf serum, 5 μg ml$^{-1}$ LH, 0.5 μg ml$^{-1}$ FSH and 0.05 μg ml$^{-1}$ gentamicin). Groups of 20 COCs were incubated in 100 μl droplets of maturation medium, under mineral oil for 22 h at 38.5° C., 5% $CO_2$ in air and saturated humidity. For in vitro fertilization (IVF), beef semen frozen with and without egg yolk (n=3 bulls) and dairy semen straws were thawed at 37° C. for 60 sec. Thawed semen was washed through Percoll gradient (45% and 90%). After washing, sperms were added to Brackett-Oliphant (BO) fertilization medium to a final concentration 3×10$^6$ ml$^{-1}$. Groups of 20 COCs were incubated in 100 μl BO-sperm droplets at 38.5° C., 5% $CO_2$ in air and saturated humidity. After 18 h of COC-sperm co-incubation, cumulus cells and sperms attached to oocytes were mechanically removed via pipetting. The presumptive zygotes were washed (3×) through in vitro culture (IVC) medium consisting of CR1aa with 5% CS, 2% BME essential amino acids (v/v), 1% MEM nonessential amino acids (v/v), 1% L-glutamic acid (v/v), 0.3% BSA and 0.05 μg/ml gentamicin sulfate, transferred into 100 μl IVC droplets under mineral oil, and incubated at 38.5° C. under 5% $CO_2$, 90% $N_2$, 5% $O_2$ and saturated humidity. After 48 h in culture, the cleavage (2-8 cells) rate was recorded, and embryos continued culture in the same droplets. Subsequently, the blastocyst rate was determined on Days 7, 8 and 9 (Day 0=day of IVF). Both cleavage and blastocyst rates were calculated out of total number of oocytes fertilized in vitro.

Results

Semen frozen in TEYG and CC-TG extenders yielded similar in vitro cleavage and blastocyst rates (Table 8).

TABLE 8

In vitro cleavage and blastocyst rates with bull semen extended with and without egg yolk.

| Semen | No. of oocytes | Cleavage rate | Blastocyst rate |
|---|---|---|---|
| With egg yolk | 210 | 54 ± 8.1 | 28 ± 5.5 |
| Without egg yolk | 202 | 54 ± 6.3 | 28 ± 5.5 |
|  | p-value: | >0.05 | >0.05 |

Mean ± SEM; 3 replicates

Bull sperm cryopreserved with and without egg yolk demonstrated similar in vitro fertilizing ability.

This Example shows that cleavage and blastocyst rates were similar between semen frozen with TEYG and CC-TG extender. Semen frozen without egg yolk has capability to fertilize cows' oocytes in vitro.

Example 7

Electrophoresis of Bull Sperm Frozen With and Without Egg Yolk

Sperm proteins were extracted from fresh semen (control), and semen frozen in CC-TG and TEYG. The plain extenders containing CC-TG and TEYG were also run in electrophoresis, as controls. Fresh semen (100 μl) was centrifuged at 2000×g for 10 min and sperm pellet was resuspended in extraction buffer (1% w/v sodium deoxycholate, 0.1% w/v sodium dodecyl sulphate and 1% v/v Triton-X in 1×PBS, pH 7.2) and stored at −80° C. Egg yolk containing frozen-thawed semen sample was divided into two aliquots. In aliquot 1, frozen-thawed semen (100 μl) was layered on 45% Percoll in PBS and centrifuged at 2000×g for 10 min. Sperm pellet was washed once again with TB at 1800×g for 5 min at room temperature to remove Percoll particles. Sperm pellet was resuspended in 100 μl extraction buffer and called "frozen-EY-W" sperm. In aliquot 2, frozen-thawed semen was centrifuged twice in PBS at 500×g for 5 min to remove egg yolk extender and sperm pellet was resuspended in 100 μl extraction buffer and called "frozen-EY-C" sperm. Sperm mixtures were kept on ice for 30 min while mixing every 10 min with pipette, sonicated for 10 min, centrifuged at 15,000×g for 15 min at 4° C. and supernatant was used for electrophoresis. The protein concentration of each semen sample was measured with Bio-Rad protein assay. Protein samples were mixed with 5× sample buffer, boiled for 5 minutes and cooled on ice. Total 15 μg protein from each fresh and frozen semen samples and 25 μg from TEYG extender were loaded on 10% acrylamide gel (Bio-Rad). Since no protein was detected in CC-TG extender (2 mg ml$^{-1}$ in TG extender), volume equivalent to TEYG extender was loaded on gel to confirm lack of protein in CC-TG extender. Electrophoresis was done at room temperature initially at 75V for 15 minutes and then at 100 V until the bromophenol blue front line reached the bottom of gel. Gels were stained with Coomassie blue stain (0.1% w/v Coomassie Brilliant Blue, 50% v/v methanol, 10% v/v acetic acid in water) on shaking platform for 1 h. The extra stain was removed by destaining solution (10% v/v methanol and 40% v/v acetic acid in water) for 30 minutes on shaking platform. The stained gels were scanned with Gel Doc™ EZ System (Bio-Rad Laboratories, Mississauga, ON, Canada) for protein profile.

Results

Figure 9:
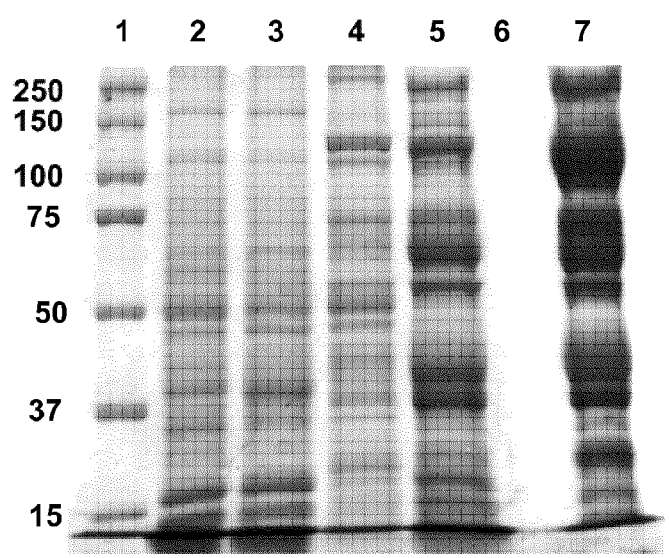
FIG. 9 shows a representative SDS gel electrophoresis of proteins extracted from fresh and frozen thawed bull sperm, and cholesterol-cyclodextrin tris-glycerol (CC-TG) and tris-egg yolk-glycerol (TEYG) extenders. Lane distribution: 1, marker; 2, fresh sperm; 3, sperm frozen in CC-TG extender; 4, sperm frozen in TEYG extender and washed through Percoll gradient; 5, sperm frozen in TEYG extender and centrifuged twice; 6, CC-TG extender; 7, TEYG extender. Lanes 2-5 contained 15 μg protein extract, lane 6 contained plain CC-TG extender (volume equivalent to TEYG sample used in lane 7), and lane 7 contained 25 μg protein extract from plain TEYG extender.

Electrophoretic profiles of proteins from fresh and frozen sperm, CC-TG extender and egg yolk extender are shown in FIG. 9 and Table 9. Protein profiles of fresh and CC-frozen sperms were similar and 18 proteins (180, 113, 101, 92, 83, 73, 64, 60, 50, 47, 44, 42, 39, 33, 28, 27, 22 and 18 kDa) were common between two semen types. Electrophoresis separation of proteins in egg yolk extender showed 15 protein bands, and out of which there were nine proteins (68, 58, 51, 41, 39, 36, 31, 24 and 20 kDa) common between egg yolk extender and sperm frozen in egg yolk (frozen-EY-W and frozen-EY-C).

TABLE 9

Protein profile (molecular weight [KDa] and band %) of fresh and frozen-thawed bull sperm, and egg yolk extender

| Fresh | | Frozen-CC-TG | | Frozen-EY-W | | Frozen-EY-C | | TEYG extender | |
|---|---|---|---|---|---|---|---|---|---|
| MW (KDa) | Band % | MW (KDa) | Band % | MW (KDa) | Band % | MW (KDa) | Band % | MW (KDa) | Band % |
| ≥250 | 12.1 | ≥250 | 10.6 | ≥250 | 27.9 | ≥250 | 9.8 | ≥250 | 6.2 |
| 240 | 4.0 | 236 | 2.9 | 168 | 0.1 | 217 | 3.7 | 199 | 8.3 |
| 180 | 2.7 | 180 | 3.2 | 148 | 0.4 | 138 | 1.1 | 133 | 1.0 |
| 113 | 1.2 | 111 | 0.5 | 120 | 6.6 | 114 | 6.9 | 98 | 24.7 |
| 101 | 0.1 | 98 | 0.1 | 107 | 2.6 | 103 | 2.1 | <u>68</u> | 4.7 |
| 92 | 0.2 | 91 | 0.2 | 99 | 0.3 | 90 | 0.1 | <u>58</u> | 3.3 |
| 83 | 0.7 | 84 | 0.3 | 89 | 0.3 | <u>71</u> | 3.8 | <u>51</u> | 4.8 |
| 73 | 0.5 | 73 | 0.6 | 83 | 0.5 | <u>61</u> | 9.7 | <u>41</u> | 10.0 |
| 69 | 0.1 | 64 | 1.2 | <u>71</u> | 4.7 | <u>53</u> | 4.4 | <u>39</u> | 6.1 |
| 64 | 0.6 | 60 | 0.5 | <u>65</u> | 3.9 | <u>51</u> | 0.7 | <u>36</u> | 8.2 |
| 60 | 1.4 | 50 | 3.7 | <u>55</u> | 2.2 | 47 | 0.2 | <u>31</u> | 0.6 |
| 50 | 4.6 | 47 | 1.3 | <u>50</u> | 6.3 | <u>40</u> | 11.7 | <u>24</u> | 6.9 |
| 47 | 1.1 | 44 | 0.6 | <u>47</u> | 1.9 | <u>39</u> | 2.3 | <u>20</u> | 1.1 |
| 44 | 0.1 | 42 | 1.0 | 44 | 0.6 | <u>37</u> | 8.6 | 14 | 5.9 |
| 42 | 0.9 | 39 | 6.4 | <u>42</u> | 3.2 | <u>33</u> | 1.0 | ≤10 | 8.1 |
| 39 | 1.8 | 34 | 1.4 | <u>40</u> | 1.7 | 28 | 0.3 | | |
| 33 | 2.0 | 30 | 0.1 | <u>38</u> | 3.0 | <u>26</u> | 0.9 | | |
| 28 | 0.4 | 29 | 0.1 | <u>34</u> | 1.0 | <u>22</u> | 2.8 | | |
| 27 | 0.3 | 28 | 0.2 | 29 | 0.4 | <u>19</u> | 1.9 | | |
| 22 | 6.7 | 23 | 7.6 | <u>24</u> | 3.5 | 17 | 1.1 | | |
| 18 | 4.2 | 20 | 2.8 | 23 | 0.9 | 14 | 11.9 | | |
| 14 | 41.8 | 18 | 3.1 | 21 | 0.3 | 12 | 6.5 | | |
| ≤10 | 12.3 | 14 | 37.3 | <u>19</u> | 0.8 | ≤10 | 8.5 | | |
| | | ≤10 | 14.4 | 14 | 8.7 | | | | |
| | | | | ≤10 | 18.0 | | | | |

Proteins were extracted from fresh and frozen sperm in either CC-TG extender (Frozen-CC-TG) or TEYG extender. After thawing, sperms frozen in egg yolk were either washed through Percoll gradient (Frozen-EY-W) or gently centrifuged (Frozen-EY-C) to remove egg yolk. Molecular weights and band densities were determined using Bio-Rad's Gel DocTM EZ System. Values in bold represent common proteins between fresh and frozen-CC sperm. Values in bold and underline represent common proteins among frozen-EY-W, frozen-EY-C and egg yolk extender. Protein bands between treatments with molecular weight difference ±3 kDa were considered similar.

Semen frozen in CC-TG extender (without egg yolk) exhibited similar protein profile as fresh semen. In comparison, proteins in egg yolk bound tightly with bull sperm plasma membrane and could not be removed completely even after washing through Percoll.

This Example shows that egg yolk proteins bind tightly with sperm membrane and some proteins could not be removed even after Percoll washing. It has always been difficult to assess changes in sperm plasma membrane protein profile in semen frozen in egg yolk extender. Post-thaw protein profile of sperm frozen in CC-TG extender was similar to that in fresh semen. Therefore, semen frozen without egg yolk is useful to study sperm proteomics in fresh and frozen-thawed semen without adulteration of exogenous proteins. Moreover, freeze-resistant membrane protein can be identified from mammalian sperm and used to improve the freezing ability of semen from poor freezer species.

Example 8

Cell-Penetrating Anti-Oxidants for Cryosurvival of Mammalian Semen

Mammalian sperm produce reactive oxygen species (ROS) which plays physiological roles in their health and viability. However, if large amount of ROS is produced, they cause lipid peroxidation of cell membrane leading to cell death. Moreover, cryopreservation also promotes the production of ROS beyond the physiological limits. In this study, the damage to mammalian sperm was prepared using cell-penetrating peptides (DMT-SS31 and DMT-mTP4, hereafter called SS31 and mTP4, respectively). The post-thaw longevity of cryopreserved bovine sperm would be improved by mitigating their reactive oxygen species production using cell permeating anti-oxidants (SS31 and mTP4). The specific objectives were:

1. Delivery of fluorescent-labelled fluorescent labelled SS31 and mTP4 across the plasma membrane of bovine sperm.
2. Assessment of suitable incubation temperature (37 vs. 22° C.) for internalization of SS31 and mTP4 in bull sperm.
3. Improvement in post-thaw viability of bovine semen with mitochondria specific anti-oxidant peptide.

Internalization of Cell Penetrating Peptides (SS31 and mTP4) on Fresh Bull Sperm and its Effect on Sperm Motility Studies were conducted to assess the penetration of other cell-penetrating peptides (CPPs i.e. SS31 & mTP4) through bull sperm. SS31 is D-Arg-DMT-Lys-Phe (SEQ ID NO:1), where DMT denotes 2',6' dimethyltyrosine. mTP4 is DMT-D-MWWRRSRTNSLRYT (SEQ ID NO:2), where DMT denotes 2',6' dimethyltyrosine. SS31 and mTP4 were purchased from CanPeptide (Pointe-Claire, Quebec, Canada).

Semen was collected from four bulls using electro-ejaculator. Semen was analyzed with Computer Assisted Semen Analysis (CASA) and washed (2×) with tris citric acid buffer (TB). The washed semen was diluted to 2.2 million/ml with TB. Semen (46 µl) was mixed with 4 µl of 100 µM solution of SS31 or mTP4. TB buffer alone was added in the control sample. The sperm were incubated for 1, 3, and 24 hr at room temperature. After incubation, sperm motility was analyzed by CASA and then cells were treated with 2.5 µl propidium iodide (50 µg/ml) or 3 µl SYBR-14. Sperm were fixed with 10 µl of 10%-formaldehyde and another 500 µl PBS was added before flowcytometry analysis. Data showed that SS31 and mTP4 bind with live sperm, and CPPs have no cytotoxic effect on sperm motility (FIGS. 10-13).

Figure 10:
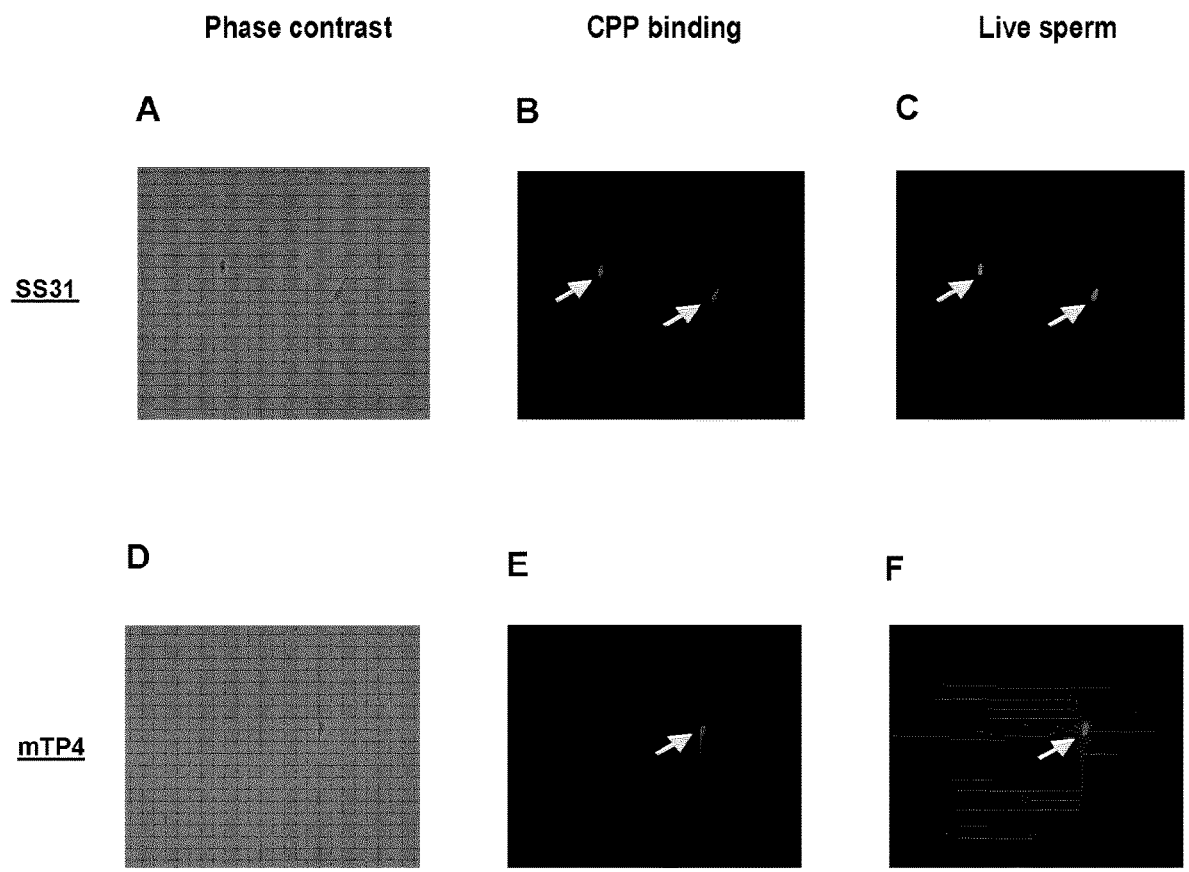
FIGS. 10A to 10F are a plurality of images showing localization of SS31 and mTP4 in bull sperm.
Figure 11:
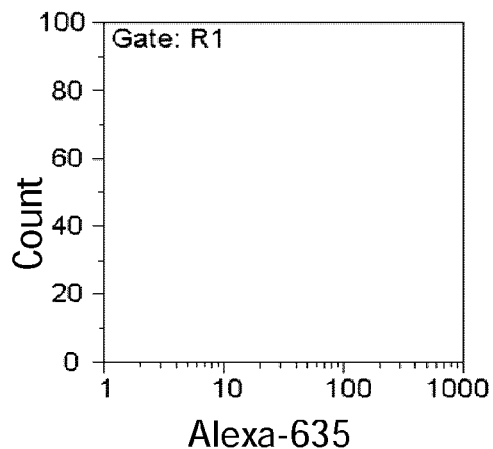
FIGS. 11A to 11C are a plurality of graphs showing flow cytometry analysis of bull sperm after incubation with Alexa fluor-633 labelled SS31 and mTP4.
Figure 11:
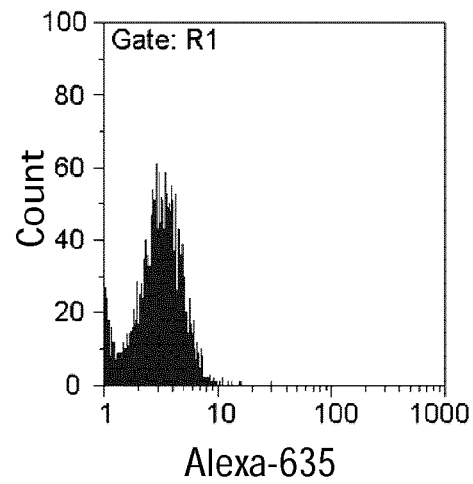
Figure 11:
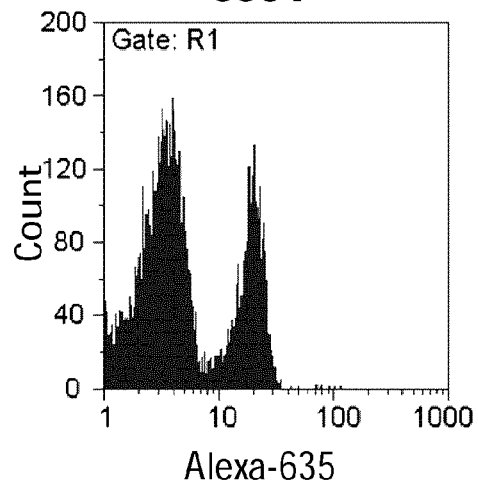
Figure 12:
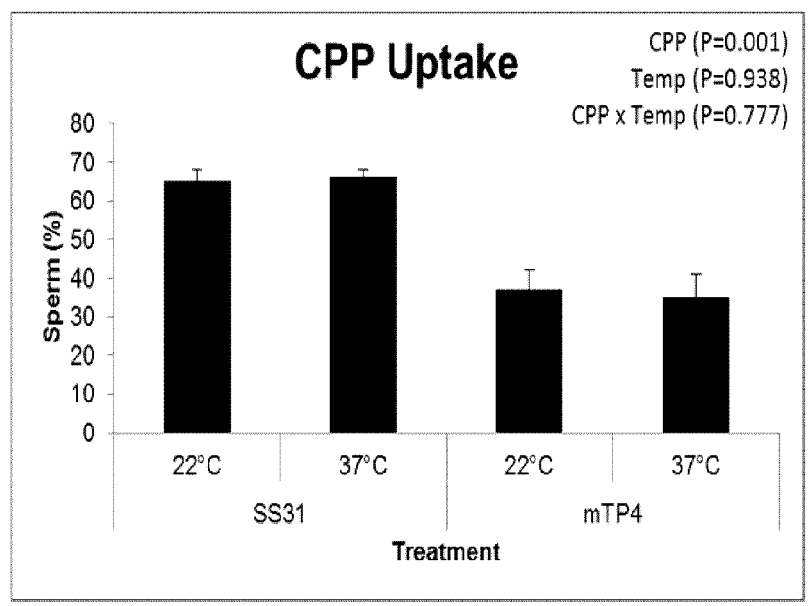
FIG. 12 is a graph depicting the uptake of SS31 and mTP4 by live sperm at 22° C. and 37° C. Each bar represents mean±SEM.
Figure 13:
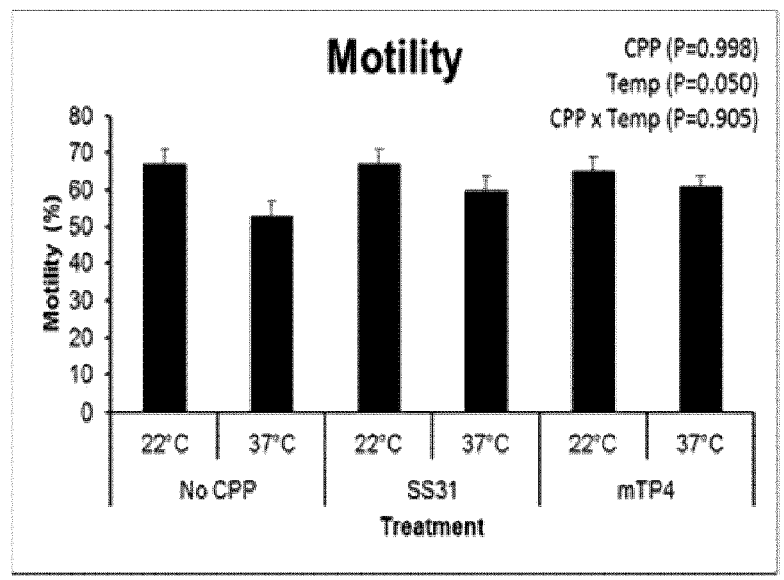
FIGS. 13A and B are two graphs depicting bull sperm properties after exposure to SS31 and mTP4.
FIG. 13B is a graph of progressive motility. Bull sperm were exposed to SS31 and mTP4 at 22° C. and 37° C. Each bar represents mean±SEM.
Figure 13:
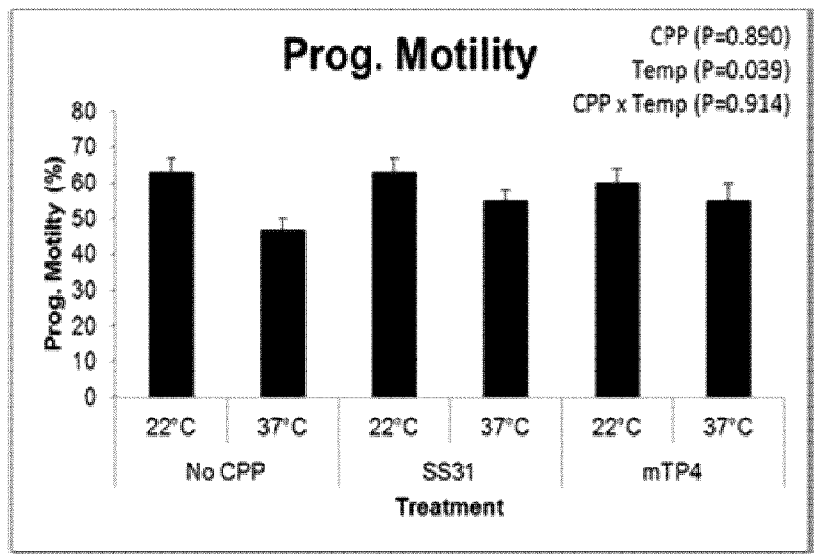

Cell penetrating peptides (SS31 and mTP4) penetrated the fresh sperm (FIG. 10). The uptake of SS31 was significantly higher than mTP4 (FIG. 11). However, the uptake of each peptide remained similar between temperatures (22° C. and 37° C.; FIG. 12). The addition of CPP at 22° C. did not improve sperm motility and progressive motility (FIG. 13). However, SS31 and mTP4 improved the sperm motility and progressive motility as compared control when CPPs were added at 37° C. (FIG. 13).

Effect of Cell Penetrating Peptides (SS31 and mTP4) on Frozen-Thaw Longevity of Bull Sperm Semen was collected from four beef bulls using electro-ejaculator. Immediately after collection, 0.5 μM SS31 or mTP4 was added per ml semen. Concentration of up to 20 μM SS31 or mTP4 were also used. Semen transported to Cryobiology Lab where semen was analyzed with CASA. Semen was further diluted with egg yolk extender to 50 million per ml, packaged in straws and frozen following a freezing curve developed in our lab. Frozen semen with and without SS31 was thawed and CASA analysis was conducted at 0 (<15 min), 2 and 4 hrs. Structural characters, i.e. plasma membrane and acrosome, were also analyzed using FITC-PNA and PI assay with flow cytometer, as described in Examples 4 and 5.

Figure 14:
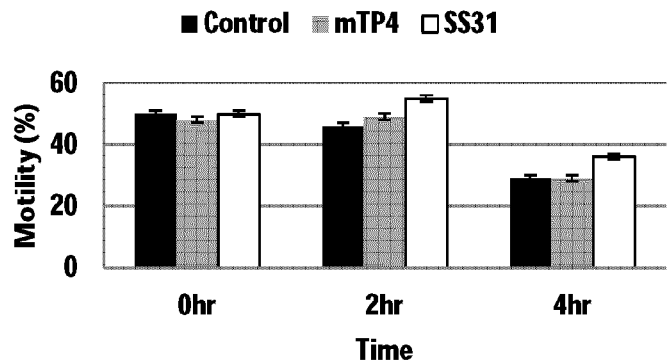
FIGS. 14A and B are two graphs depicting the effect of cell-penetrating peptides on post-thaw motility.
FIG. 14B is a graph showing the effect of mTP4 and SS31 on post-thaw sperm progressive motility at 0, 2, and 4 hrs. Each bar represents mean±SEM (N=11 independent pooled ejaculates).
Figure 14:
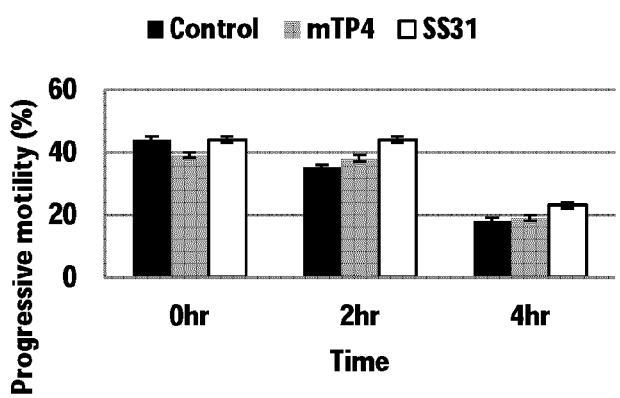
Figure 15:
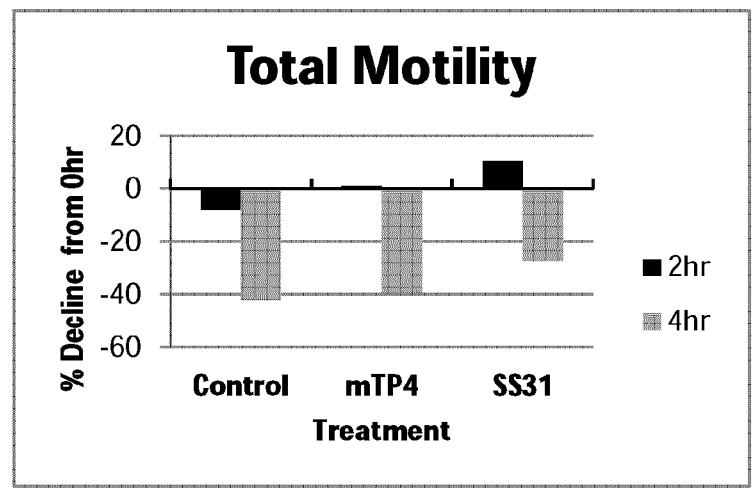
FIGS. 15A and B are two graphs depicting the effect of cell-penetrating peptides on post-thaw motility.
FIG. 15B is a graph showing percent decline in sperm progressive motility after exposure to mTP4 and SS31 for 2 and 4 hrs.
Figure 15:
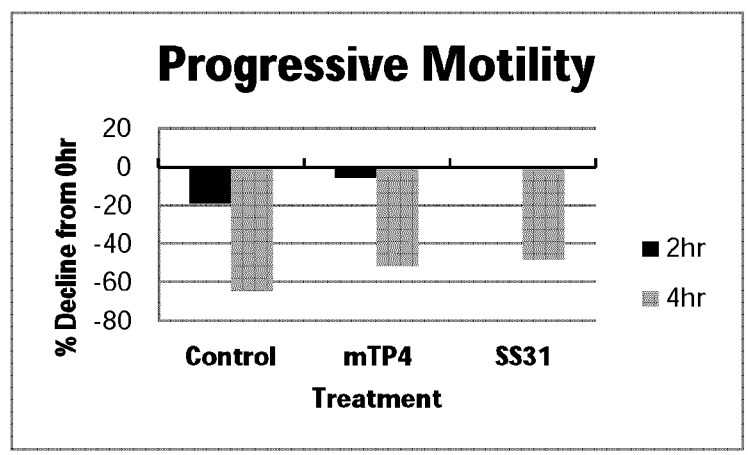

Data showed SS31 had a better post-thaw total sperm motility and progressive motility than control (FIG. 14). Percent decline motility over time (4 hr) was also lesser in SS31 group than control and mTP4 groups (FIG. 15). SS31 has a beneficial effect on post thaw sperm motility and longevity and it is considered a useful additive (i.e. antioxidant) for mammalian semen cryopreservation.

Example 9

One-Step Cholesterol: Cyclodextrin-Tris Glycerol Treatment

Figure 16:
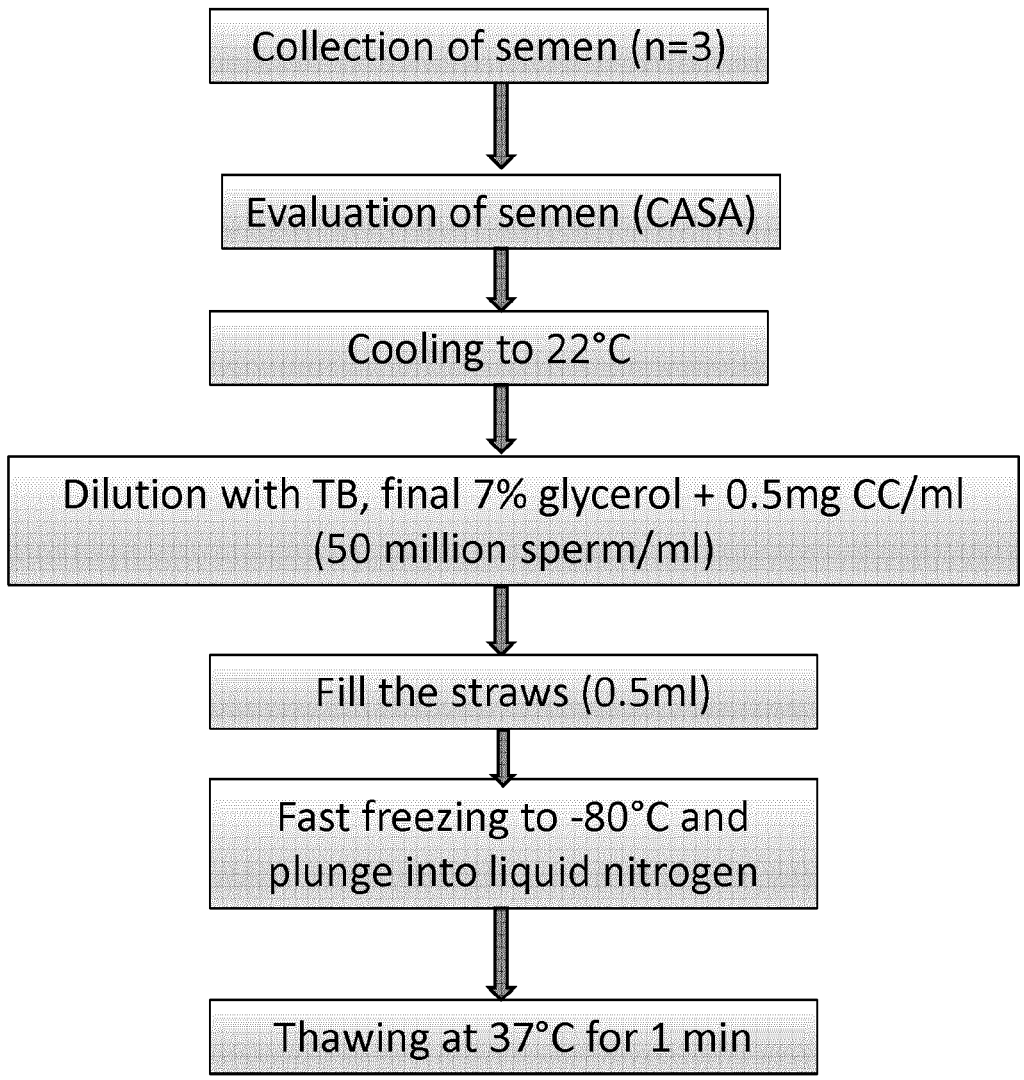
FIG. 16 is a flow chart of semen collection and processing. Beef bull semen was treated in one step by combined cyclodextrin: cholesterol-Tris glycerol composition. Abbreviations: CASA: Computer Assisted Semen Analysis, TB: tris-citric acid buffer, CC (cholesterol-cyclodextrin complex).

Semen was collected and processed as shown in FIG. 16. Semen was collected from three bulls using electro-ejaculator. Semen was analyzed with Computer Assisted Semen Analysis (CASA) and washed (2×) with tris citric acid buffer (TB). The washed semen cooled to 22° C. and diluted with TB (i.e. tris-citric acid buffer) to a final concentration of buffer containing 7% glycerol and 0.5 mg/mL cholesterol:cyclodextrin (CC complex) (i.e. cholesterol:cyclodextrin tris glycerol) at 50 million sperm/mL. The sperm was packaged in straws and fast frozen to −80° C. and plunge into liquid nitrogen. The sperm was then thawed at 37° C. for 1 min. Sperm motility was analyzed by CASA. Data showed that this one-step cholesterol:cyclodextrin-tris glycerol treatment to sperm cells prior to freezing resulted in post-thaw sperm total motility and progressive motility (FIG. 17) comparable with 2-step addition of CC complex and TB containing glycerol described in Examples 4 and 5.

Example 10

Programmable Freezing vs Vapor Freezing With and Without Egg Yolk

Programmable freezing was compared to vapor freezing. Under field conditions and in majority of breeding stations in developing countries there is no access to programmable freezer. Therefore, breeding stations in developing countries and under field conditions, semen is frozen by way of vapor freezing, i.e. 4-5 cm above liquid nitrogen. This study was conducted to assess the usefulness of egg yolk-free semen cryopreservation, using vapor freezing method compared to programmable freezing.

Methods

Semen Collection, Evaluation and Initial Processing

Figure 18:
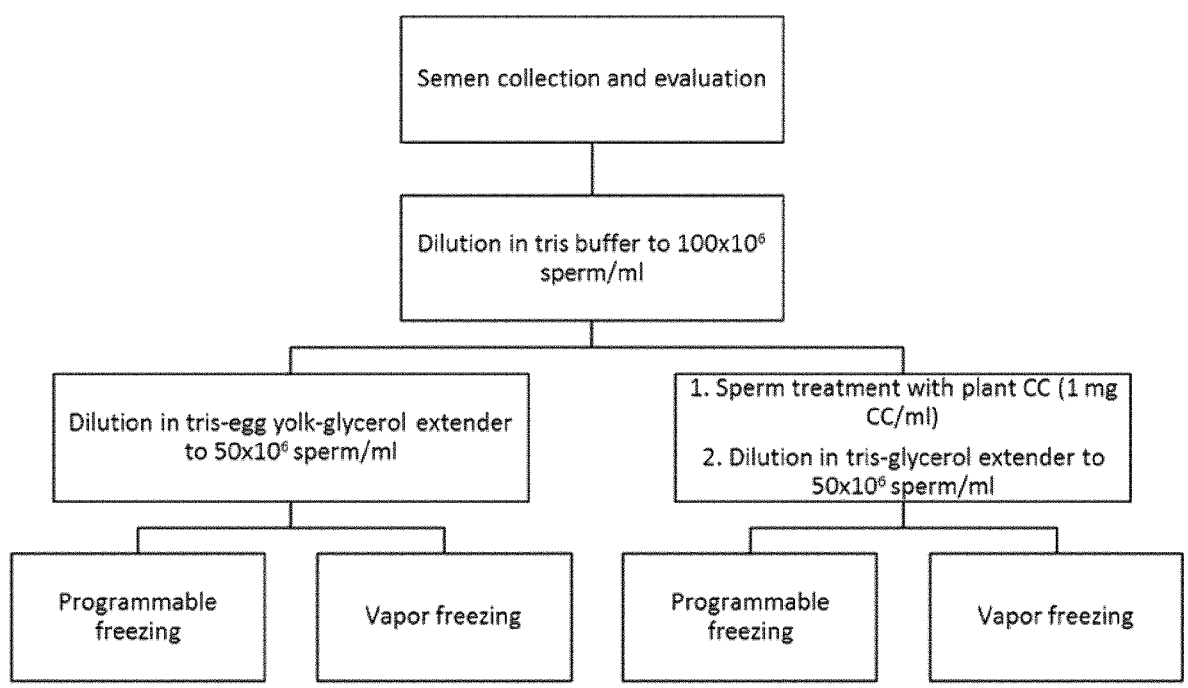
FIG. 18 is a flow chart of semen collection, evaluation and initial processing. Beef bull semen was treated with tris-egg-yolk-glycerol extender or cholesterol:cyclodextrin complex then tris-glycerol extender. Sperm in these composition were subjected to either programmable freezing or vapor freezing. Abbreviations: CC (cholesterol-cyclodextrin complex).
Figure 19:
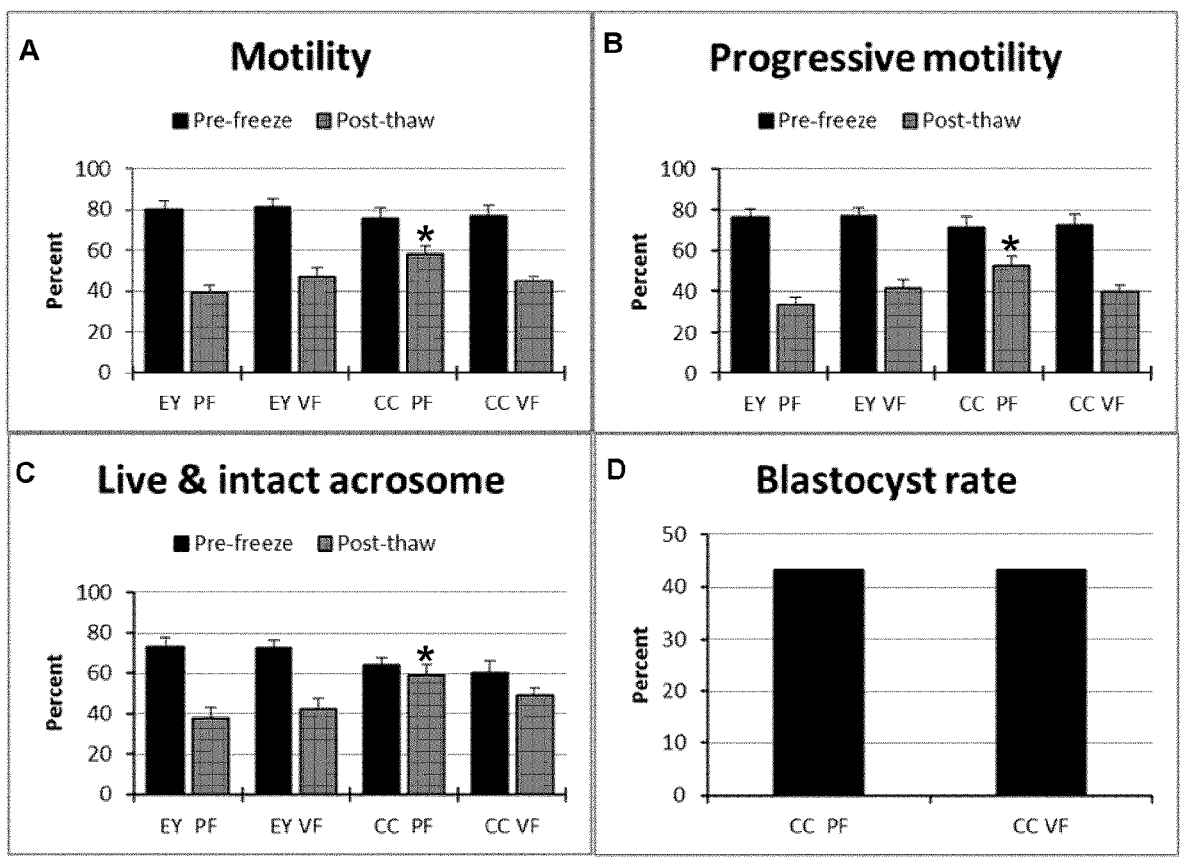
FIG. 19A to 19D are a plurality of graphs depicting post-thaw sperm characteristics.

The flow chart for semen collection, evaluation and initial processing is shown in FIG. 18. Semen was collected from 3 beef bulls on three different days with electro-ejaculation and transported to the lab at 37° C. Semen was evaluated for sperm motility and concentration by Computer Assisted Semen Analysis (CASA). Each ejaculate was diluted to $100 \times 10^6$ sperm/ml with tris-citric acid buffer (TB) and cooled to 22° C. Semen was divided into two aliquots. In aliquot 1, sperm as diluted to $50 \times 10^6$/ml with tris-egg yolk (40% v/v)-glycerol (14% v/v) extender (i.e. final glycerol % of 7% v/v). In aliquot 2, sperm was treated with plant cholesterol:cyclodextrin (CC) complex (1 mg/ml) at 22° C. for 15 min and mixed 3 times by inverting the tubes. Then, semen was diluted (1:1 v/v) to $50 \times 10^6$/ml in tris-glycerol (TG; 14% v/v glycerol) extender (final concentration was 0.5 mg/ml CC and 7% v/v glycerol) at 22° C. Each aliquot was divided into two sub-aliquots, one for programmable freezing and the other for vapor freezing.

Programmable Freezing

Semen in aliquots 1 and 2 was placed in 100 ml beakers containing water at room temperature and cooled to 4° C. in a walk-in cooler for ≥90 min. Semen was packed in 0.5 mL French straws (10 straws per bull per treatment), labelled by date, bull ID etc. Semen was frozen in a programmable cell freezer (ICE-CUBE 14-S) following freezing curve i.e. −3° C./min from 4° C. to −10° C. and −40° C./min from −10° C. to −80° C. before plunging semen straws into liquid nitrogen, as per routine. Semen was stored in liquid nitrogen tank for at least 24 h before thawing.

Vapor Freezing

Semen was packed in 0.5 ml French straws (10 straws per bull per treatment), and labelled by date, bull ID etc. Straws were placed on steel racks and cooled to +4° C. for ≥90 min in a fridge. Semen was frozen 5 cm above liquid nitrogen level, in a Styrofoam box (2 racks side by side). Semen was stored in liquid nitrogen tank for at least 24 h.

Motility, Acrosome, and Blastocyst Rate Evaluation

Post-thaw sperm cells were evaluated for totally motility, progressive motility, live and intact acrosome, and blastocyst rate as described in Examples 4 and 5.

Results

These results indicated that bovine semen can be frozen without egg yolk, using cholesterol:cyclodextrin complex and vapor freezing method. FIG. 19A-D clearly show pre-frozen semen diluted in egg yolk extender and CC-TG extender had similar sperm total motility, progressive motility, live sperm with normal acrosomes, and in vitro blastocyst rate (P>0.05). Post-thaw sperm total motility, progressive motility, live sperm with normal acrosome were better in CC-programmable freezing group than remaining treatment groups (P<0.05). However, post-thaw quality of semen diluted in CC-TG extender and frozen by vapor freezing method was similar (P>0.05) to semen frozen in egg yolk regardless of freezing method. Thus, semen treated with CC and diluted in TG extender can be successfully frozen using vapor freezing method and therefore can be used under field conditions and where there is no access to programmable freezing.

Bull semen can be frozen successfully without egg yolk, or optionally any animal source ingredient, by treating sperm with CC complex. Glycerol is still required to protect bull sperm during deep freezing stage, regardless its addition at room or refrigerated temperature. Cleavage and blastocyst rates indicated that semen treated with CC complex and frozen without egg yolk have fertilization ability in vitro. Electrophoresis data revealed that treatment of sperm with CC complex and dilution in TG extender did not change the protein profile of fresh sperm whereas egg yolk proteins bind tightly with sperm plasma membrane.

Also, CC complex and tris-glycerol can be added in one step and still protect sperm cells and motility their motility after freezing and thawing. Vapor freezing and programmable freezing can be used to maintain post-thaw quality of semen treated with CC complex and tris-glycerol.

Example 11

Figure 20:
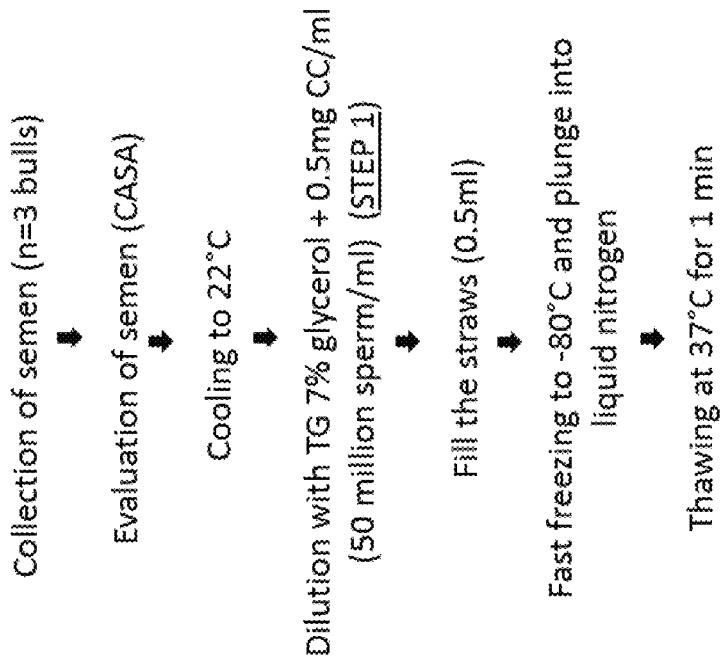
FIG. 20 is a schematic showing a two step and 1 step CC treatment protocol.
Figure 20:
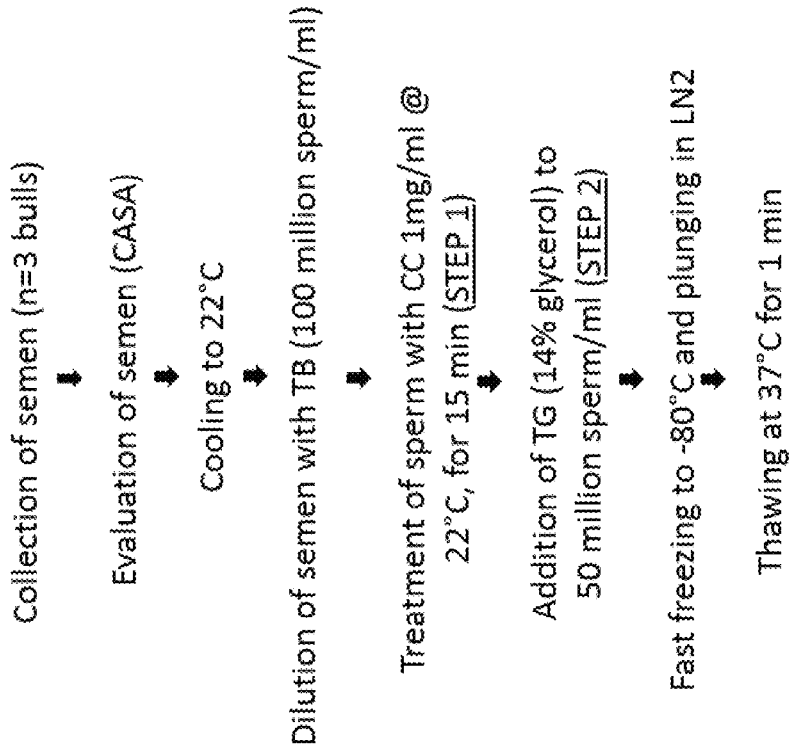

The 2-step vs. 1-step CC-treatment was compared using compositions described in Example 1. A schematic of the method is provided in FIG. 20.

TABLE 10

Comparison of post-thaw motility of 2-step (control) vs. 1-step CC-treatment for bull sperm cryopreservation.

| Sperm motility | Bull 1 | | Bull 2 | | Bull 3 | |
|---|---|---|---|---|---|---|
| | 2 step | 1 step | 2 step | 1 step | 2 step | 1 step |
| Total motility (%) | 51 | 52 | 30 | 37 | 34 | 46 |
| Progressive motility (%) | 45 | 47 | 23 | 29 | 29 | 41 |

All publications, patents and patent applications mentioned in the specification are indicative of the level of those skilled in the art to which this disclosure pertains. All publications, patents and patent applications are herein incorporated by reference to the same extent as if each individual publication, patent, or patent application was specifically and individually indicated to be incorporated by reference. The mere mentioning of the publications, patents and patent applications does not necessarily constitute an admission that they are prior art to the instant disclosure.

Although the foregoing disclosure has been described in some detail by way of illustration and examples for purposes of clarity of understanding, it is to be understood that the disclosure is not limited to the disclosed examples. To the contrary, the disclosure is intended to cover various modifications and equivalent arrangements included within the spirit and scope of the appended claims.

CITATIONS FOR REFERENCES REFERRED TO IN THE SPECIFICATION

AndroMed—Egg Yolk Free Medium for Bovine Semen (Flyer).
Anzar, M., Kroetsch, T., and Boswall, L. (2011). Cryopreservation of bull semen shipped overnight and its effect on post-thaw sperm motility, plasma membrane integrity, mitochondrial membrane potential and normal acrosomes. *Anim. Reprod. Sci.* 126(1-2), 23-31.
Akhter, S., Ansari, M. S., Rakha, B. A., Ullah, N., Andrabi, S. M. H., and Khalid, M. (2011). In vitro evaluation of Liquid-stored buffalo semen at 5 C diluted in soya lecithin based extender (Bioxcell®), Tris-Citric egg yolk, skim milk and egg Yolk-Citrate extenders. *Reproduction in domestic animals.* 46(1), 45-49.
Bergeron, A., and Manjunath, P. (2006b) New insights towards understanding the mechanisms of sperm protection by egg yolk and milk. *Mol Reprod Dev* 73(10), 1338-1344.
Blommaert, D., Franck, T., Donnay, I., Lejeune, J. P., Detilleux, J., and Serteyn, D. (2016) Substitution of egg yolk by a cyclodextrin-cholesterol complex allows a reduction of the glycerol concentration into the freezing medium of equine sperm. Cryobiology 72:27-32.
Boughter, C. T., Monje-Galvan, V., Im, W., and Klauda, J. B. (2016) Influence of Cholesterol on Phospholipid Bilayer Structure and Dynamics. *J Phys Chem B* 120(45), 11761-11772
Combes, G. B., Varner D. D., Schroeder F., Burghardt R. C. and Blanchard T. L. (2000) Effect of cholesterol on the motility and plasma membrane integrity of frozen equine spermatozoa after thawing. *Journal of reproduction and fertility. Supplement* 56, 127-132.
Crespilho, A. M., Sá Filho, M. F., Dell'Aqua Jr, J. A., Nichi, M., Monteiro, G. A., Avanzi, B. R., Martins, A., and Papa, F. O. (2012). Comparison of in vitro and in vivo fertilizing potential of bovine semen frozen in egg yolk or new lecithin based extenders. *Livestock Science,* 149(1-2), 1-6.
Hussain, S. A., Lessard, C. and Anzar, M. (2013) A strategy for improvement of postthaw quality of bison sperm. *Theriogenology* 79, 108-115.
Moussa, M., Marinet, V., Trimeche, A., Tainturier, D., and Anton, M. (2002) Low density lipoproteins extracted from hen egg yolk by an easy method: cryoprotective effect on frozen-thawed bull semen. *Theriogenology* 57(6), 1695-1706.
Muiño, R., Fernandez, M., and Peña, A. I. (2007). Post-thaw survival and longevity of bull spermatozoa frozen with an egg yolk-based or two egg yolk-free extenders after an equilibration period of 18 h. *Reproduction in domestic animals,* 42(3), 305-311.
Nolan, J. P., and Hammerstedt, R. H. (1997) Regulation of membrane stability and the acrosome reaction in mammalian sperm. *FASEB J* 11(8), 670-682.
OPTIXcell, Protein-free egg yolk-like media for frozen and fresh bovine semen, Breakthrough Technology Liposome inside (Flyer).
Pace, M. M., and Graham, E. F. (1974) Components in egg yolk which protect bovine spermatozoa during freezing. *J Anim Sci* 39(6), 1144-1149.
Polge, C. (1952) Fertilizing capacity of bull spermatozoa after freezing at 79 degrees C. *Nature* 169(4302), 626-627.
Prentice-Biensch, J. R., Singh, J., Mapletoft, R. J., and Anzar, M. (2012) Vitrification of immature bovine cumulus-oocyte complexes: effects of cryoprotectants, the vitrification procedure and warming time on cleavage and embryo development. *Reprod Biol Endocrinol* 10, 73
Purdy, P. H. and J. K. Graham. (2004) Effect of cholesterol-loaded cyclodextrin on the cryo survival of bull sperm. *Cryobiology* 48, 36-45.
Sieme, H., Oldenhof, H., and Wolkers, W. F. (2015) Sperm Membrane Behaviour during Cooling and Cryopreservation. *Reprod Domest Anim* 50 Suppl 3, 20-26.
Tomás, C., Blancha, E., Hernández, M., Gil, M. A., Roca, J., Vázquez, J. M., Martínez, E. A., Eva and Mocé, E. (2011) Treating boar sperm with cholesterol-loaded cyclodextrins widens the sperm osmotic tolerance limits and enhances the in vitro sperm fertilising ability. *Animal reproduction science* 129, 209-220.
Van Wagtendonk-de Leeuw, A. M., Haring, R. M., Kaal-Lansbergen, L. M. T. E., and Den Daas, J. H. G. (2000).

Fertility results using bovine semen cryopreserved with extenders based on egg yolk and soy bean extract. *Theriogenology*, 54(1), 57-67.

Vidament, M., Vincent, P., Yvon, J. M., Bruneau, B., and Martin, F. X. (2005). Glycerol in semen extender is a limiting factor in the fertility in asine and equine species. *Animal reproduction science*, 89, 302-305.

Wundrich, K., Paasch, U., Leicht, M., and Glander, H. J. (2006) Activation of caspases in human spermatozoa during cryopreservation—an immunoblot study. *Cell Tissue Bank* 7(2), 81-90.

The invention claimed is:

1. A method of preserving semen or sperm cells comprising:

combining an ejaculate containing sperm cells and/or isolated sperm cells with a cholesterol: carrier complex to provide a cholesterol: carrier sperm cells composition and combining the cholesterol: carrier sperm cells composition with a sperm cells preserving composition comprising a cryoprotectant, and a biological buffer to provide a preserved sperm cells composition; wherein the cholesterol: carrier complex and the sperm cells preserving composition are substantially free of animal phospholipid, animal protein, and/or animal lipoprotein; or combining an ejaculate containing sperm cells and/or isolated sperm cells with a sperm cells preserving composition to provide a preserved sperm cells composition, the sperm cells preserving composition comprising a cholesterol: carrier complex, a cryoprotectant, and a biological buffer, wherein the sperm cells preserving composition is substantially free of animal phospholipid, animal protein and/or animal lipoprotein.

2. The method of claim 1, further comprising freezing the preserved sperm cells composition and wherein each of the steps prior to freezing are performed above 10° C., above 15° C., or at or above room temperature, at about 22° C. or about 37° C., optionally wherein the freezing is an accelerated freezing method, and/or wherein the ejaculate is combined with the sperm cells preserving composition and frozen to about −80° C. in about 60 minutes about 55 minutes, about 45 minutes about 35 minutes or any time within about 30 minutes to about 90 minutes; and/or further comprises thawing frozen preserved sperm cells.

3. The method of claim 1, wherein the cholesterol: carrier complex is a cholesterol:cyclodextrin complex (CC complex) and/or polyethylene glycol (PEG) conjugated cholesterol (PEG-C conjugate), optionally wherein the CC complex is at least about 0.125 mg/mL, between about 0.125 mg/mL to about 10 mg/mL, or between about 0.5 mg/mL to about 2 mg/mL of the sperm cells preserving composition and/or the preserved sperm cells composition; and/or the cryoprotectant comprises or is glycerol, optionally wherein the glycerol concentration is between about 3% and about 15% (v/v), between about 5% and about 11% (v/v), between about 5% and about 9% (v/v), or between about 5% and about 7% (v/v); and/or the sperm cells preserving composition further comprises one or more of a carbohydrate, a pH stabilizer, an antibiotic, and/or a cell permeable anti-oxidant peptide, optionally wherein the carbohydrate is fructose, the pH stabilizer is citric acid monohydrate, the antibiotic is gentamycin, tylosin, and/or linco-spectin, and/or the cell permeable anti-oxidant peptide is SS31 and/or mTP4.

4. The method of claim 1, wherein the cholesterol: carrier complex comprises plant cholesterol or animal cholesterol, optionally wherein the plant cholesterol is beta-sitosterol, campesterol, stigmasterol, or vegetal-derived cholesterol, or a combination thereof, and the animal cholesterol is derived from a sheep; and the cholesterol: carrier complex comprises cyclodextrin selected from α-cyclodextrin, β-cyclodextrin, γ-cyclodextrin, methyl-α-cyclodextrin, methyl-β-cyclodextrin, methyl-γ-cyclodextrin, and hydroxypropyl-β-cyclodextrin, optionally wherein the cyclodextrin is methyl-β-cyclodextrin and the ratio by weight of cholesterol to methyl-β-cyclodextrin is from about 1:100 to about 30:100, or about 9:100.

5. The method of claim 1, wherein the ejaculate is diluted using a warm dilution solution to a selected sperm concentration prior to combining ejaculate with the sperm cells preserving composition, optionally wherein the warm dilution solution has a temperature of about 37° C.; and/or after diluting using a warm dilution solution, the solution is cooled to about room temperature, optionally wherein the room temperature is about 22° C.; and/or prior to freezing, the preserved sperm cells composition is packaged in a straw.

6. The method of claim 1, wherein the ejaculate is from a mammal, optionally wherein the mammal is an ungulate, optionally wherein the ungulate is a livestock ungulate or a domesticated ungulate, optionally wherein the ungulate is a ruminant, stallion, boar, bull or bison.

7. The method of claim 3, wherein the preserved sperm cells composition comprises sperm cells to CC complex ratio of from about 25 million sperm cells per mg CC complex to about 100 million sperm cells per mg CC complex, or about 50 million sperm cells per mg CC complex.

8. The method of claim 1, wherein each combining step is less than 15 min.

9. A method of preserving sperm comprising combining an ejaculate containing sperm cells and/or isolated sperm cells with a sperm cells preserving composition comprising a cell permeable anti-oxidant peptide, to provide a protected sperm cells composition, wherein the protected sperm cells composition comprises a cholesterol: carrier complex, and wherein the sperm cells preserving composition is substantially free of animal phospholipid, animal protein, and/or animal lipoprotein.

10. The method of claim 9, wherein the sperm cells preserving composition comprises a biological buffer and/or a cryoprotectant, optionally wherein the cryoprotectant is glycerol, optionally wherein the glycerol concentration is between about 3% and about 15% (v/v), between about 5% and about 11% (v/v), between about 5% and about 9% (v/v) or between about 5% and about 7% (v/v).

11. The method of claim 9, wherein the sperm cells preserving composition comprises a cholesterol:cyclodextrin complex (CC complex) and/or polyethylene glycol (PEG) conjugated cholesterol (PEG-C conjugate), and a biological buffer, optionally comprising at least 0.125 mg/ml, about 0.125 mg/mL to about 10 mg/ml, or between about 0.5 mg/mL to about 4 mg/mL CC complex, optionally wherein the cholesterol: carrier complex comprises plant cholesterol or animal cholesterol, wherein the plant cholesterol is beta-sitosterol, campesterol, stigmasterol, or vegetal-derived cholesterol, or a combination thereof, or the animal cholesterol is from a sheep, and/or wherein the cholesterol: carrier complex comprises methyl-β-cyclodextrin, optionally wherein the ratio by weight of cholesterol to methyl-β-cyclodextrin is about 9:100, and/or wherein the sperm cells preserving composition is reconstituted from powder form, and/or wherein the protected sperm cells composition in an individual dosage form comprises at least 1,000,000 sperm/dose, or from 1 to 50 million sperm/dose, and/or wherein sperm to CC complex ratio is from about 25 million sperm per mg CC complex to about 100 million sperm per mg CC complex, or about 50 million sperm per mg CC complex.

12. The method of claim 9, wherein the method further comprises freezing the protected sperm cells composition, optionally i) wherein the freezing is an accelerated freezing method, and/or ii) wherein the ejaculate is combined with the sperm cells preserving composition and frozen to about −80° C. in about 60 minutes, about 55 min minutes, about 45 minutes, about 35 minutes or any time within about 30 minutes to about 90 minutes.

13. A method of accelerated freezing of semen or sperm cells comprising:

a) combining an ejaculate containing sperm cells and/or isolated sperm cells with i) a cholesterol: carrier complex preserving composition to provide a cholesterol: carrier sperm cells composition and cooling to room temperature prior to or after combining with the cholesterol: carrier complex preserving composition, and combining the cholesterol: carrier sperm cells composition with a sperm cells preserving composition comprising a cryoprotectant and/or a carbohydrate, and a biological buffer to provide a preserved sperm cells composition and cooling to about 10° C. or about 4° C. at a rate of temperature drop of about 0.5-2° C. per minute, prior to or after combining with the sperm cells preserving composition; or ii) a sperm cells preserving composition comprising a cholesterol: carrier complex, a cryoprotectant and/or a carbohydrate, and a biological buffer to provide a preserved sperm cells composition and cooling to room temperature prior to or after combining with the sperm cells preserving composition, further cooling to about 10° C. or about 4° C. at a rate of temperature drop of about 0.5-2° C. per minute after combining with the sperm cells preserving composition;

b) cooling the preserved sperm cells composition to about or less than −80° C. at a rate of temperature drop of about −20° C. per minute to about −60° C. per minute; optionally further cooling the preserved sperm cells composition, or further cooling by inserting the composition in liquid nitrogen;

wherein the cholesterol: carrier complex preserving composition and the sperm cells preserving composition are substantially free of animal phospholipid, animal protein, and/or animal lipoprotein;

optionally i) wherein the cholesterol: carrier complex preserving composition comprises a cholesterol:cyclodextrin complex (CC complex); and/or ii) wherein the cholesterol: carrier complex comprises plant cholesterol or animal cholesterol, optionally wherein the plant cholesterol is beta-sitosterol, campesterol, stigmasterol, or vegetal-derived cholesterol, or a combination thereof, or the animal cholesterol is from a sheep; and/or iii) wherein the cholesterol: carrier complex preserving composition or the sperm cells preserving composition is reconstituted from powder form, and/or the preserved sperm cells composition is in an individual dosage form comprising at least 1,000,000 sperm per dose, or from 1 to 50 million sperm per dose, and/or wherein sperm to CC complex ratio is from about 25 million sperm per mg CC complex to about 100 million sperm per mg CC complex, or about 50 million sperm per mg CC complex; and/or iv) wherein prior to step a) an ejaculate containing sperm cells and/or isolated sperm cells is cooled to room temperature; and/or v) wherein the sperm cells preserving composition comprises a cryoprotectant.

14. The method of claim 13 wherein the cholesterol: carrier complex preserving composition comprises
a cholesterol: carrier complex, optionally cholesterol: cyclodextrin complex (CC complex) and/or PEG-C conjugate, and a biological buffer.

15. The method of claim 14, wherein the cholesterol: carrier complex preserving composition comprises a cell permeable anti-oxidant peptide.

16. The method of claim 13, wherein the cholesterol: carrier complex preserving composition and the sperm cells preserving composition are substantially free of animal source ingredients.

17. The method of claim 13, wherein the step a) i) or a) ii) further comprises incubating for about 10-15 minutes after cooling to room temperature.

18. The method of claim 13, wherein the cholesterol: carrier complex preserving composition comprises at least 0.125 mg/ml, between about 0.125 mg/mL to about 10 mg/ml, or between about 0.5 mg/mL to about 4 mg/mL CC complex.

19. The method of claim 13, wherein the cyclodextrin is methyl-β-cyclodextrin, optionally wherein the ratio by weight of cholesterol to methyl-β-cyclodextrin is about 9:100.

20. The method of claim 13, wherein the cryoprotectant is glycerol, optionally wherein the glycerol concentration is between about 3% and about 15% (v/v), between about 5% and about 11% (v/v), between about 5% and about 9% (v/v) or between about 5% and about 7% (v/v).

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthteic peptides
<220> FEATURE:
<221> NAME/KEY: MISC_FEATURE
<222> LOCATION: (1)..(1)
<223> OTHER INFORMATION: Xaa = D-Arg, where  D refers to "handedness"
      (i.e. D-stereoisomers)
<220> FEATURE:
<221> NAME/KEY: MISC_FEATURE
<222> LOCATION: (2)..(2)
<223> OTHER INFORMATION: Xaa = 2',6'-dimethylTyr

<400> SEQUENCE: 1

Xaa Xaa Lys Phe
1

<210> SEQ ID NO 2
<211> LENGTH: 15
<212> TYPE: PRT
<213> ORGANISM: Artificial Sequence
<220> FEATURE:
<223> OTHER INFORMATION: Synthetic peptides
<220> FEATURE:
<221> NAME/KEY: MISC_FEATURE
<222> LOCATION: (1)..(1)
<223> OTHER INFORMATION: Xaa = 2',6'-dimethylTyr
<220> FEATURE:
<221> NAME/KEY: MISC_FEATURE
<222> LOCATION: (2)..(2)
<223> OTHER INFORMATION: Xaa = D-Met, where D refers to "handedness"
      (i.e. D-stereoisomers)

<400> SEQUENCE: 2

Xaa Xaa Trp Trp Arg Arg Ser Arg Thr Asn Ser Leu Arg Tyr Thr
1               5                   10                  15
```